US006599719B2

(12) United States Patent
Yu et al.

(10) Patent No.: US 6,599,719 B2
(45) Date of Patent: *Jul. 29, 2003

(54) NUCLEIC ACID MOLECULES ENCODING TUMOR NECROSIS FACTOR-GAMMA-ALPHA

(75) Inventors: Guo-Liang Yu, San Mateo, CA (US); Jian Ni, Rockville, MD (US); Craig A. Rosen, Laytonsville, MD (US)

(73) Assignee: Human Genome Sciences, Inc., Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/131,237

(22) Filed: Aug. 7, 1998

(65) Prior Publication Data

US 2003/0027284 A1 Feb. 6, 2003

Related U.S. Application Data

(63) Continuation-in-part of application No. 09/005,020, filed on Jan. 9, 1998, which is a continuation-in-part of application No. 08/461,246, filed on Jun. 5, 1995, which is a continuation-in-part of application No. PCT/US94/12880, filed on Nov. 7, 1994.
(60) Provisional application No. 60/074,047, filed on Feb. 9, 1998.

(51) Int. Cl.[7] .................. C12N 15/28; C12N 15/63; C07K 14/525; C07H 21/04
(52) U.S. Cl. ............ 435/69.5; 435/252.3; 435/320.1; 435/69.7; 435/91.4; 536/23.5; 536/24.1; 930/140; 530/324
(58) Field of Search ................. 435/69.5, 320.1, 435/252.3, 91.4, 69.7; 536/235, 24.1; 930/140; 530/324

(56) References Cited

U.S. PATENT DOCUMENTS

| | | | |
|---|---|---|---|
| 4,677,063 A | | 6/1987 | Mark et al. |
| 5,464,938 A | | 11/1995 | Smith et al. ............... 530/350 |
| 5,476,781 A | * | 12/1995 | Moyer et al. ............ 435/240.2 |
| 5,874,077 A | | 2/1999 | Kriegler et al. |

FOREIGN PATENT DOCUMENTS

| | | | |
|---|---|---|---|
| CA | 2 114 311 A | | 5/1993 |
| EP | 0585939 A2 | | 3/1994 |
| WO | 9112340 | * | 8/1991 |
| WO | WO 94/05691 | | 3/1994 |
| WO | WO 94/18325 | | 8/1994 |
| WO | 9517205 | * | 6/1995 |
| WO | 9612033 | * | 4/1996 |
| WO | WO 96/14328 | | 5/1996 |
| WO | WO 96/40774 | * | 12/1996 |
| WO | WO 99/23105 | | 5/1999 |
| WO | WO 00/08139 | * | 2/2000 |

OTHER PUBLICATIONS

Immunology: A Short Course, by Eli Benjamini, Sidney Leskowitz (Editor), Wiley–Liss, Inc., New York, NY., Jul. 1991, p. 40.*
Orkin et al. Report and Recommendation of the Panel to Assess the NIH Investment in Research on Gene Therapy, issued by the National Institutes of Health, Dec. 7, 1995.*
Bowie et al. Deciphering the message in protein sequences: tolerance to amino acid substitutions. Science, (Mar. 16, 1990) 247 (4948) 1306–10.*
Ngo et al., in The Protein Folding Problem and Tertiary Structure Prediction, Merz and Le Grand (Eds), Aug. 1994, Springer Verlag, pp. 433 and 492–495.*
Migone et al. "TL1A Is a TNF–like Ligand for DR3 and TR6/DcR3 and Functions as a T Cell Costumulator." *Immunity* 16: 479–492, Mar. 2002.
Chew et al. "A novel secreted splieve variant of vascular endothelial cell growth inhibitor." *FASEB Journal* 16. 742–744. May 2002.
Rosenblum et al. , (1991) Cancer Communications 3(1)21–27.
Pennington, J. , ASM News (1992) 58(9) 479–482.
Gatanaga et al. (1990) Proc. Natl. Acad. Sci. USA 87:8781–8784.
Nedwin et al., (1985) Nucleic Acids Research 13(17):6361–6373.
Hallahan et al. (1989) Proc. Natl. Acad. Sci. USA 86:10104–10107.
Porter, A., 91991) Tibtech 9:158–162.
Boehringer Mannheim, Internal Publication entitled "Cell Death Detection ELISA", Cat. No. 1544 675 (1993).
Hsu et al., (1993) J. Biological Chemistry 268(22):16430–16436.
Grazzioli et al., J. Biological Chem. 269(35):22304–22309.
Liu et al., (1992) J. Immunology 148(12) 3789–3798.
Crowe et al., (1994) J. Immunology 168:79–89.

(List continued on next page.)

Primary Examiner—David S. Romeo
(74) Attorney, Agent, or Firm—Human Genome Sciences, Inc.

(57) ABSTRACT

Human TNF-gamma-alpha and TNF-gamma-beta polypeptides and DNA (RNA) encoding such polypeptides and a procedure for producing such polypeptides by recombinant techniques is disclosed. Also disclosed are methods for utilizing such polypeptides to inhibit cellular growth, for example in a tumor or cancer, for facilitating wound-healing, to provide resistance against infection, induce inflammatory acitvities, and stimulating the growth of certain cell types to treat diseases, for example restenosis. Also disclosed are diagnostic methods for detecting a mutation in the TNF-gamma-alpha and TNF-gamma-beta nucleic acid sequences or overexperession of the TNF-gamma-alpha and TNF-gamma-beta polypeptides. Antagonists against such polypeptides and their use as a therapeutic to treat cachexia, septic shock, cerebral malaria, inflammation, arthritis and graft-rejection are also disclosed.

42 Claims, 32 Drawing Sheets

OTHER PUBLICATIONS

Douglas et al., (1994) Clin. Chem 40(9):1833–1837.
Genbank Database Accession No. AAD08783 (Dec. 8, 1998).
Goh et al. (1993) Thyroid Disorders 22(4):651–656.
Masegi et al. (1993) Biotechnology Letters 15(11):1107–1110.
Tavernier et al. (1990) J. Mol. Biol. 211(2):493–502.
Vilcek et al. (1991) J. Biol. Chem. 266(12)7313–7316.
Zhang et al. (1992) J. Biol. Chem. 267(33):24069–24075.
Zhai et al. "Inhibition of Angiogenesis and Breast Cancer Xenograft Tumor Growth by VEGI, A Novel Cytokine of the TNF Superfamily," *Int. J. Cancer* 82:131–136 (1999).

Accession No. P51435 (May 30, 2000).*

Liu et al., Production of Transmembrane and Secreted Forms of Tumor Necrosis Factor (TNF)–alpha BY HIV–1–specific CD4* Cytolytic T Lumphocyte Clones, Journal of Immunobiology, vol. 148, 3780–3798 (Jun. 12, 1992).*

Ni, et al., Novel Strategies for Discovery of TNF Ligand, Receptor and Signal Transducer Super family Members, Journal of Interferon and Cytokine Research, vol. 18: A43 (May 1998).*

* cited by examiner

Figure 1A

```
   1 CCCAATCAAGAGAAATTCCATACTATCACCAGTTGGCCGACTTTCCAAGTCTAGTGCAGA   60

61 AATCCAAGGCACCTCACACCTAGAGTTCCTATACCTCTGAGACTCCAGAGGAAAGAACAA  120

121 GACAGTGCAGAAGGATATGTTAGAACCCACTGAAAACCTAGAAGGTTGAAAAGGAAGCAT  180

181 ACCCTCCTGACCTATAAGAAAATTTTCAGTCTGCAGGGGATATCCTTGTGGCCCAAGAC  240

241 ATTGGTGTTATCATTTGACTAAGAGGAAATTATTTGTGGTGAGCTCTGAGTGAGGATTAG  300

301 GACCAGGGAGATGCCAAGTTTCTATCACTTACCTCATGCCTGTAAGACAAGTGTTTTGTT  360

361 CCAATTGATGAATGGGGAGAAAACAGTTCAGCCAATCACTTATGGGCACAGAATGGAATT  420

421 TGAAGGGTCTGGTGCCTGCCCTTGTCATACGTAAACAAGAGAGGCATCGATGAGTTTTAT  480

481 CTGAGTCATTTGGGAAAGGATAATTCTTGCACCAAGCCATTTTCCTAAACACAGAAGAAT  540

541 AGGGGGATTCCTTAACCTTCATTGTTCTCCAGGATCATAGGTCTCAGGATAAATTAAAAA  600

601 TTTTCAGGTCAGACCACTCAGTCTCAGAAAGGCAAAGTAATTTGCCCCAGGTCACTAGTC  660

661 CAAGATGTTATTCTCTTTGAACAAATGTGTATGTCCAGTCACATATTCTTCATTCATTCC  720

721 TCCCCAAAGCAGTTTTTAGCTGTTAGGTATATTCGATCACTTTAGTCTATTTTGAAAATG  780

781 ATATGAGACGCTTTTTAAGCAAAGTCTACAGTTTCCCAATGAGAAAATTAATCCTCTTTC  840
   1   M  R  R  F  L  S  K  V  Y  S  F  P  M  R  K  L  I  L  F  L   20

841 TTGTCTTTCCAGTTGTGAGACAAACTCCCACACAGCACTTTAAAAATCAGTTCCCAGCTC  900
  21   V  F  P  V  V  R  Q  T  P  T  Q  H  F  K  N  Q  F  P  A  L   40

901 TGCACTGGGAACATGAACTAGGCCTGGCCTTCACCAAGAACCGAATGAACTATACCAACA  960
  41   H  W  E  H  E  L  G  L  A  F  T  K  N  R  M  N  Y  T  N  K   60

961 AATTCCTGCTGATCCCAGAGTCGGGAGACTACTTCATTTACTCCCAGGTCACATTCCGTG 1020
  61   F  L  L  I  P  E  S  G  D  Y  F  I  Y  S  Q  V  T  F  R  G   80

1021 GGATGACCTCTGAGTGCAGTGAAATCAGACAAGCAGGCCGACCAAACAAGCCAGACTCCA 1080
  81   M  T  S  E  C  S  E  I  R  Q  A  G  R  P  N  K  P  D  S  I  100

1081 TCACTGTGGTCATCACCAAGGTAACAGACAGCTACCCTGAGCCAACCCAGCTCCTCATGG 1140
 101   T  V  V  I  T  K  V  T  D  S  Y  P  E  P  T  Q  L  L  M  G  120

1141 GGACCAAGTCTGTATGCGAAGTAGGTAGCAACTGGTTCCAGCCCATCTACCTCGGAGCCA 1200
 121   T  K  S  V  C  E  V  G  S  N  W  F  Q  P  I  Y  L  G  A  M  140
```

Figure 1B

```
1201 TGTTCTCCTTGCAAGAAGGGGACAAGCTAATGGTGAACGTCAGTGACATCTCTTTGGTGG 1260
 141  F  S  L  Q  E  G  D  K  L  M  V  N  V  S  D  I  S  L  V  D  160

1261 ATTACACAAAAGAAGATAAAACCTTCTTTGGAGCCTTCTTACTATAGGAGGAGAGCAAAT 1320
 161  Y  T  K  E  D  K  T  F  F  G  A  F  L  L  *              174

1321 ATCATTATATGAAAGTCCTCTGCCACCGAGTTCCTAATTTTCTTTGTTCAAATGTAATTA 1380

1381 TAACCAGGGGTTTTCTTGGGGCCGGGAGTAGGGGGCATTCCACAGGGACAACGGTTTAGC 1440

1441 TATGAAATTTGGGGCCAAAATTTCACACTTCATGTGCCTTACTGATGAGAGTACTAACTG 1500

1501 GAAAAAGGCTGAAGAGAGCAAATATATTATTAAGATGGGTTGGAGGATTGGCGAGTTTCT 1560

1561 AAATATTAAGACACTGATCACTAAATGAATGGATGATCTACTCGGGTCAGGATTGAAAGA 1620

1621 GAAATATTTCAACACCTCCCTGCTATACAATGGTCACCAGTGGTCCAGTTATTGTTCAAT 1680

1681 TTGATCATAAATTTGCTTCAATTCAGGAGCTTTGAAGGAAGTCCAAGGAAAGCTCTAGAA 1740

1741 AACAGTATAAACTTTCAGAGGCAAAATCCTTCACCAATTTTTCCACATACTTTCATGCCT 1800

1801 TGCCTAAAAAAAATGAAAAGAGAGTTGGTATGTCTCATGAATGTTCACACAGAAGGAGTT 1860

1861 GGTTTTCATGTCATCTACAGCATATGAGAAAAGCTACCTTTCTTTTGATTATGTACACAG 1920

1921 ATATCTAAATAAGGAAGTTTGAGTTTCACATGTATATCCCAAATACAACAGTTGCTTGTA 1980

1981 TTCAGTAGAGTTTTCTTGCCCACCTATTTTGTGCTGGGTTCTACCTTAACCCAGAAGACA 2040

2041 CTATGAAAAACAAGACAGACTCCACTCAAAATTTATATGAACACCACTAGATACTTCCTG 2100

2101 ATCAAACATCAGTCAACATACTCTAAAGAATAACTCCAAGTCTTGGCCAGGCGCAGTGGC 2160

2161 TCACACCTGTAATCCCAACACTTTGGGAGGCCAAGGTGGGTGGATCATCTAAGGCCGGGA 2220

2221 GTTCAAGACCAGCCTGACCAACGTGGAGAAACCCCATCTCTACTNAAAATACNAAATTAG 2280

2281 CCGGGCGTGGTAGCGCATGGCTGTAANCCTGGCTACTCAGGAGGCCGAGGCAGAANAATT 2340

2341 NCTTGAACTGGGGAGGCAGAGGTTGCGGTGAGCCCAGANCGCGCCATTGCACTCCAGCCT 2400

2401 GGGTAACAAGAGCAAAACTCTGTCCAAAAAAAAAAAAAAAAA                   2442
```

FIG. 2A

MATCH WITH FIG. 2B

Tissue distribution of TNFgamma mRNA

Expression of TNFgamma in HUVEC

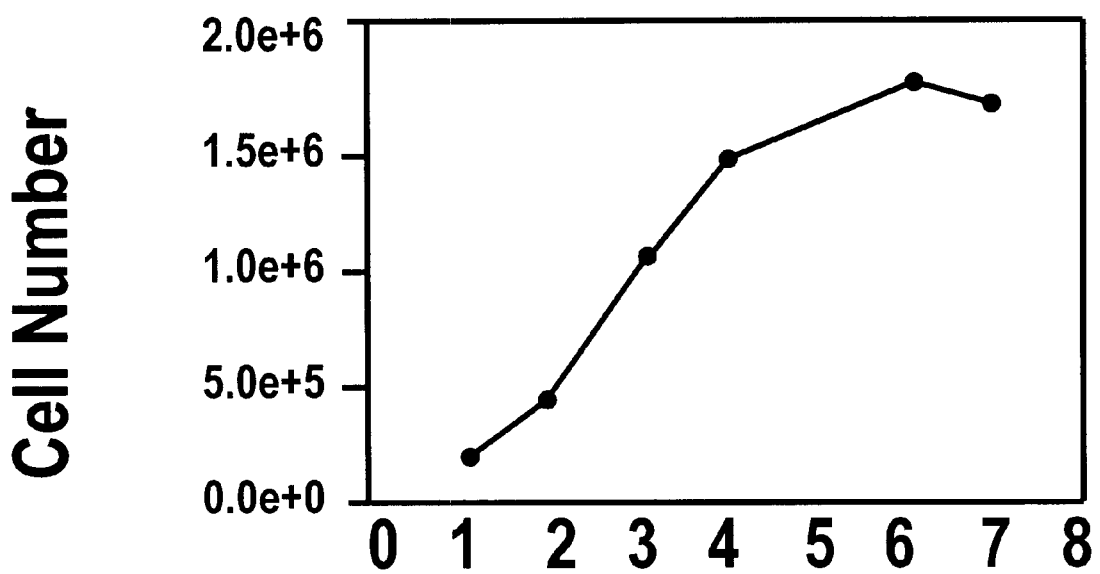
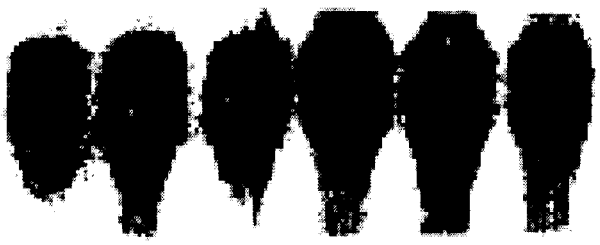
FIG. 4

Expression of TNFγ in baculovirus system 1   2   3   4

TNFγ

FIG.6

TNF-gamma-alpha vs. TNF-gamma-beta

| | | |
|---|---|---|
| TNF-gamma-alpha | 1 | CCCAATCAAGAGAAATTCCATACTATCACCAGTTGGCCGACTTTCCAAG 49 |
| TNF-gamma-alpha | 50 | TCTAGTGCAGAAATCCAAGGCACCTCACACCTAGAGTTCCTATACCTCTG 99 |
| TNF-gamma-alpha | 100 | AGACTCCAGACGAAAGAACAAGACAGTGCAGAAGGATATGTTAGAACCCA 149 |
| TNF-gamma-alpha | 150 | CTGAAAACCTAGAAGGTTGAAAAGGAAGCATACCCTCCTGACCTATAAGA 199 |
| TNF-gamma-alpha | 200 | AAATTTTCAGTCTGCAGGGGGATATCCTTGTGGCCCAAGACATTGGTGTT 249 |
| TNF-gamma-alpha | 250 | ATCATTTGACTAAGAGGAAATTATTTGTGGTGAGCTCTGAGTGAGGATTA 299 |
| TNF-gamma-alpha | 300 | GGACCAGGGAGATGCCAAGTTTCTATCACTTACCTCATGCCTGTAAGACA 349 |
| TNF-gamma-alpha | 350 | AGTGTTTTGTTCCAATTGATGAATGGGGAGAAAACAGTTCAGCCAATCAC 399 |
| TNF-gamma-alpha | 400 | TTATGGGCACAGAATGGAATTTGAAGGGTCTGGTGCCTGCCCTTGTCATA 449 |
| TNF-gamma-alpha | 450 | CGTAAACAAGAGAGGCATCGATGAGTTTTATCTGAGTCATTTGGGAAAGG 499 |
| TNF-gamma-alpha | 500 | ATAATTCTTGCACCAAGCCATTTTCCTAAACACAGAAGAATAGGGGGATT 549 |
| TNF-gamma-alpha | 550 | CCTTAACCTTCATTGTTCTCCAGGATCATAGGTCTCAGGATAAATTAAAA 599 |
| | | | ||    ||   ||   |||     |  |  || |
| TNF-gamma-beta | 1 |     ATGGCCGAGGATCTGGGACTGAGCTTTGGGGAAACAGCCAGTGTGGAA 48 |
| TNF-gamma-alpha | 600 | ATTTTCAGGTCAGACCACTCAGTCTCAGAAAGGCAAAGTAATTTGCCCCA 649 |
| | | || |      || |||    |      | |||  |||       | |
| TNF-gamma-beta | 49 | ATGCTGCCAGAGCACGGCAGCTGCAGGCCCAACGCCAGGAGCAGCAGCGC 98 |
| TNF-gamma-alpha | 650 | GGTCACTAGTCCAAGATGTTATTCTCTTTGAACAAATGTGTATGTCCAGT 699 |
| | | |    || | |||   ||    ||     | | |
| TNF-gamma-beta | 99 | ACGCTGGGCTCTCACCTGCTGCCTGGTGTTGCTCCCCTTCCTTGCAGGAC 148 |
| TNF-gamma-alpha | 700 | CACATATTCTTCATTCATTCCTCCCCAAAGCAGTTTTTAGCTGTTAGGTA 749 |
| | | |     |     |   ||    |      | |
| TNF-gamma-beta | 149 | TCACCACATACCTGCTTGTCAGCCAGCTCCGGGCCCAGGGAGAGGCCTGT 198 |
| TNF-gamma-alpha | 750 | TATTCGATCACTTTAGTCTATTTTGAAAATGATATGAGACGCTTTTTAAG 799 |
| | | |||      |     |||   |      | |
| TNF-gamma-beta | 199 | GTGCAGTTCCAGGCTCTAAAAGGACAGGAGTTTGCACCTTCACATCAGCA 248 |

FIG. 18A

```
                    TNF-gamma-alpha vs. TNF-gamma-beta

TNF-gamma-alpha  800 CAAAGTCTACAGTTTCCCAATGAGAAAATTAATCCTCTTTCTTGTCTTTC  849
                     | |  |       |   | |             | |
TNF-gamma-beta   249 AGTTTATGCACCTCTTAGAGCAGACGGAGATAAGCCAAGGGCACACCTGA  298

TNF-gamma-alpha  850 CAGTTGTGAGACAAACTCCCACACAGCACTTTAAAAATCAGTTCCCAGCT  899
                     ||||||||||||||||||||||||||||||||||||||||||||||||||
TNF-gamma-beta   299 CAGTTGTGAGACAAACTCCCACACAGCACTTTAAAAATCAGTTCCCAGCT  348

TNF-gamma-alpha  900 CTGCACTGGGAACATGAACTAGGCCTGGCCTTCACCAAGAACCGAATGAA  949
                     ||||||||||||||||||||||||||||||||||||||||||||||||||
TNF-gamma-beta   349 CTGCACTGGGAACATGAACTAGGCCTGGCCTTCACCAAGAACCGAATGAA  398

TNF-gamma-alpha  950 CTATACCAACAAATTCCTGCTGATCCCAGAGTCGGGAGACTACTTCATTT  999
                     ||||||||||||||||||||||||||||||||||||||||| ||||||||
TNF-gamma-beta   399 CTATACCAACAAATTCCTGCTGATCCCAGAGTCGGGAGACTACTTCATTT  448

TNF-gamma-alpha 1000 ACTCCCAGGTCACATTCCGTGGGATGACCTCTGAGTGCAGTGAAATCAGA 1049
                     ||||||||||||||||||||||||||||||||||||||||||||||||||
TNF-gamma-beta   449 ACTCCCAGGTCACATTCCGTGGGATGACCTCTGAGTGCAGTGAAATCAGA  498

TNF-gamma-alpha 1050 CAAGCAGGCCGACCAAACAAGCCAGACTCCATCACTGTGGTCATCACCAA 1099
                     ||||||||||||||||||||||||||||||||||||||||||||||||||
TNF-gamma-beta   499 CAAGCAGGCCGACCAAACAAGCCAGACTCCATCACTGTGGTCATCACCAA  548

TNF-gamma-alpha 1100 GGTAACAGACAGCTACCCTGAGCCAACCCAGCTCCTCATGGGGACCAAGT 1149
                     ||||||||||||||||||||||||||||||||||||||||||||||||||
TNF-gamma-beta   549 GGTAACAGACAGCTACCCTGAGCCAACCCAGCTCCTCATGGGGACCAAGT  598

TNF-gamma-alpha 1150 CTGTATGCGAAGTAGGTAGCAACTGGTTCCAGCCCATCTACCTCGGAGCC 1199
                     ||||||||||||||||||||||||||||||||||||||||||||||||||
TNF-gamma-beta   599 CTGTATGCGAAGTAGGTAGCAACTGGTTCCAGCCCATCTACCTCGGAGCC  648

TNF-gamma-alpha 1200 ATGTTCTCCTTGCAAGAAGGGGACAAGCTAATGGTGAACGTCAGTGACAT 1249
                     ||||||||||||||||||||||||||||||||||||||||||||||||||
TNF-gamma-beta   649 ATGTTCTCCTTGCAAGAAGGGGACAAGCTAATGGTGAACGTCAGTGACAT  698

TNF-gamma-alpha 1250 CTCTTTGGTGGATTACACAAAAGAAGATAAAACCTTCTTTGGAGCCTTCT 1299
                     ||||||||||||||||||||||||||||||||||||||||||||||||||
TNF-gamma-beta   699 CTCTTTGGTGGATTACACAAAAGAAGATAAAACCTTCTTTGGAGCCTTCT  748

TNF-gamma-alpha 1300 TACTATAGGAGGAGAGCAAATATCATTATATGAAAGTCCTCTGCCACCGA 1349
                     ||||||||||||||||||||||||||||||||||||||||||||||||||
TNF-gamma-beta   749 TACTATAGGAGGAGAGCAAATATCATTATATGAAAGTCCTCTGCCACCGA  798

TNF-gamma-alpha 1350 GTTCCTAATTTTCTTTGTTCAAATGTAATTATAACCAGGGGTTTTCTTGG 1399
                     ||||||||||||||||||||||||||||||||||||||||||||||||||
TNF-gamma-beta   799 GTTCCTAATTTTCTTTGTTCAAATGTAATTATAACCAGGGGTTTTCTTGG  848

TNF-gamma-alpha 1400 GGCCGGGAGTAGGGGGCATTCCACAGGGACAACGGTTTAGCTATGAAATT 1449
                     ||||||||||| ||||||||||||||||||||||||||||||||||||||
TNF-gamma-beta   849 GGCCGGGAGTA.GGGGCATTCCACAGGGACAACGGTTTAGCTATGAAATT  897
```

FIG. 18B

TNF-gamma-alpha vs. TNF-gamma-beta

```
TNF-gamma-alpha 1450 TGGGG.CCAAAATTTCACACTTCATGTGCCTTACTGATGAGAGTACTAAC 1498
                    |||||  |||||||||||||||||||||||||||||||||||||||||||
TNF-gamma-beta   898 TGGGGCCCAAAATTTCACACTTCATGTGCCTTACTGATGAGAGTACTAAC 947

TNF-gamma-alpha 1499 TGGAAAAAGGCTGAAGAGAGCAAATATATTATTAAGATGGGTTGGAGGAT 1548
                    ||||||||||||||||||||||||||||||||||||||||||||||||||
TNF-gamma-beta   948 TGGAAAAAGGCTGAAGAGAGCAAATATATTATTAAGATGGGTTGGAGGAT 997

TNF-gamma-alpha 1549 TGGCGAGTTTCTAAATATTAAGACACTGATCACTAAATGAATGGATGATC 1598
                    ||||||||||||||||||||||||||||||||||||||||||||||||||
TNF-gamma-beta   998 TGGCGAGTTTCTAAATATTAAGACACTGATCACTAAATGAATGGATGATC 1047

TNF-gamma-alpha 1599 TACTCGGGTCAGGATTGAAAGAGAAATATTTCAACACCTCCCTGCTATAC 1648
                    ||||||||||||||||||||||||||||||||||||||||| |||||||||
TNF-gamma-beta  1048 TACTCGGGTCAGGATTGAAAGAGAAATATTTCAACACCTTCCTGCTATAC 1097

TNF-gamma-alpha 1649 AATGGTCACCAGTGGTCCAGTTATTGTTCAATTTGATCATAAATTTGCTT 1698
                    |||||||||||||||||||
TNF-gamma-beta  1098 AATGGTCACCAGTGGTCCA 1116

TNF-gamma-alpha 1699 CAATTCAGGAGCTTTGAAGGAAGTCCAAGGAAAGCTCTAGAAAACAGTAT 1748

TNF-gamma-alpha 1749 AAACTTTCAGAGGCAAAATCCTTCACCAATTTTTCCACATACTTTCATGC 1798

TNF-gamma-alpha 1799 CTTGCCTAAAAAAAATGAAAAGAGAGTTGGTATGTCTCATGAATGTTCAC 1848

TNF-gamma-alpha 1849 ACAGAAGGAGTTGGTTTTCATGTCATCTACAGCATATGAGAAAAGCTACC 1898

TNF-gamma-alpha 1899 TTTCTTTTGATTATGTACACAGATATCTAAATAAGGAAGTTTGAGTTTCA 1948

TNF-gamma-alpha 1949 CATGTATATCCCAAATACAACAGTTGCTTGTATTCAGTAGAGTTTTCTTG 1998

TNF-gamma-alpha 1999 CCCACCTATTTTGTGCTGGGTTCTACCTTAACCCAGAAGACACTATGAAA 2048

TNF-gamma-alpha 2049 AACAAGACAGACTCCACTCAAAATTTATATGAACACCACTAGATACTTCC 2098

TNF-gamma-alpha 2099 TGATCAAACATCAGTCAACATACTCTAAAGAATAACTCCAAGTCTTGGCC 2148

TNF-gamma-alpha 2149 AGGCGCAGTGGCTCACACCTGTAATCCCAACACTTTGGGAGGCCAAGGTG 2198

TNF-gamma-alpha 2199 GGTGGATCATCTAAGGCCCGGGAGTTCAAGACCAGCCTGACCAACGTGGAG 2248
```

FIG. 18C

TNF-gamma-alpha vs. TNF-gamma-beta

```
TNF-gamma-alpha  2249  AAACCCCATCTCTACTNAAAATACNAAATTAGCCGGGCGTGGTAGCCGCAT  2298

TNF-gamma-alpha  2299  GGCTGTAANCCTGGCTACTCAGGAGGCCGAGGCAGAANAATTNCTTGAAC  2348

TNF-gamma-alpha  2349  TGGGGAGGCAGAGGTTGCGGTGAGCCCAGANCGCGCCATTGCACTCCAGC  2398

TNF-gamma-alpha  2399  CTGGGTAACAAGAGCAAAACTCTGTCCAAAAAAAAAAAAAAAAA        2442
```

FIG. 18D

TNF-gamma-alpha vs. TNF-gamma-beta

```
TNF-gamma-beta    1   MAEDLGLSFGETASVEMLPEHGSCRPKARSSSARWALTCCLVLLPFLAGL  50

TNF-gamma-alpha   1                              MRRFLSKVYSFPMRKLILFLVFP  23

TNF-gamma-beta   51   TTYLLVSQLRAQGEACVQFQALKGQEFAPSHQQVYAPLRADGDKPRAHLT 100

TNF-gamma-alpha  24   VVRQTPTQHFKNQFPALHWEHELGLAFTKNRMNYTNKFLLIPESGDYFIY  73
                      ||||||||||||||||||||||||||||||||||||||||||||||||||
TNF-gamma-beta  101   VVRQTPTQHFKNQFPALHWEHELGLAFTKNRMNYTNKFLLIPESGDYFIY 150

TNF-gamma-alpha  74   SQVTFRGMTSECSEIRQAGRPNKPDSITVVITKVTDSYPEPTQLLMGTKS 123
                      ||||||||||||||||||||||||||||||||||||||||||||||||||
TNF-gamma-beta  151   SQVTFRGMTSECSEIRQAGRPNKPDSITVVITKVTDSYPEPTQLLMGTKS 200

TNF-gamma-alpha 124   VCEVGSNWFQPIYLGAMFSLQEGDKLMVNVSDISLVDYTKEDKTFFGAFL 173
                      ||||||||||||||||||||||||||||||||||||||||||||||||||
TNF-gamma-beta  201   VCEVGSNWFQPIYLGAMFSLQEGDKLMVNVSDISLVDYTKEDKTFFGAFL 250

TNF-gamma-alpha 174   L 174
                      |
TNF-gamma-beta  251   L 251
```

FIG. 19

TNF-gamma-beta

```
  1 ATGGCCGAGGATCTGGGACTGAGCTTTGGGGAAACAGCCAGTGTGGAAATGCTGCCAGAG   60
  1  M  A  E  D  L  G  L  S  F  G  E  T  A  S  V  E  M  L  P  E   20

61 CACGGCAGCTGCAGGCCCAAGGCCAGGAGCAGCAGCGCACGCTGGGCTCTCACCTGCTGC  120
 21  H  G  S  C  R  P  K  A  R  S  S  S  A  R  W  A  L  T  C  C   40

121 CTGGTGTTGCTCCCCTTCCTTGCAGGACTCACCACATACCTGCTTGTCAGCCAGCTCCGG  180
 41  L  V  L  L  P  F  L  A  G  L  T  T  Y  L  L  V  S  Q  L  R   60

181 GCCCAGGGAGAGGCCTGTGTGCAGTTCCAGGCTCTAAAAGGACAGGAGTTTGCACCTTCA  240
 61  A  Q  G  E  A  C  V  Q  F  Q  A  L  K  G  Q  E  F  A  P  S   80

241 CATCAGCAAGTTTATGCACCTCTTAGAGCAGACGGAGATAAGCCAAGGGCACACCTGACA  300
 81  H  Q  Q  V  Y  A  P  L  R  A  D  G  D  K  P  R  A  H  L  T  100

301 GTTGTGAGACAAACTCCCACACAGCACTTTAAAAATCAGTTCCCAGCTCTGCACTGGGAA  360
101  V  V  R  Q  T  P  T  Q  H  F  K  N  Q  F  P  A  L  H  W  E  120

361 CATGAACTAGGCCTGGCCTTCACCAAGAACCGAATGAACTATACCAACAAATTCCTGCTG  420
121  H  E  L  G  L  A  F  T  K  N  R  M  N  Y  T  N  K  F  L  L  140

421 ATCCCAGAGTCGGGAGACTACTTCATTTACTCCCAGGTCACATTCCGTGGGATGACCTCT  480
141  I  P  E  S  G  D  Y  F  I  Y  S  Q  V  T  F  R  G  M  T  S  160

481 GAGTGCAGTGAAATCAGACAAGCAGGCCGACCAAACAAGCCAGACTCCATCACTGTGGTC  540
161  E  C  S  E  I  R  Q  A  G  R  P  N  K  P  D  S  I  T  V  V  180

541 ATCACCAAGGTAACAGACAGCTACCCTGAGCCAACCCAGCTCCTCATGGGGACCAAGTCT  600
181  I  T  K  V  T  D  S  Y  P  E  P  T  Q  L  L  M  G  T  K  S  200

601 GTATGCGAAGTAGGTAGCAACTGGTTCCAGCCCATCTACCTCGGAGCCATGTTCTCCTTG  660
201  V  C  E  V  G  S  N  W  F  Q  P  I  Y  L  G  A  M  F  S  L  220

661 CAAGAAGGGGACAAGCTAATGGTGAACGTCAGTGACATCTCTTTGGTGGATTACACAAAA  720
221  Q  E  G  D  K  L  M  V  N  V  S  D  I  S  L  V  D  Y  T  K  240

721 GAAGATAAAACCTTCTTTGGAGCCTTCTTACTATAGGAGGAGAGCAAATATCATTATATG  780
241  E  D  K  T  F  F  G  A  F  L  L                              251

781 AAAGTCCTCTGCCACCGAGTTCCTAATTTTCTTTGTTCAAATGTAATTATAACCAGGGGT  840

841 TTTCTTGGGGCCCGGGAGTAGGGGCATTCCACAGGGACAACGGTTTAGCTATGAAATTTGG  900
```

FIG. 20A

TNF-gamma-beta

```
 901  GGCCCAAAATTTCACACTTCATGTGCCTTACTGATGAGAGTACTAACTGGAAAAAGGCTG   960
 961  AAGAGAGCAAATATATTATTAAGATGGGTTGGAGGATTGGCGAGTTTCTAAATATTAAGA  1020
1021  CACTGATCACTAAATGAATGGATGATCTACTCGGGTCAGGATTGAAAGAGAAATATTTCA  1080
1081  ACACCTTCCTGCTATACAATGGTCACCAGTGGTCCA                          1116
```

FIG. 20B

SEQUENCE LISTING

```
<160> NUMBER OF SEQ ID NOS: 24

<210> SEQ ID NO 1
<211> LENGTH: 2442
<212> TYPE: DNA
<213> ORGANISM: Homo sapiens
<220> FEATURE:
<221> NAME/KEY: CDS
<222> LOCATION: (783)..(1304)
<221> NAME/KEY: mat_peptide
<222> LOCATION: (864)..(1304)
<221> NAME/KEY: sig_peptide
<222> LOCATION: (783)..(863)
<221> NAME/KEY: misc_feature
<222> LOCATION: (2265)
<223> OTHER INFORMATION: n equals a, t, g, or c
<221> NAME/KEY: misc_feature
<222> LOCATION: (2273)
<223> OTHER INFORMATION: n equals a, t, g, or c
<221> NAME/KEY: misc_feature
```

```
<222> LOCATION: (2307)
<223> OTHER INFORMATION: n equals a, t, g, or c
<221> NAME/KEY: misc_feature
<222> LOCATION: (2336)
<223> OTHER INFORMATION: n equals a, t, g, or c
<221> NAME/KEY: misc_feature
<222> LOCATION: (2341)
<223> OTHER INFORMATION: n equals a, t, g, or c
<221> NAME/KEY: misc_feature
<222> LOCATION: (2379)
<223> OTHER INFORMATION: n equals a, t, g, or c

<400> SEQUENCE: 1
```

| | |
|---|---:|
| cccaatcaag agaaattcca tactatcacc agttggccga ctttccaagt ctagtgcaga | 60 |
| aatccaaggc acctcacacc tagagttcct atacctctga gactccagag gaaagaacaa | 120 |
| gacagtgcag aaggatatgt tagaacccac tgaaaaccta gaaggttgaa aaggaagcat | 180 |
| accctcctga cctataagaa aattttcagt ctgcaggggg atatccttgt ggcccaagac | 240 |
| attggtgtta tcatttgact aagaggaaat tatttgtggt gagctctgag tgaggattag | 300 |
| gaccagggag atgccaagtt tctatcactt acctcatgcc tgtaagacaa gtgttttgtt | 360 |
| ccaattgatg aatggggaga aaacagttca gccaatcact tatgggcaca gaatggaatt | 420 |
| tgaagggtct ggtgcctgcc cttgtcatac gtaaacaaga gaggcatcga tgagttttat | 480 |
| ctgagtcatt tgggaaagga taattcttgc accaagccat tttcctaaac acagaagaat | 540 |
| agggggattc cttaaccttc attgttctcc aggatcatag gtctcaggat aaattaaaaa | 600 |
| ttttcaggtc agaccactca gtctcagaaa ggcaaagtaa tttgccccag gtcactagtc | 660 |
| caagatgtta ttctctttga acaaatgtgt atgtccagtc acatattctt cattcattcc | 720 |
| tccccaaagc agtttttagc tgttaggtat attcgatcac tttagtctat tttgaaaatg | 780 |

```
at atg aga cgc ttt tta agc aaa gtc tac agt ttc cca atg aga aaa      827
   Met Arg Arg Phe Leu Ser Lys Val Tyr Ser Phe Pro Met Arg Lys
       -25             -20             -15 tta atc ctc ttt ctt gtc ttt cca gtt gtg aga caa act ccc aca cag    875
Leu Ile Leu Phe Leu Val Phe Pro Val Val Arg Gln Thr Pro Thr Gln
       -10             -5              -1  1 cac ttt aaa aat cag ttc cca gct ctg cac tgg gaa cat gaa cta ggc    923
His Phe Lys Asn Gln Phe Pro Ala Leu His Trp Glu His Glu Leu Gly
    5               10              15              20 ctg gcc ttc acc aag aac cga atg aac tat acc aac aaa ttc ctg ctg    971
Leu Ala Phe Thr Lys Asn Arg Met Asn Tyr Thr Asn Lys Phe Leu Leu
            25              30              35 atc cca gag tcg gga gac tac ttc att tac tcc cag gtc aca ttc cgt   1019
Ile Pro Glu Ser Gly Asp Tyr Phe Ile Tyr Ser Gln Val Thr Phe Arg
        40              45              50 ggg atg acc tct gag tgc agt gaa atc aga caa gca ggc cga cca aac   1067
Gly Met Thr Ser Glu Cys Ser Glu Ile Arg Gln Ala Gly Arg Pro Asn
    55              60              65 aag cca gac tcc atc act gtg gtc atc acc aag gta aca gac agc tac   1115
Lys Pro Asp Ser Ile Thr Val Val Ile Thr Lys Val Thr Asp Ser Tyr
        70              75              80 cct gag cca acc cag ctc ctc atg ggg acc aag tct gta tgc gaa gta   1163
Pro Glu Pro Thr Gln Leu Leu Met Gly Thr Lys Ser Val Cys Glu Val
85              90              95              100 ggt agc aac tgg ttc cag ccc atc tac ctc gga gcc atg ttc tcc ttg   1211
Gly Ser Asn Trp Phe Gln Pro Ile Tyr Leu Gly Ala Met Phe Ser Leu
            105             110             115 caa gaa ggg gac aag cta atg gtg aac gtc agt gac atc tct ttg gtg   1259
Gln Glu Gly Asp Lys Leu Met Val Asn Val Ser Asp Ile Ser Leu Val
        120             125             130
```

-continued

```
gat tac aca aaa gaa gat aaa acc ttc ttt gga gcc ttc tta cta        1304
Asp Tyr Thr Lys Glu Asp Lys Thr Phe Phe Gly Ala Phe Leu Leu
        135                 140                 145 taggaggaga gcaaatatca ttatatgaaa gtcctctgcc accgagttcc taattttctt   1364
tgttcaaatg taattataac caggggtttt cttggggccg ggagtagggg gcattccaca   1424
gggacaacgg tttagctatg aaatttgggg ccaaaatttc acacttcatg tgccttactg   1484
atgagagtac taactggaaa aaggctgaag agagcaaata tattattaag atgggttgga   1544
ggattggcga gtttctaaat attaagacac tgatcactaa atgaatggat gatctactcg   1604
ggtcaggatt gaaagagaaa tatttcaaca cctccctgct atacaatggt caccagtggt   1664
ccagttattg ttcaatttga tcataaattt gcttcaattc aggagctttg aaggaagtcc   1724
aaggaaagct ctagaaaaca gtataaactt tcagaggcaa atccttcac caattttttcc    1784 acatactttc atgccttgcc taaaaaaaat gaaaagagag ttggtatgtc tcatgaatgt    1844
tcacacagaa ggagttggtt ttcatgtcat ctacagcata tgagaaaagc tacctttctt   1904
ttgattatgt acacagatat ctaaataagg aagtttgagt ttcacatgta tatcccaaat    1964
acaacagttg cttgtattca gtagagtttt cttgcccacc tattttgtgc tgggttctac    2024
cttaacccag aagacactat gaaaacaag acagactcca ctcaaaattt atatgaacac    2084
cactagatac ttcctgatca aacatcagtc aacatactct aaagaataac tccaagtctt    2144
ggccaggcgc agtggctcac acctgtaatc ccaacacttt gggaggccaa ggtgggtgga    2204
tcatctaagg ccgggagttc aagaccagcc tgaccaacgt ggagaaaccc catctctact    2264
naaaatacna aattagccgg gcgtggtagc gcatggctgt aaacctggct actcaggagg    2324
ccgaggcaga anaattnctt gaactgggga ggcagaggtt gcggtgagcc caganncgcgc    2384 cattgcactc cagcctgggt aacaagagca aaactctgtc caaaaaaaaa aaaaaaaa     2442

<210> SEQ ID NO 2
<211> LENGTH: 174
<212> TYPE: PRT
<213> ORGANISM: Homo sapiens

<400> SEQUENCE: 2

Met Arg Arg Phe Leu Ser Lys Val Tyr Ser Phe Pro Met Arg Lys Leu
        -25                 -20                 -15

Ile Leu Phe Leu Val Phe Pro Val Val Arg Gln Thr Pro Thr Gln His
    -10                  -5                  -1   1               5

Phe Lys Asn Gln Phe Pro Ala Leu His Trp Glu His Glu Leu Gly Leu
                10                  15                  20

Ala Phe Thr Lys Asn Arg Met Asn Tyr Thr Asn Lys Phe Leu Leu Ile
            25                  30                  35

Pro Glu Ser Gly Asp Tyr Phe Ile Tyr Ser Gln Val Thr Phe Arg Gly
        40                  45                  50

Met Thr Ser Glu Cys Ser Glu Ile Arg Gln Ala Gly Arg Pro Asn Lys
    55                  60                  65

Pro Asp Ser Ile Thr Val Val Ile Thr Lys Val Thr Asp Ser Tyr Pro
70                  75                  80                  85

Glu Pro Thr Gln Leu Leu Met Gly Thr Lys Ser Val Cys Glu Val Gly
                90                  95                  100

Ser Asn Trp Phe Gln Pro Ile Tyr Leu Gly Ala Met Phe Ser Leu Gln
                105                 110                 115

Glu Gly Asp Lys Leu Met Val Asn Val Ser Asp Ile Ser Leu Val Asp
```

120                 125                 130
Tyr Thr Lys Glu Asp Lys Thr Phe Phe Gly Ala Phe Leu Leu
        135                 140                 145

<210> SEQ ID NO 3
<211> LENGTH: 233
<212> TYPE: PRT
<213> ORGANISM: Homo sapiens

<400> SEQUENCE: 3

Met Ser Thr Glu Ser Met Ile Arg Asp Val Glu Leu Ala Glu Ala
 1               5                  10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Ser Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 4
<211> LENGTH: 205
<212> TYPE: PRT
<213> ORGANISM: Homo sapiens

<400> SEQUENCE: 4

Met Thr Pro Pro Glu Arg Leu Phe Leu Pro Arg Val Cys Gly Thr Thr
 1               5                  10                  15

Leu His Leu Leu Leu Leu Gly Leu Leu Leu Val Leu Leu Pro Gly Ala
                20                  25                  30

Gln Gly Leu Pro Gly Val Gly Leu Thr Pro Ser Ala Ala Gln Thr Ala
            35                  40                  45

Arg Gln His Pro Lys Met His Leu Ala His Ser Thr Leu Lys Pro Ala
        50                  55                  60

Ala His Leu Ile Gly Asp Pro Ser Lys Gln Asn Ser Leu Leu Trp Arg

```
                    65                  70                  75                  80
Ala Asn Thr Asp Arg Ala Phe Leu Gln Asp Gly Phe Ser Leu Ser Asn
                        85                  90                  95

Asn Ser Leu Leu Val Pro Thr Ser Gly Ile Tyr Phe Val Tyr Ser Gln
                100                 105                 110

Val Val Phe Ser Gly Lys Ala Tyr Ser Pro Lys Ala Pro Ser Ser Pro
            115                 120                 125

Leu Tyr Leu Ala His Glu Val Gln Leu Phe Ser Ser Gln Tyr Pro Phe
        130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                    165                 170                 175

Gln Gly Asp Gln Leu Ser Thr His Thr Asp Gly Ile Pro His Leu Val
                180                 185                 190

Leu Ser Pro Ser Thr Val Phe Phe Gly Ala Phe Ala Leu
            195                 200                 205

<210> SEQ ID NO 5
<211> LENGTH: 244
<212> TYPE: PRT
<213> ORGANISM: Homo sapiens

<400> SEQUENCE: 5

Met Gly Ala Leu Gly Leu Glu Gly Arg Gly Gly Arg Leu Gln Gly Arg
  1               5                  10                  15

Gly Ser Leu Leu Leu Ala Val Ala Gly Ala Thr Ser Leu Val Thr Leu
                20                  25                  30

Leu Leu Ala Val Pro Ile Thr Val Leu Ala Val Leu Ala Leu Val Pro
            35                  40                  45

Gln Asp Gln Gly Gly Leu Val Thr Glu Thr Ala Asp Pro Gly Ala Gln
        50                  55                  60

Ala Gln Gln Gly Leu Gly Phe Gln Lys Leu Pro Glu Glu Pro Glu
65                  70                  75                  80

Thr Asp Leu Ser Pro Gly Leu Pro Ala Ala His Leu Ile Gly Ala Pro
                    85                  90                  95

Leu Lys Gly Gln Gly Leu Gly Trp Glu Thr Thr Lys Glu Gln Ala Phe
                100                 105                 110

Leu Thr Ser Gly Thr Gln Phe Ser Asp Ala Glu Gly Leu Ala Leu Pro
            115                 120                 125

Gln Asp Gly Leu Tyr Tyr Leu Tyr Cys Leu Val Gly Tyr Arg Gly Arg
        130                 135                 140

Ala Pro Pro Gly Gly Gly Asp Pro Gln Gly Arg Ser Val Thr Leu Arg
145                 150                 155                 160

Ser Ser Leu Tyr Arg Ala Gly Gly Ala Tyr Gly Pro Gly Thr Pro Glu
                    165                 170                 175

Leu Leu Leu Glu Gly Ala Glu Thr Val Thr Pro Val Leu Asp Pro Ala
                180                 185                 190

Arg Arg Gln Gly Tyr Gly Pro Leu Trp Tyr Thr Ser Val Gly Phe Gly
            195                 200                 205

Gly Leu Val Gln Leu Arg Arg Gly Glu Arg Val Tyr Val Asn Ile Ser
        210                 215                 220

His Pro Asp Met Val Asp Phe Ala Arg Gly Lys Thr Phe Phe Gly Ala
225                 230                 235                 240
```

Val Met Val Gly

<210> SEQ ID NO 6
<211> LENGTH: 278
<212> TYPE: PRT
<213> ORGANISM: Rattus norvegicus

<400> SEQUENCE: 6

Met Gln Gln Pro Val Asn Tyr Pro Cys Pro Gln Ile Tyr Trp Val Asp
1               5                   10                  15

Ser Ser Ala Thr Ser Pro Trp Ala Pro Pro Gly Ser Val Phe Ser Cys
            20                  25                  30

Pro Ser Ser Gly Pro Arg Gly Pro Gly Gln Arg Arg Pro Pro Pro Pro
        35                  40                  45

Pro Pro Pro Ser Pro Leu Pro Pro Ser Gln Pro Pro Leu
    50                  55                  60

Pro Pro Leu Ser Pro Leu Lys Lys Asp Asn Ile Glu Leu Trp Leu
65                  70                  75                  80

Pro Val Ile Phe Phe Met Val Leu Val Ala Leu Val Gly Met Gly Leu
                85                  90                  95

Gly Met Tyr Gln Leu Phe His Leu Gln Lys Glu Leu Ala Glu Leu Arg
            100                 105                 110

Glu Phe Thr Asn His Ser Leu Arg Val Ser Ser Phe Glu Lys Gln Ile
        115                 120                 125

Ala Asn Pro Ser Thr Pro Ser Glu Thr Lys Lys Pro Arg Ser Val Ala
    130                 135                 140

His Leu Thr Gly Asn Pro Arg Ser Arg Ser Ile Pro Leu Glu Trp Glu
145                 150                 155                 160

Asp Thr Tyr Gly Thr Ala Leu Ile Ser Gly Val Lys Tyr Lys Lys Gly
                165                 170                 175

Gly Leu Val Ile Asn Glu Ala Gly Leu Tyr Phe Val Tyr Ser Lys Val
            180                 185                 190

Tyr Phe Arg Gly Gln Ser Cys Asn Ser Gln Pro Leu Ser His Lys Val
        195                 200                 205

Tyr Met Arg Asn Phe Lys Tyr Pro Gly Asp Leu Val Leu Met Glu Glu
    210                 215                 220

Lys Lys Leu Asn Tyr Cys Thr Thr Gly Gln Ile Trp Ala His Ser Ser
225                 230                 235                 240

Tyr Leu Gly Ala Val Phe Asn Leu Thr Val Ala Asp His Leu Tyr Val
                245                 250                 255

Asn Ile Ser Gln Leu Ser Leu Ile Asn Phe Glu Glu Ser Lys Thr Phe
            260                 265                 270

Phe Gly Leu Tyr Lys Leu
        275

<210> SEQ ID NO 7
<211> LENGTH: 235
<212> TYPE: PRT
<213> ORGANISM: Homo sapiens

<400> SEQUENCE: 7

Met Ser Thr Glu Ser Met Ile Arg Asp Val Glu Leu Ala Glu Gly Pro
1               5                   10                  15

Leu Pro Lys Lys Ala Gly Gly Pro Gln Gly Ser Lys Arg Cys Leu Cys
            20                  25                  30

Leu Ser Leu Phe Ser Phe Leu Leu Val Ala Gly Ala Thr Thr Leu Phe

```
            35                  40                  45
    Cys Leu Leu His Phe Arg Val Ile Gly Pro Gln Glu Glu Gln Ser
         50                  55                  60
    Pro Asn Asn Leu His Leu Val Asn Pro Val Ala Gln Met Val Thr Leu
     65                  70                  75                  80
    Arg Ser Ala Ser Arg Ala Leu Ser Asp Lys Pro Leu Ala His Val Val
                     85                  90                  95
    Ala Asn Pro Gln Val Glu Gly Gln Leu Gln Trp Leu Ser Gln Arg Ala
                100                 105                 110
    Asn Ala Leu Leu Ala Asn Gly Met Lys Leu Thr Asp Asn Gln Leu Val
                115                 120                 125
    Val Pro Ala Asp Gly Leu Tyr Leu Ile Tyr Ser Gln Val Leu Phe Ser
    130                 135                 140
    Gly Gln Gly Cys Arg Ser Tyr Val Leu Leu Thr His Thr Val Ser Arg
    145                 150                 155                 160
    Phe Ala Val Ser Tyr Pro Asn Lys Val Asn Leu Leu Ser Ala Ile Lys
                    165                 170                 175
    Ser Pro Cys His Arg Glu Thr Pro Glu Glu Ala Glu Pro Met Ala Trp
                180                 185                 190
    Tyr Glu Pro Ile Tyr Leu Gly Gly Val Phe Gln Leu Glu Lys Gly Asp
                195                 200                 205
    Arg Leu Ser Thr Glu Val Asn Gln Pro Glu Tyr Leu Asp Leu Ala Glu
            210                 215                 220
    Ser Gly Gln Val Tyr Phe Gly Ile Ile Ala Leu
    225                 230                 235

<210> SEQ ID NO 8
<211> LENGTH: 434
<212> TYPE: DNA
<213> ORGANISM: Homo sapiens
<220> FEATURE:
<221> NAME/KEY: misc_feature
<222> LOCATION: (15)
<223> OTHER INFORMATION: n equals to a, t, g, or c
<221> NAME/KEY: misc_feature
<222> LOCATION: (19)
<223> OTHER INFORMATION: n equals to a, t, g, or c
<221> NAME/KEY: misc_feature
<222> LOCATION: (133)
<223> OTHER INFORMATION: n equals to a, t, g, or c
<221> NAME/KEY: misc_feature
<222> LOCATION: (388)
<223> OTHER INFORMATION: n equals to a, t, g, or c
<221> NAME/KEY: misc_feature
<222> LOCATION: (424)
<223> OTHER INFORMATION: n equals to a, t, g, or c

<400> SEQUENCE: 8
tctacacaag gtacngacng ctaccctgag ccaacccagc tcctcatggg gaccaagtct    60
gtatgcgaag taggtagcaa ctggttccag cccatctacc tcggagccat gttctccttg   120
caagaagggg acnagctaat ggtgaacgtc agtgacatct ctttggtgga ttacacaaaa   180
gaagataaaa ccttctttgg agccttctta ctataggagg agagcaaata tcattatatg   240
aaagtcctct gccaccgagt tcctaatttt ctttgttcaa atgtaattat aaccaggggt   300
tttcttgggg ccgggagtag ggggcattcc cacagggaca acggtttagc tatgaaattt   360
gggggggccca aaatttcaca acttcatngt tgcccttact tgatgagaag tacttaactt   420
gganaaaagg cttg                                                     434
```

```
<210> SEQ ID NO 9
<211> LENGTH: 493
<212> TYPE: DNA
<213> ORGANISM: Homo sapiens
<220> FEATURE:
<221> NAME/KEY: misc_feature
<222> LOCATION: (288)
<223> OTHER INFORMATION: n equals to a, t, g, or c
<221> NAME/KEY: misc_feature
<222> LOCATION: (296)
<223> OTHER INFORMATION: n equals to a, t, g, or c
<221> NAME/KEY: misc_feature
<222> LOCATION: (309)
<223> OTHER INFORMATION: n equals to a, t, g, or c
<221> NAME/KEY: misc_feature
<222> LOCATION: (314)
<223> OTHER INFORMATION: n equals to a, t, g, or c
<221> NAME/KEY: misc_feature
<222> LOCATION: (340)
<223> OTHER INFORMATION: n equals to a, t, g, or c
<221> NAME/KEY: misc_feature
<222> LOCATION: (343)
<223> OTHER INFORMATION: n equals to a, t, g, or c
<221> NAME/KEY: misc_feature
<222> LOCATION: (348)
<223> OTHER INFORMATION: n equals to a, t, g, or c
<221> NAME/KEY: misc_feature
<222> LOCATION: (369)
<223> OTHER INFORMATION: n equals to a, t, g, or c
<221> NAME/KEY: misc_feature
<222> LOCATION: (385)
<223> OTHER INFORMATION: n equals to a, t, g, or c
<221> NAME/KEY: misc_feature
<222> LOCATION: (410)
<223> OTHER INFORMATION: n equals to a, t, g, or c
<221> NAME/KEY: misc_feature
<222> LOCATION: (417)
<223> OTHER INFORMATION: n equals to a, t, g, or c
<221> NAME/KEY: misc_feature
<222> LOCATION: (423)
<223> OTHER INFORMATION: n equals to a, t, g, or c
<221> NAME/KEY: misc_feature
<222> LOCATION: (431)
<223> OTHER INFORMATION: n equals to a, t, g, or c
<221> NAME/KEY: misc_feature
<222> LOCATION: (434)
<223> OTHER INFORMATION: n equals to a, t, g, or c
<221> NAME/KEY: misc_feature
<222> LOCATION: (437)
<223> OTHER INFORMATION: n equals to a, t, g, or c
<221> NAME/KEY: misc_feature
<222> LOCATION: (444)
<223> OTHER INFORMATION: n equals to a, t, g, or c
<221> NAME/KEY: misc_feature
<222> LOCATION: (459)
<223> OTHER INFORMATION: n equals to a, t, g, or c
<221> NAME/KEY: misc_feature
<222> LOCATION: (486)
<223> OTHER INFORMATION: n equals to a, t, g, or c

<400> SEQUENCE: 9
aattcggcag agaaattcca tactatcacc agttggccaa ctttccaagt ctagtgcaga      60
aatccaaggc acctcacacc tagagttcct atacctctga gactccagag gaaagaacaa    120
gacagtgcag aaggatatgt tagaacccac tgaaaaccta gaaggttaaa aaggaagcat    180
accctcctga cctataagaa aatttcagt ctgcaggggg atatccttgt ggcccaagac     240
attggtgtta tcatttgact aagaggaaat tatttgtggt gagctccnag tgaggnttag    300
ggaccaggng gtgnccaagt ttctatcact tacctcatgn ctntaagnca agtgttttgt    360
tcccattgnt gatggggtta aaacnttcag ccatcacttt tggggcaagn atgggntttt    420 ganggggttgg ngcnggncttt gtcntcgtaa acaggggnt tggtgggttt ttctgggtcc   480
ttgggnagga ctt                                                      493
```

<210> SEQ ID NO 10
<211> LENGTH: 380
<212> TYPE: DNA
<213> ORGANISM: Homo sapiens
<220> FEATURE:
<221> NAME/KEY: misc_feature
<222> LOCATION: (53)..(54)
<223> OTHER INFORMATION: n equals to a, t, g, or c
<221> NAME/KEY: misc_feature
<222> LOCATION: (258)
<223> OTHER INFORMATION: n equals to a, t, g, or c
<221> NAME/KEY: misc_feature
<222> LOCATION: (316)
<223> OTHER INFORMATION: n equals to a, t, g, or c
<221> NAME/KEY: misc_feature
<222> LOCATION: (324)
<223> OTHER INFORMATION: n equals to a, t, g, or c
<221> NAME/KEY: misc_feature
<222> LOCATION: (346)
<223> OTHER INFORMATION: n equals to a, t, g, or c
<221> NAME/KEY: misc_feature
<222> LOCATION: (367)
<223> OTHER INFORMATION: n equals to a, t, g, or c
<221> NAME/KEY: misc_feature
<222> LOCATION: (378)
<223> OTHER INFORMATION: n equals to a, t, g, or c

<400> SEQUENCE: 10
ggcagaggtt caatttgatc ataaatttgc ttcaattcag gagctttgaa ggnngtccaa      60
ggaaagctct agaaaacagt ataaactttc agaggcaaaa tccttcacca attttttccac   120 atactttcat gccttgccta aaaaaaatga aaagagagtt ggtatgtctc atggaatgtt   180
cacacagaag gagttggttt tcatgtcatc tacagcatat gagaaaagct acctttcttt   240
tgattatgta cacaggtntc taaataagga agtatgagtt tcacatgtat attcaaaaat   300
acaacagttg cttgtnttca gttngggttt ttcttggccc acccanttt ggtgctgggg   360 gttctanctt taaccccnga                                                380

<210> SEQ ID NO 11
<211> LENGTH: 458
<212> TYPE: DNA
<213> ORGANISM: Homo sapiens
<220> FEATURE:
<221> NAME/KEY: misc_feature
<222> LOCATION: (9)
<223> OTHER INFORMATION: n equals to a, t, g, or c
<221> NAME/KEY: misc_feature
<222> LOCATION: (12)
<223> OTHER INFORMATION: n equals to a, t, g, or c
<221> NAME/KEY: misc_feature
<222> LOCATION: (119)
<223> OTHER INFORMATION: n equals to a, t, g, or c
<221> NAME/KEY: misc_feature
<222> LOCATION: (303)
<223> OTHER INFORMATION: n equals to a, t, g, or c
<221> NAME/KEY: misc_feature
<222> LOCATION: (311)
<223> OTHER INFORMATION: n equals to a, t, g, or c
<221> NAME/KEY: misc_feature
<222> LOCATION: (387)
<223> OTHER INFORMATION: n equals to a, t, g, or c
<221> NAME/KEY: misc_feature
<222> LOCATION: (409)
<223> OTHER INFORMATION: n equals to a, t, g, or c
<221> NAME/KEY: misc_feature
<222> LOCATION: (425)
<223> OTHER INFORMATION: n equals to a, t, g, or c
<221> NAME/KEY: misc_feature
<222> LOCATION: (427)
<223> OTHER INFORMATION: n equals to a, t, g, or c
<221> NAME/KEY: misc_feature
<222> LOCATION: (453)
<223> OTHER INFORMATION: n equals to a, t, g, or c

<400> SEQUENCE: 11
ggcacagcng gnagtagggg gcattccaca gggacaacgg tttagctatg aaatttgggg     60
cccaaaattt cacacttcat gtgccttact gatgagagta ctaactggaa aaaggctgna    120
agagagcaaa tatattatta agatgggttg gaggattggc gagtttctaa atattaagac    180
actggatcac tgaaatgaat ggatgatcta ctcgggtcca ggattgaaag agaaatattt    240
caacaccttc ctgctataca atggtcacca gtggtccagt tattgttcca atttggatcc    300
atnaatttgc nttcaattcc aggagctttg gaaggaattc caaggaaagc tccaggaaaa    360
ccgtattaaa ctttccaggg gccaaantcc ttcaccaatt ttttccacna actttccagg    420
cctgncncaa aaaaatggaa agggagttgg tangtccc                            458

<210> SEQ ID NO 12
<211> LENGTH: 388
<212> TYPE: DNA
<213> ORGANISM: Homo sapiens
<220> FEATURE:
<221> NAME/KEY: misc_feature
<222> LOCATION: (11)..(12)
<223> OTHER INFORMATION: n equals to a, t, g, or c
<221> NAME/KEY: misc_feature
<222> LOCATION: (46)
<223> OTHER INFORMATION: n equals to a, t, g, or c
<221> NAME/KEY: misc_feature
<222> LOCATION: (50)
<223> OTHER INFORMATION: n equals to a, t, g, or c
<221> NAME/KEY: misc_feature
<222> LOCATION: (81)
<223> OTHER INFORMATION: n equals to a, t, g, or c
<221> NAME/KEY: misc_feature
<222> LOCATION: (138)
<223> OTHER INFORMATION: n equals to a, t, g, or c
<221> NAME/KEY: misc_feature
<222> LOCATION: (155)
<223> OTHER INFORMATION: n equals to a, t, g, or c
<221> NAME/KEY: misc_feature
<222> LOCATION: (182)
<223> OTHER INFORMATION: n equals to a, t, g, or c
<221> NAME/KEY: misc_feature
<222> LOCATION: (188)
<223> OTHER INFORMATION: n equals to a, t, g, or c
<221> NAME/KEY: misc_feature
<222> LOCATION: (269)
<223> OTHER INFORMATION: n equals to a, t, g, or c
<221> NAME/KEY: misc_feature
<222> LOCATION: (317)
<223> OTHER INFORMATION: n equals to a, t, g, or c
<221> NAME/KEY: misc_feature
<222> LOCATION: (322)
<223> OTHER INFORMATION: n equals to a, t, g, or c
<221> NAME/KEY: misc_difference
<222> LOCATION: (358)
<223> OTHER INFORMATION: n equals to a, t, g, or c
<221> NAME/KEY: misc_feature
<222> LOCATION: (363)
<223> OTHER INFORMATION: n equals to a, t, g, or c
<221> NAME/KEY: misc_feature
<222> LOCATION: (375)
<223> OTHER INFORMATION: n equals to a, t, g, or c

<400> SEQUENCE: 12
ctgcactggg nncatgaact aggcctggcc ttcaccaaga accgantgan ctataccaac     60
aaattcctgc tgatcccaga ntcgggagac tacttcattt actcccaggt cacattccgt    120
gggaatgaac ctctgaantg ccagtgaaaa tcagncaagc aggccgacca aacaagccag    180
antccatnca ctgtggtcat caccaaggta acagacagct accctgagcc aacccagctc    240

```
cttcatggggg accaagttttg tttgcgaant aggttagcaa ctggttccag cccattttac      300
cttgggggcc agttctnctt gncaagaagg ggacaagctt atggtggaac gttcatanca      360
tcntttttgg gtggntttac acaaaagg                                         388
```

<210> SEQ ID NO 13
<211> LENGTH: 37
<212> TYPE: DNA
<213> ORGANISM: Homo sapiens

<400> SEQUENCE: 13

```
gcgcggatcc accatgagac gcttttttaag caaagtc                               37
```

<210> SEQ ID NO 14
<211> LENGTH: 36
<212> TYPE: DNA
<213> ORGANISM: Homo sapiens

<400> SEQUENCE: 14

```
cgcgtctaga ctatagtaag aaggctccaa agaagg                                36
```

<210> SEQ ID NO 15
<211> LENGTH: 37
<212> TYPE: DNA
<213> ORGANISM: Homo sapiens

<400> SEQUENCE: 15

```
gcgcggatcc accatgagac gcttttttaag caaagtc                               37
```

<210> SEQ ID NO 16
<211> LENGTH: 36
<212> TYPE: DNA
<213> ORGANISM: Homo sapiens

<400> SEQUENCE: 16

```
cgcgtctaga ctatagtaag aaggctccaa agaagg                                36
```

<210> SEQ ID NO 17
<211> LENGTH: 56
<212> TYPE: DNA
<213> ORGANISM: Homo sapiens

<400> SEQUENCE: 17

```
cgctctagat caagcgtagt ctgggacgtc gtatggatag taagaaggct ccaaag           56
```

<210> SEQ ID NO 18
<211> LENGTH: 733
<212> TYPE: DNA
<213> ORGANISM: Homo sapiens

<400> SEQUENCE: 18

```
gggatccgga gcccaaatct tctgacaaaa ctcacacatg cccaccgtgc ccagcacctg       60
aattcgaggt gcaccgtca gtcttcctct tccccccaaa acccaaggac accctcatga       120
tctcccggac tcctgaggtc acatgcgtgg tggtggacgt aagccacgaa gaccctgagg      180
tcaagttcaa ctggtacgtg gacggcgtgg aggtgcataa tgccaagaca aagccgcggg      240
aggagcagta acaacagcacg taccgtgtgg tcagcgtcct caccgtcctg caccaggact    300
ggctgaatgg caaggagtac aagtgcaagg tctccaacaa agccctccca acccccatcg     360
agaaaaccat ctccaaagcc aaagggcagc cccgagaacc acaggtgtac accctgcccc    420
```

```
catcccggga tgagctgacc aagaaccagg tcagcctgac ctgcctggtc aaaggcttct    480
atccaagcga catcgccgtg gagtgggaga gcaatgggca gccggagaac aactacaaga    540
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg cgacggccgc    720
gactctagag gat                                                      733
```

<210> SEQ ID NO 19
<211> LENGTH: 1116
<212> TYPE: DNA
<213> ORGANISM: Homo sapiens

<400> SEQUENCE: 19

```
atggccgagg atctgggact gagctttggg gaaacagcca gtgtggaaat gctgccagag     60
cacggcagct gcaggcccaa ggccaggagc agcagcgcac gctgggctct cacctgctgc    120
ctggtgttgc tcccttcct  tgcaggactc accacatacc tgcttgtcag ccagctccgg    180
gcccagggag aggcctgtgt gcagttccag gctctaaaag acaggagtt  tgcaccttca    240 catcagcaag tttatgcacc tcttagagca gacggagata agccaagggc acacctgaca    300
gttgtgagac aaactcccac acagcacttt aaaaatcagt tcccagctct gcactgggaa    360
catgaactag gcctggcctt caccaagaac cgaatgaact ataccaacaa attcctgctg    420
atcccagagt cggagactac cttcatttac tcccaggtca cattccgtgg gatgacctct    480
gagtgcagtg aaatcagaca agcaggccga ccaaacaagc cagactccat cactgtggtc    540
atcaccaagg taacagacag ctaccctgag ccaacccagc tcctcatggg gaccaagtct    600
gtatgcgaag taggtagcaa ctggttccag cccatctacc tcggagccat gttctccttg    660
caagaagggg acaagctaat ggtgaacgtc agtgacatct ctttggtgga ttacacaaaa    720
gaagataaaa ccttctttgg agccttctta ctataggagg agagcaaata tcattatatg    780
aaagtcctct gccaccgagt tcctaatttt ctttgttcaa atgtaattat aaccaggggt    840
tttcttgggg ccgggagtag gggcattcca cagggacaac ggtttagcta tgaaatttgg    900
ggcccaaaat ttcacacttc atgtgcctta ctgatgagag tactaactgg aaaaaggctg    960
aagagagcaa atatattatt aagatggggtt ggaggattgg cgagtttcta atattaaga   1020 cactgatcac taaatgaatg gatgatctac tcgggtcagg attgaaagag aaatatttca   1080
acaccttcct gctatacaat ggtcaccagt ggtcca                             1116
```

<210> SEQ ID NO 20
<211> LENGTH: 251
<212> TYPE: PRT
<213> ORGANISM: Homo sapiens

<400> SEQUENCE: 20

```
Met Ala Glu Asp Leu Gly Leu Ser Phe Gly Glu Thr Ala Ser Val Glu
  1               5                  10                  15

Met Leu Pro Glu His Gly Ser Cys Arg Pro Lys Ala Arg Ser Ser Ser
                 20                  25                  30

Ala Arg Trp Ala Leu Thr Cys Cys Leu Val Leu Leu Pro Phe Leu Ala
             35                  40                  45

Gly Leu Thr Thr Tyr Leu Leu Val Ser Gln Leu Arg Ala Gln Gly Glu
         50                  55                  60

Ala Cys Val Gln Phe Gln Ala Leu Lys Gly Gln Glu Phe Ala Pro Ser
```

```
                65                  70                  75                  80
His Gln Gln Val Tyr Ala Pro Leu Arg Ala Asp Gly Asp Lys Pro Arg
                        85                  90                  95
Ala His Leu Thr Val Val Arg Gln Thr Pro Thr Gln His Phe Lys Asn
                100                 105                 110
Gln Phe Pro Ala Leu His Trp Glu His Glu Leu Gly Leu Ala Phe Thr
            115                 120                 125
Lys Asn Arg Met Asn Tyr Thr Asn Lys Phe Leu Leu Ile Pro Glu Ser
130                 135                 140
Gly Asp Tyr Phe Ile Tyr Ser Gln Val Thr Phe Arg Gly Met Thr Ser
145                 150                 155                 160
Glu Cys Ser Glu Ile Arg Gln Ala Gly Arg Pro Asn Lys Pro Asp Ser
                165                 170                 175
Ile Thr Val Val Ile Thr Lys Val Thr Asp Ser Tyr Pro Glu Pro Thr
            180                 185                 190
Gln Leu Leu Met Gly Thr Lys Ser Val Cys Glu Val Gly Ser Asn Trp
        195                 200                 205
Phe Gln Pro Ile Tyr Leu Gly Ala Met Phe Ser Leu Gln Glu Gly Asp
    210                 215                 220
Lys Leu Met Val Asn Val Ser Asp Ile Ser Leu Val Asp Tyr Thr Lys
225                 230                 235                 240
Glu Asp Lys Thr Phe Phe Gly Ala Phe Leu Leu
                245                 250

<210> SEQ ID NO 21
<211> LENGTH: 434
<212> TYPE: DNA
<213> ORGANISM: Homo sapiens
<220> FEATURE:
<221> NAME/KEY: misc_feature
<222> LOCATION: (15)
<223> OTHER INFORMATION: n equals to a, t, g, or c
<221> NAME/KEY: misc_feature
<222> LOCATION: (19)
<223> OTHER INFORMATION: n equals to a, t, g, or c
<221> NAME/KEY: misc_feature
<222> LOCATION: (133)
<223> OTHER INFORMATION: n equals to a, t, g, or c
<221> NAME/KEY: misc_feature
<222> LOCATION: (388)
<223> OTHER INFORMATION: n equals to a, t, g, or c
<221> NAME/KEY: misc_feature
<222> LOCATION: (424)
<223> OTHER INFORMATION: n equals to a, t, g, or c

<400> SEQUENCE: 21
tctacacaag gtacngacng ctaccctgag ccaacccagc tcctcatggg gaccaagtct      60
gtatgcgaag taggtagcaa ctggttccag cccatctacc tcggagccat gttctccttg     120
caagaagggg acnagctaat ggtgaacgtc agtgacatct ctttggtgga ttacacaaaa     180
gaagataaaa ccttctttgg agccttctta ctataggagg agagcaaata tcattatatg     240
aaagtcctct gccaccgagt tcctaatttt ctttgttcaa atgtaattat aaccaggggt     300
tttcttgggg ccgggagtag ggggcattcc cacagggaca acggtttagc tatgaaattt     360
ggggggccca aaatttcaca acttcatngt tgcccttact tgatgagaag tacttaactt     420
gganaaaagg cttg                                                      434

<210> SEQ ID NO 22
<211> LENGTH: 417
<212> TYPE: DNA
```

```
<213> ORGANISM: Homo sapiens
<220> FEATURE:
<221> NAME/KEY: misc_feature
<222> LOCATION: (4)
<223> OTHER INFORMATION: n equals to a, t, g, or c
<221> NAME/KEY: misc_feature
<222> LOCATION: (8)
<223> OTHER INFORMATION: n equals to a, t, g, or c
<221> NAME/KEY: misc_feature
<222> LOCATION: (17)
<223> OTHER INFORMATION: n equals to a, t, g, or c
<221> NAME/KEY: misc_feature
<222> LOCATION: (24)
<223> OTHER INFORMATION: n equals to a, t, g, or c
<221> NAME/KEY: misc_feature
<222> LOCATION: (28)
<223> OTHER INFORMATION: n equals to a, t, g, or c
<221> NAME/KEY: misc_feature
<222> LOCATION: (31)..(32)
<223> OTHER INFORMATION: n equals to a, t, g, or c
<221> NAME/KEY: misc_feature
<222> LOCATION: (35)
<223> OTHER INFORMATION: n equals to a, t, g, or c
<221> NAME/KEY: misc_feature
<222> LOCATION: (41)..(43)
<223> OTHER INFORMATION: n equals to a, t, g, or c
<221> NAME/KEY: misc_feature
<222> LOCATION: (46)
<223> OTHER INFORMATION: n equals to a, t, g, or c
<221> NAME/KEY: misc_feature
<222> LOCATION: (48)
<223> OTHER INFORMATION: n equals to a, t, g, or c
<221> NAME/KEY: misc_feature
<222> LOCATION: (50)
<223> OTHER INFORMATION: n equals to a, t, g, or c
<221> NAME/KEY: misc_feature
<222> LOCATION: (53)
<223> OTHER INFORMATION: n equals to a, t, g, or c
<221> NAME/KEY: misc_feature
<222> LOCATION: (55)
<223> OTHER INFORMATION: n equals to a, t, g, or c
<221> NAME/KEY: misc_feature
<222> LOCATION: (61)..(63)
<223> OTHER INFORMATION: n equals to a, t, g, or c
<221> NAME/KEY: misc_feature
<222> LOCATION: (66)..(67)
<223> OTHER INFORMATION: n equals to a, t, g, or c
<221> NAME/KEY: misc_feature
<222> LOCATION: (202)
<223> OTHER INFORMATION: n equals to a, t, g, or c
<221> NAME/KEY: misc_feature
<222> LOCATION: (209)
<223> OTHER INFORMATION: n equals to a, t, g, or c
<221> NAME/KEY: misc_feature
<222> LOCATION: (282)
<223> OTHER INFORMATION: n equals to a, t, g, or c
<221> NAME/KEY: misc_feature
<222> LOCATION: (306)
<223> OTHER INFORMATION: n equals to a, t, g, or c
<221> NAME/KEY: misc_feature
<222> LOCATION: (321)
<223> OTHER INFORMATION: n equals to a, t, g, or c
<221> NAME/KEY: misc_feature
<222> LOCATION: (344)
<223> OTHER INFORMATION: n equals to a, t, g, or c
<221> NAME/KEY: misc_feature
<222> LOCATION: (346)
<223> OTHER INFORMATION: n equals to a, t, g, or c
<221> NAME/KEY: misc_feature
<222> LOCATION: (380)..(381)
<223> OTHER INFORMATION: n equals to a, t, g, or c
<221> NAME/KEY: misc_feature
<222> LOCATION: (395)
<223> OTHER INFORMATION: n equals to a, t, g, or c
<221> NAME/KEY: misc_feature
<222> LOCATION: (405)
<223> OTHER INFORMATION: n equals to a, t, g, or c

<400> SEQUENCE: 22
```

```
attncggnac gagcagnggc atgnccgngg nnctnggact nnnctntngn gananagcca    60
nnnttnnaat gctgccagag cacggcagct gcaggcccaa ggccaggagc agcagcgcac   120
gctgggctct cacctgctgc ctggtgttgc tccccttcct tgcaggactc accacatacc   180
tgcttgtcag ccagcttcgg gnccagggng aggcctgtgt gcagttccag ggtctaaaag   240
gacaggagtt tgcaccttca catcagcaag tttatgcacc tnttagagca gacggagata   300
agccangggg acaactgaca nttgtgagac aaattccaca cagnanttta aaatcagttt   360
ccagttttga atggggacan nattaggctg gcttnacaag accgntggat tttacag      417
```

<210> SEQ ID NO 23
<211> LENGTH: 388
<212> TYPE: DNA
<213> ORGANISM: Homo sapiens
<220> FEATURE:
<221> NAME/KEY: misc_feature
<222> LOCATION: (11)..(12)
<223> OTHER INFORMATION: n equals to a, t, g, or c
<221> NAME/KEY: misc_feature
<222> LOCATION: (46)
<223> OTHER INFORMATION: n equals to a, t, g, or c
<221> NAME/KEY: misc_feature
<222> LOCATION: (50)
<223> OTHER INFORMATION: n equals to a, t, g, or c
<221> NAME/KEY: misc_feature
<222> LOCATION: (81)
<223> OTHER INFORMATION: n equals to a, t, g, or c
<221> NAME/KEY: misc_feature
<222> LOCATION: (138)
<223> OTHER INFORMATION: n equals to a, t, g, or c
<221> NAME/KEY: misc_feature
<222> LOCATION: (155)
<223> OTHER INFORMATION: n equals to a, t, g, or c
<221> NAME/KEY: misc_feature
<222> LOCATION: (182)
<223> OTHER INFORMATION: n equals to a, t, g, or c
<221> NAME/KEY: misc_feature
<222> LOCATION: (188)
<223> OTHER INFORMATION: n equals to a, t, g, or c
<221> NAME/KEY: misc_feature
<222> LOCATION: (269)
<223> OTHER INFORMATION: n equals to a, t, g, or c
<221> NAME/KEY: misc_feature
<222> LOCATION: (317)
<223> OTHER INFORMATION: n equals to a, t, g, or c
<221> NAME/KEY: misc_feature
<222> LOCATION: (322)
<223> OTHER INFORMATION: n equals to a, t, g, or c
<221> NAME/KEY: misc_feature
<222> LOCATION: (358)
<223> OTHER INFORMATION: n equals to a, t, g, or c
<221> NAME/KEY: misc_feature
<222> LOCATION: (363)
<223> OTHER INFORMATION: n equals to a, t, g, or c
<221> NAME/KEY: misc_feature
<222> LOCATION: (375)
<223> OTHER INFORMATION: n equals to a, t, g, or c

<400> SEQUENCE: 23

```
ctgcactggg nncatgaact aggcctggcc ttcaccaaga accgantgan ctataccaac    60
aaattcctgc tgatcccaga ntcgggagac tacttcattt actcccaggt cacattccgt   120
gggaatgaac ctctgaantg ccagtgaaaa tcagncaagc aggccgacca aacaagccag   180
antccatnca ctgtggtcat caccaaggta acagacagct accctgagcc aacccagctc   240
cttcatgggg accaagtttg tttgcgaant aggttagcaa ctggttccag cccatttac    300 cttgggggcc agttctnctt gncaagaagg ggacaagctt atggtggaac gttcatanca   360 tcnttttttgg gtggnttac acaaaagg                                      388
```

```
<210> SEQ ID NO 24
<211> LENGTH: 458
<212> TYPE: DNA
<213> ORGANISM: Homo sapiens
<220> FEATURE:
<221> NAME/KEY: misc_feature
<222> LOCATION: (9)
<223> OTHER INFORMATION: n equals to a, t, g, or c
<221> NAME/KEY: misc_feature
<222> LOCATION: (12)
<223> OTHER INFORMATION: n equals to a, t, g, or c
<221> NAME/KEY: misc_feature
<222> LOCATION: (119)
<223> OTHER INFORMATION: n equals to a, t, g, or c
<221> NAME/KEY: misc_feature
<222> LOCATION: (303)
<223> OTHER INFORMATION: n equals to a, t, g, or c
<221> NAME/KEY: misc_feature
<222> LOCATION: (311)
<223> OTHER INFORMATION: n equals to a, t, g, or c
<221> NAME/KEY: misc_feature
<222> LOCATION: (387)
<223> OTHER INFORMATION: n equals to a, t, g, or c
<221> NAME/KEY: misc_feature
<222> LOCATION: (409)
<223> OTHER INFORMATION: n equals to a, t, g, or c
<221> NAME/KEY: misc_feature
<222> LOCATION: (425)
<223> OTHER INFORMATION: n equals to a, t, g, or c
<221> NAME/KEY: misc_feature
<222> LOCATION: (427)
<223> OTHER INFORMATION: n equals to a, t, g, or c
<221> NAME/KEY: misc_feature
<222> LOCATION: (453)
<223> OTHER INFORMATION: n equals to a, t, g, or c

<400> SEQUENCE: 24
ggcacagcng gnagtagggg gcattccaca gggacaacgg tttagctatg aaatttgggg      60
cccaaaattt cacacttcat gtgccttact gatgagagta ctaactggaa aaaggctgna    120
agagagcaaa tatattatta agatgggttg gaggattggc gagtttctaa atattaagac    180
actggatcac tgaaatgaat ggatgatcta ctcgggtcca ggattgaaag agaaatattt    240
caacaccttc ctgctataca atggtcacca gtggtccagt tattgttcca atttggatcc    300
atnaatttgc nttcaattcc aggagctttg gaaggaattc caaggaaagc tccaggaaaa    360
ccgtattaaa ctttccaggg gccaaantcc ttcaccaatt ttttccacna actttccagg    420
cctgncncaa aaaaatggaa agggagttgg tangtccc                           458
```

NUCLEIC ACID MOLECULES ENCODING TUMOR NECROSIS FACTOR-GAMMA-ALPHA

This application claims benefit under 35 U.S.C. §119(e) of the filing date of copending U.S. Provisional Application Serial No. 60/074,047, filed on Feb. 9, 1998. Further, this application claims benefit under 35 U.S.C. §120 as a continuation-in-part of U.S. application Ser. No. 09/005,020, filed on Jan. 9, 1998, which is a continuation-in-part of U.S. application Ser. No. 08/461,246, filed on Jun. 5, 1995, which is a continuation-in-part of International Application Serial No. PCT/US94/12880, filed on Nov. 7, 1994. Each of the four aforementioned applications are hereby incorporated by reference in their entireties.

FIELD OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptide of the present invention has been identified as a new member of the tumor necrosis factor family and is hereinafter referred to as "TNF-gamma-alpha". The invention also relates to a protein encoded by a splice variant of the gene encoding TNF-gamma-alpha which is hereinafter referred to as "TNF-gamma-beta". The invention also relates to inhibiting the action of such polypeptides.

BACKGROUND OF THE INVENTION

Human tumor necrosis factors-α (TNF-α) and β (TNF-β or lymphotoxin) are related members of a broad class of polypeptide mediators, which includes the interferons, interleukins and growth factors, collectively called cytokines (Beutler, B. and Cerami, A., Annu. Rev. Immunol., 7:625–655 (1989)).

Tumor necrosis factor (TNF-α and TNF-β) was originally discovered as a result of its anti-tumor activity, however, now it is recognized as a pleiotropic cytokine playing important roles in immune regulation and inflammation. To date, there are eight known members of the TNF-related cytokine family, TNF-α, TNF-β (lymphotoxin (LT)-α), LT-β, and ligands for the Fas, CD30, CD27, CD40 and 4-1BB receptors. These proteins have conserved C-terminal sequences and variable N-terminal sequences which are often used as membrane anchors, with the exception of TNF-β. Both TNF-α and TNF-β function as homotrimers when they bind to TNF receptors.

TNF is produced by a number of cell types, including monocytes, fibroblasts, T-cells, natural killer (NK) cells and predominately by activated machrophages. TNF-α has been reported to have a role in the rapid necrosis of tumors, immunostimulation, autoimmune disease, graft rejection, resistance to parasites, producing an anti-viral response, septic shock, growth regulation, vascular endothelium effects and metabolic effects. TNF-α also triggers endothelial cells to secrete various factors, including PAI-1, IL-1, GM-CSF and IL-6 to promote cell proliferation. In addition, TNF-α up-regulates various cell adhesion molecules such as E-Selectin, ICAM-1 and VCAM-1. TNF-α and Fas ligand have also been shown to induce programmed cell death.

The first step in the induction of the various cellular responses mediated by TNF or LT is their binding to specific cell surface receptors. Two distinct TNF receptors of approximately 55-KDa (TNF-R1) and 75-KDa (TNF-R2) have been identified (Hohman, H. P. et al., J. Biol. Chem., 264:14927–14934 (1989)), and human and mouse cDNAs corresponding to both receptor types have been isolated and characterized (Loetscher, H. et al., Cell, 61:351 (1990)). Both TNF-Rs share the typical structure of cell surface receptors including extracellular, transmembrane and intracellular regions.

The endothelium, which under physiological conditions is mostly a quiescent tissue (Denekamp, J. Cancer Metas. Rev. 9:267–282 (1990)), plays an essential role in the maintenance of vascular homeostasis and permeability. Endothelial cells are actively involved in inflammation, cell adhesion, coagulation, thrombosis, fibrinolysis, and angiogenesis. During angiogenesis, endothelial cells proliferate, invade into stroma, migrate toward the source of an angiogenesis stimulus, such as cancer cells, interact with perivascular cells and stromal cells, and eventually, form capillary vessels linking the tumor tissue to the circulatory system (Folkman, J. Nature Med. 1:27–31 (1995)). Although the complex mechansim that regulates angiogenesis is yet to be fully understood, it is becoming clear that the initiation or termination of the process is a result of a balance between positive and negative factors.

A number of angiogenic factors, often markedly upregulated in tumor tissues, have been described. These include several members of the fibroblast growth factor (FGF) family, such as FGF-1, FGF-2, and those of the vascular endothelial cell growth factor (VEGF) family and the receptors for all of these molecules (Gimenez-Gallego, G, et al., Science 230:1385–1388 (1985); Schweigerer, L., et al., Nature 325:257–259 (1987); Leung, D. W., et al., Science 246:1306–1309 (1989); Bunrus, L. W. and Olwin, B. B. J. Biol. Chem. 264:18647–18653 (1989); Wennstrom, S., et al., Growth Factors 4:197–208 (1991); Terman, B. I., et al., Biochem. Biophys. Res. Comm. 187:1579–1586 (1992); de Vries, C., et al., Science 255:989–991 (1992)). Likewise, several inhibitors of angiogenesis have also been reported, including thrombospondin, angiostatin, endostatin, and platelet factor-4 (Good, D. J., et al., Proc. Natl. Acad. Sci. USA 87:6623–6628 (1990); O'Reilly, M. S., et al., Cell 79:315–328 (1994); O'Reilly, M. S., et al., Cell 88:277–285 (1997); Maione, T. E., et al., Science 247:77–79 (1990)). It is apparent that normal angiogenesis is promptly activated when needed, and swiftly terminated when no longer required. However, pathological angiogenesis, once initiated, is often prolonged and often difficult to stop. This may indicate that a negative regulatory mechanism normally functioning is missing or suppressed in a pathological angiogenic process. It is conceivable that endothelial cells may produce autocrine factors to suppress an angiogenesis process or maintain the quiescence of a mature vasculature.

The polypeptide of the present invention has been identified as a novel member of the TNF family based on structural, amino acid sequence homology, and functional similarities, for example, TNF-gamma is a pro-inflammatory protein. Further, the TNF-gamma polypeptide of the present invention is a negative regulator of angiogenesis and of endothelial cell growth. There is a need for polypeptides that function in this manner, since disturbances of such regulation may be involved in disorders relating to angiogenesis, hemostasis, tumor metastisis, cellular migration, and cancers of many systems. Therefore, there is a need for identification and characterization of such human polypeptides which can play a role in detecting, preventing, ameliorating or correcting such disorders.

SUMMARY OF THE INVENTION

In accordance with one aspect of the present invention, there is provided a novel mature polypeptide which is TNF-gamma-alpha, and a novel mature polypeptide which is TNF-gamma-beta, as well as biologically active and diagnostically or therapeutically useful fragments, analogs and derivatives thereof.

In accordance with another aspect of the present invention, there are provided isolated nucleic acid molecules encoding human TNF-gamma-alpha or TNF-gamma-beta, including mRNAs, DNAs, cDNAs, genomic DNAs as well as analogs and biologically active and diagnostically or therapeutically useful fragments and derivatives thereof.

The present invention provides isolated nucleic acid molecules comprising a polynucleotide encoding at least a portion of the TNF-gamma-alpha polypeptide having the complete amino acid sequence shown in SEQ ID NO:2 or the complete amino acid sequence encoded by the cDNA clone HUVEO91 deposited as plasmid DNA as ATCC Deposit Number 75927 on Oct. 26, 1994. The nucleotide sequence determined by sequencing the deposited TNF-gamma-alpha clone, which is shown in FIGS. 1A and 1B (SEQ ID NO:1), contains an open reading frame encoding a complete polypeptide of 174 amino acid residues, including an initiation codon encoding an N-terminal methionine at nucleotide positions 783–785, and a predicted molecular weight of about 20,132 Da.

The present invention also provides isolated nucleic acid molecules comprising a polynucleotide encoding at least a portion of the TNF-gamma-beta polypeptide having the complete amino acid sequence shown in SEQ ID NO:20 or the complete amino acid sequence encoded by the cDNA clone HEMCZ56 deposited as plasmid DNA as ATCC Deposit Number 203055 on Jul. 9, 1998. The nucleotide sequence determined by sequencing the deposited TNF-gamma-beta clone, which is shown in FIGS. 20A and B (SEQ ID NO:20), contains an open reading frame encoding a complete polypeptide of 251 amino acid residues, including an initiation codon encoding an N-terminal methionine at nucleotide positions 1–3, and a predicted molecular weight of about 28,089 Da.

Thus, in one embodiment the invention provides an isolated nucleic acid molecule comprising a polynucleotide having a nucleotide sequence selected from the group consisting of: (a) a nucleotide sequence encoding the TNF-gamma-alpha polypeptide having the complete amino acid sequence in SEQ ID NO:2 (i.e., positions −27 to 147 of SEQ ID NO:2, (b) a nucleotide sequence encoding the TNF-gamma-alpha polypeptide having the complete amino acid sequence in SEQ ID NO:2 excepting the N-terminal methionine (i.e., positions −26 to 147 of SEQ ID NO:2); (c) a nucleotide sequence encoding the mature TNF-gamma-alpha polypeptide having the amino acid sequence in SEQ ID NO:2 shown as positions 1 to 147 of SEQ ID NO:2; (d) a nucleotide sequence encoding the TNF-gamma-alpha polypeptide having the complete amino acid sequence encoded by the cDNA clone HUVEO91 contained in ATCC Deposit No. 75927; (e) a nucleotide sequence encoding the TNF-gamma-alpha polypeptide having the complete amino acid sequence excepting the N-terminal methionine encoded by the cDNA clone HUVEO91 contained in ATCC Deposit No. 75927; (f) a nucleotide sequence encoding the mature TNF-gamma-alpha polypeptide having the amino acid sequence encoded by the cDNA clone HUVEO91 contained in ATCC Deposit No. 75927; and (g) a nucleotide sequence complementary to any of the nucleotide sequences in (a), (b), (c), (d), (e) or (f), above.

In another embodiment, the invention provides an isolated nucleic acid molecule comprising a polynucleotide having a nucleotide sequence selected from the group consisting of: (a) a nucleotide sequence encoding the TNF-gamma-beta polypeptide having the complete amino acid sequence in SEQ ID NO:20 (i.e., positions 1 to 251 of SEQ ID NO:20); (b) a nucleotide sequence encoding the TNF-gamma-beta polypeptide having the complete amino acid sequence in SEQ ID NO:20 excepting the N-terminal methionine (i.e., positions 2 to 251 of SEQ ID NO:20); (c) a nucleotide sequence encoding the mature TNF-gamma-beta polypeptide having the amino acid sequence in SEQ ID NO:20 shown as positions 62 to 251 of SEQ ID NO:20; (d) a nucleotide sequence encoding the TNF-gamma-beta polypeptide having the complete amino acid encoded by the cDNA clone HEMCZ56 contained in ATCC Deposit No. 203055; (e) a nucleotide sequence encoding the TNF-gamma-alpha polypeptide having the complete amino acid sequence excepting the N-terminal methionine encoded by the cDNA clone HEMCZ56 contained in ATCC Deposit No. 203055; (f) a nucleotide sequence encoding the mature TNF-gamma-beta polypeptide having the amino acid sequence encoded by the cDNA clone HEMCZ56 contained in ATCC Deposit No. 203055; and (g) a nucleotide sequence complementary to any of the nucleotide sequences in (a), (b), (c), (d), (e) or (f), above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d), (e), (f) or (g), above, or a polynucleotide which hybridizes under stringent hybridization conditions to a polynucleotide in (a), (b), (c), (d), (e), (f) or (g), above, a fragment thereof (such as, for example, fragments described herein), or the complementary strand thereto. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion (i.e., a fragment) of a TNF-gamma polypeptide having an amino acid sequence in (a), (b), (c), (d), (e) or (f), above. A further embodiment of the invention relates to an isolated nucleic acid molecule comprising a polynucleotide which encodes the amino acid sequence of a TNF-gamma polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference it is highly preferable for a polynucleotide which encodes the amino acid sequence of a TNF-gamma polypeptide to have an amino acid sequence which contains not more than 10, 9, 8, 7, 6, 5, 4, 3, 2 or 1 amino acid substitutions. Conservative substitutions are preferable.

The present invention also relates to recombinant vectors, which include the isolated nucleic acid molecules of the present invention, and to host cells containing the recombinant vectors, as well as to methods of making such vectors and host cells and for using them for production of TNF-gamma polypeptides or peptides by recombinant techniques.

In accordance with a further aspect of the present invention, there is provided a process for producing such polypeptide by recombinant techniques comprising culturing recombinant prokaryotic and/or eukaryotic host cells, containing a human TNF-gamma nucleic acid sequence, under conditions promoting expression of said protein and subsequent recovery of said protein.

The invention further provides an isolated TNF-gamma polypeptide comprising an amino acid sequence selected from the group consisting of: (a) the amino acid sequence of the full-length TNF-gamma-alpha polypeptide having the complete amino acid sequence shown in SEQ ID NO:2 (i.e., positions −27 to 147 of SEQ ID NO:2); (b) the amino acid sequence of the full-length TNF-gamma-alpha polypeptide having the complete amino acid sequence shown in SEQ ID NO:2 excepting the N-terminal methionine (i.e., positions −26 to 147 of SEQ ID NO:2); (c) the amino acid sequence of the predicted mature TNF-gamma-alpha polypeptide having the amino acid sequence at positions 1–147 in SEQ ID NO:2; (d) the complete amino acid sequence encoded by the cDNA clone HUVEO91 contained in the ATCC Deposit No. 75927; (e) the complete amino acid sequence excepting the N-terminal methionine encoded by the cDNA clone HUVEO91 contained in the ATCC Deposit No. 75927; (f) the complete amino acid sequence of the predicted mature TNF-gamma polypeptide encoded by the cDNA clone HUVEO91 contained in the ATCC Deposit No. 75927; and (g) fragments of the polypeptide of (a), (b), (c), (d), (e), or (f). The polypeptides of the present invention also include polypeptides having an amino acid sequence at least 80% identical, more preferably at least 90% identical, and still more preferably 95%, 96%, 97%, 98% or 99% identical to those described in (a), (b), (c), (d), (e) (f), or (g) above, as well as polypeptides having an amino acid sequence with at least 90% similarity, and more preferably at least 95% similarity, to those above. Additional embodiments of the invention relates to a polypeptide which comprises the amino acid sequence of an epitope-bearing portion of a TNF-gamma polypeptide having an amino acid sequence described in (a), (b), (c), (d), (e), (f), or (g) above. Peptides or polypeptides having the amino acid sequence of an epitope-bearing portion of a TNF-gamma polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

The invention further provides an isolated TNF-gamma polypeptide comprising an amino acid sequence selected from the group consisting of: (a) the amino acid sequence of the full-length TNF-gamma-beta polypeptide having the complete amino acid sequence shown in SEQ ID NO:20 (i.e., positions 1 to 251 of SEQ ID NO:20); (b) the amino acid sequence of the full-length TNF-gamma-beta polypeptide having the complete amino acid sequence shown in SEQ ID NO:20 excepting the N-terminal methionine (i.e., positions 2 to 251 of SEQ ID NO:20); (c) the amino acid sequence of the predicted mature TNF-gamma-beta polypeptide having the amino acid sequence at positions 62–251 in SEQ ID NO:20; (d) the complete amino acid sequence encoded by the cDNA clone HEMCZ56 contained in the ATCC Deposit No. 203055; (e) the complete amino acid sequence excepting the N-terminal methionine encoded by the cDNA clone HEMCZ56 contained in the ATCC Deposit No. 203055; (f) the complete amino acid sequence of the predicted mature TNF-gamma polypeptide encoded by the cDNA clone contained in the ATCC Deposit No. 203055; and (g) fragments of the polypeptide of (a), (b), (c), (d), (e), or (f). The polypeptides of the present invention also include polypeptides having an amino acid sequence at least 80% identical, more preferably at least 90% identical, and still more preferably 95%, 96%, 97%, 98% or 99% identical to those described in (a), (b), (c), (d), (e) (f), or (g) above, as well as polypeptides having an amino acid sequence with at least 90% similarity, and more preferably at least 95% similarity, to those above. Additional embodiments of the invention relates to a polypeptide which comprises the amino acid sequence of an epitope-bearing portion of a TNF-gamma polypeptide having an amino acid sequence described in (a), (b), (c), (d), (e), (f), or (g) above. Peptides or polypeptides having the amino acid sequence of an epitope-bearing portion of a TNF-gamma polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

A further embodiment of the invention relates to a polypeptide which comprises the amino acid sequence of a TNF-gamma polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of a TNF-gamma polypeptide, which contains at least one, but not more than 10, 9, 8, 7, 6, 5, 4, 3, 2 or 1 amino acid substitutions. In specific embodiments, the number of additions, substitutions, and/or deletions in the amino acid sequence of FIGS. 1A and 1B, FIGS. 20A amd B. or fragments thereof (e.g., the extracellular domain and/or other fragments described herein), is 1–5, 5–10, 5–25, 5–50, 10–50 or 50–150, conservative amino acid substitutions are preferable.

In another embodiment, the invention provides an isolated antibody that binds specifically to a TNF-gamma polypeptide having an amino acid sequence described above. The invention further provides methods for isolating antibodies that bind specifically to a TNF-gamma polypeptide having an amino acid sequence as described herein. Such antibodies are useful diagnostically or therapeutically as described below.

In accordance with yet a further aspect of the present invention, there is provided a process for utilizing polynucleotides and/or polypeptides of the invention to screen for agonists and antagonists, and for therapeutic purposes, which include, but are not limited to, wound healing, to inhibit tumor proliferation, to provide resistance to parasites, bacteria and viruses, to induce inflammatory activities, to induce proliferation of endothelial cells and certain hematopoietic cells, to treat restenosis and to prevent certain autoimmune diseases.

In accordance with yet a further aspect of the present invention, there are also provided nucleic acid probes comprising nucleic acid molecules of sufficient length to specifically hybridize to human TNF-gamma sequences.

In accordance with another aspect of the present invention, there are provided TNF-gamma agonists which mimic TNF-gamma and binds to the TNF-gamma receptors to elicit TNF-gamma type responses.

In accordance with yet another aspect of the present invention, there are provided antagonists to such polypeptides, which may be used to inhibit the action of such polypeptides, for example, to prevent septic shock, inflammation, cerebral malaria, activation of the HIV virus, graft rejection, bone resorption and cachexia.

In accordance with still another aspect of the present invention, there are provided diagnostic assays for detecting diseases related to the under-expression and over-expression of the TNF-gamma polypeptide and nucleic acid sequences encoding such polypeptide.

In a further aspect of the invention, TNF-gamma may be used to treat rheumatoid arthritis (RA) by inhibiting the increase in angiogensis or the increase in endothelial cell proliferation required to sustain an invading pannus in bone and cartilage as is often observed in RA.

In yet another aspect, the TNF-gamma may bind to a cell surface protein which also functions as a viral receptor or coreceptor. Thus, TNF-gamma or agonists or antagonists thereof, may be used to regulate viral infectivity at the level of viral binding or interaction with the TNF-gamma receptor or coreceptor or during the process of viral internalization or entry into the cell.

In accordance with all aspects of the invention, the term "TNF-gamma" refers to TNF-gamma-alpha and/or TNF-gamma-beta.

These and other aspects of the present invention should be apparent to those skilled in the art from the teachings herein.

BRIEF DESCRIPTION OF THE FIGURES

The following drawings are illustrative of embodiments of the invention and are not meant to limit the scope of the invention as encompassed by the claims.

FIGS. 1A and 1B illustrate the cDNA (SEQ ID NO:1) and corresponding deduced amino acid sequence (SEQ ID NO:2) of the polypeptide of TNF-gamma-alpha of the present invention. The initial 27 amino acids (underlined) are the putative leader sequence. The standard one-letter abbreviations for amino acids are used. Potential asparagine-linked glycosylation sites are marked in FIGS. 1A and 1B with a bolded asparagine symbol (N) in the TNF-gamma-alpha amino acid sequence and a bolded pound sign (#) above the first nucleotide encoding that asparagine residue in the TNF-gamma-alpha nucleotide sequence. Potential N-linked glycosylation sequences are found at the following locations in the TNF-gamma-alpha amino acid sequence: N-29 through N-32 (N-29, Y-30, T-31, N-32) and N-125 through D-128 (N-125, V-126, S-127, D-128). Potential Protein Kinase C (PKC) phosphorylation sites are also marked in FIGS. 1A and 1B with a bolded threonine symbol (T) in the TNF-gamma-alpha amino acid sequence and an asterisk (*) above the first nucleotide encoding that threonine residue in the TNF-gamma-alpha nucleotide sequence. Potential PKC phosphorylation sequences are found at the following locations in the TNF-gamma-alpha amino acid sequence: T-32 through K-34 (T-32, N-33, K-34) and T-50 through R-52 (T-50, F-51, R-52). Potential Casein Kinase II (CK2) phosphorylation sites are also marked in FIGS. 1A and 1B with a bolded serine or threonine symbol (S or T) in the TNF-gamma-alpha amino acid sequence and an asterisk (*) above the first nucleotide encoding the appropriate serine or threonine residue in the TNF-gamma-alpha nucleotide sequence. Potential CK2 phosphorylation sequences are found at the following locations in the TNF-gamma-alpha amino acid sequence: S-83 through E-86 (S-83, Y-84, P-85, E-86); S-96 through E-99 (S-96, V-97, C-98, E-99); S-115 through E-118 (S-115, L-116, Q-117, E-118); S-130 through D-133 (S-130, L-131; V-132, D-133); and T-135 through D-138 (T-135, K-136, E-137, D-138). Potential myristylation sites are also marked in FIGS. 1A and 1B with a double underline in the TNF-gamma-alpha amino acid sequence. Potential myristylation sequences are found at the following locations in the TNF-gamma-alpha amino acid sequence: G-20 through K-25 (G-20, L-21, A-22, F-23, T-24. K-25) and G-111 through L-116 (G-111, A-112, M-113, F-114, S-115, L-116).

Figure 2A:
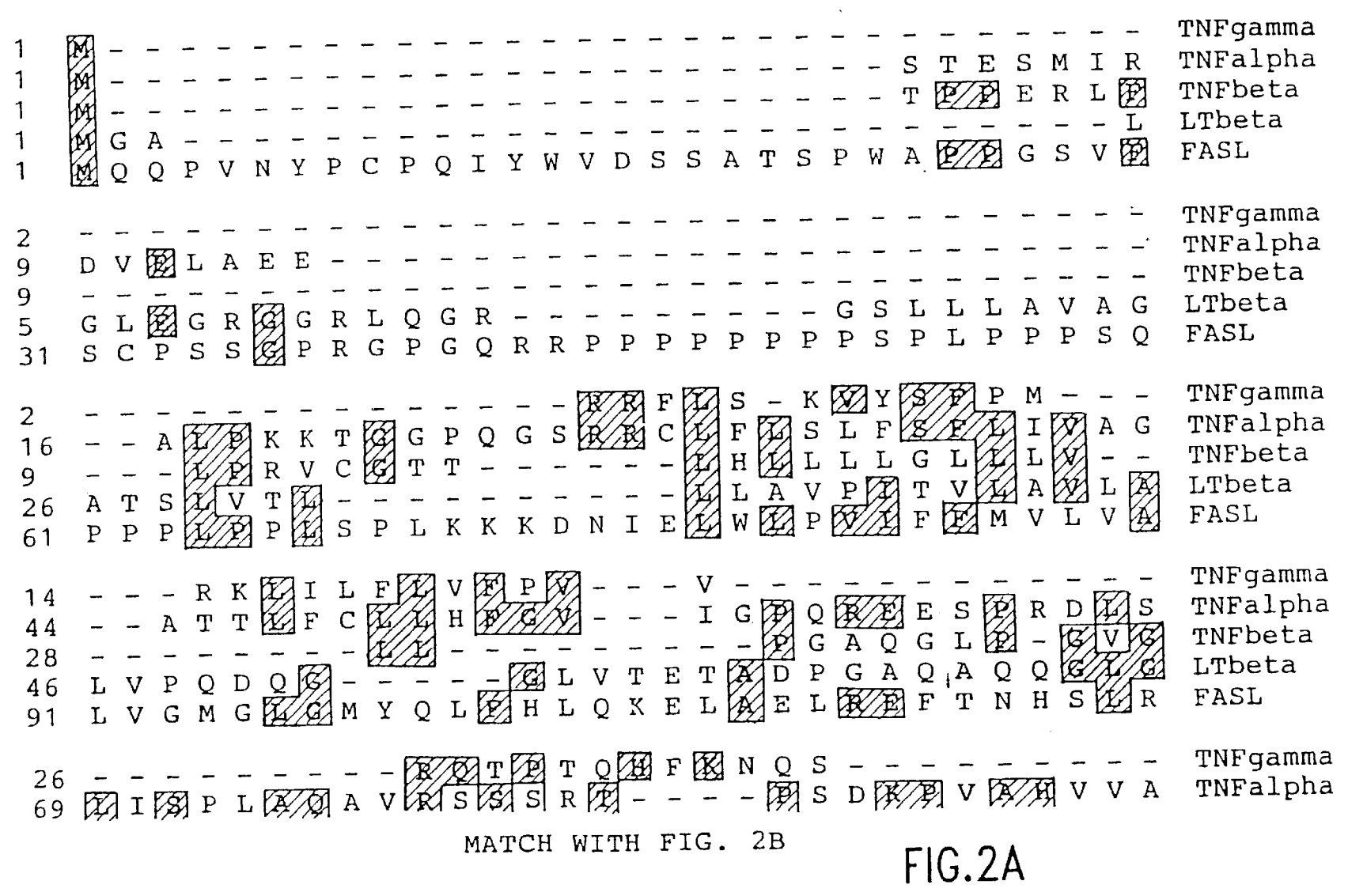
Figure 2B:
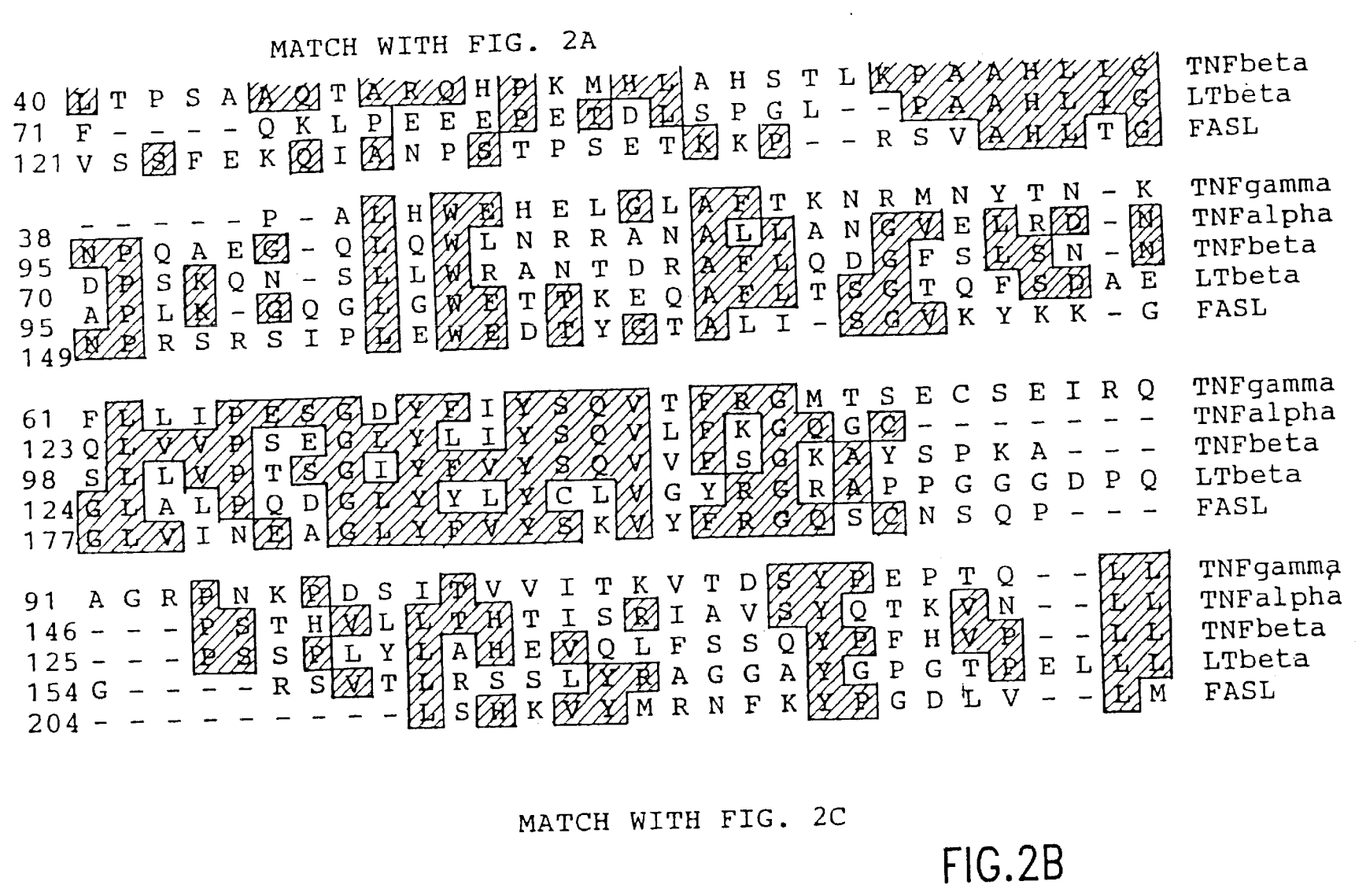
Figure 2C:
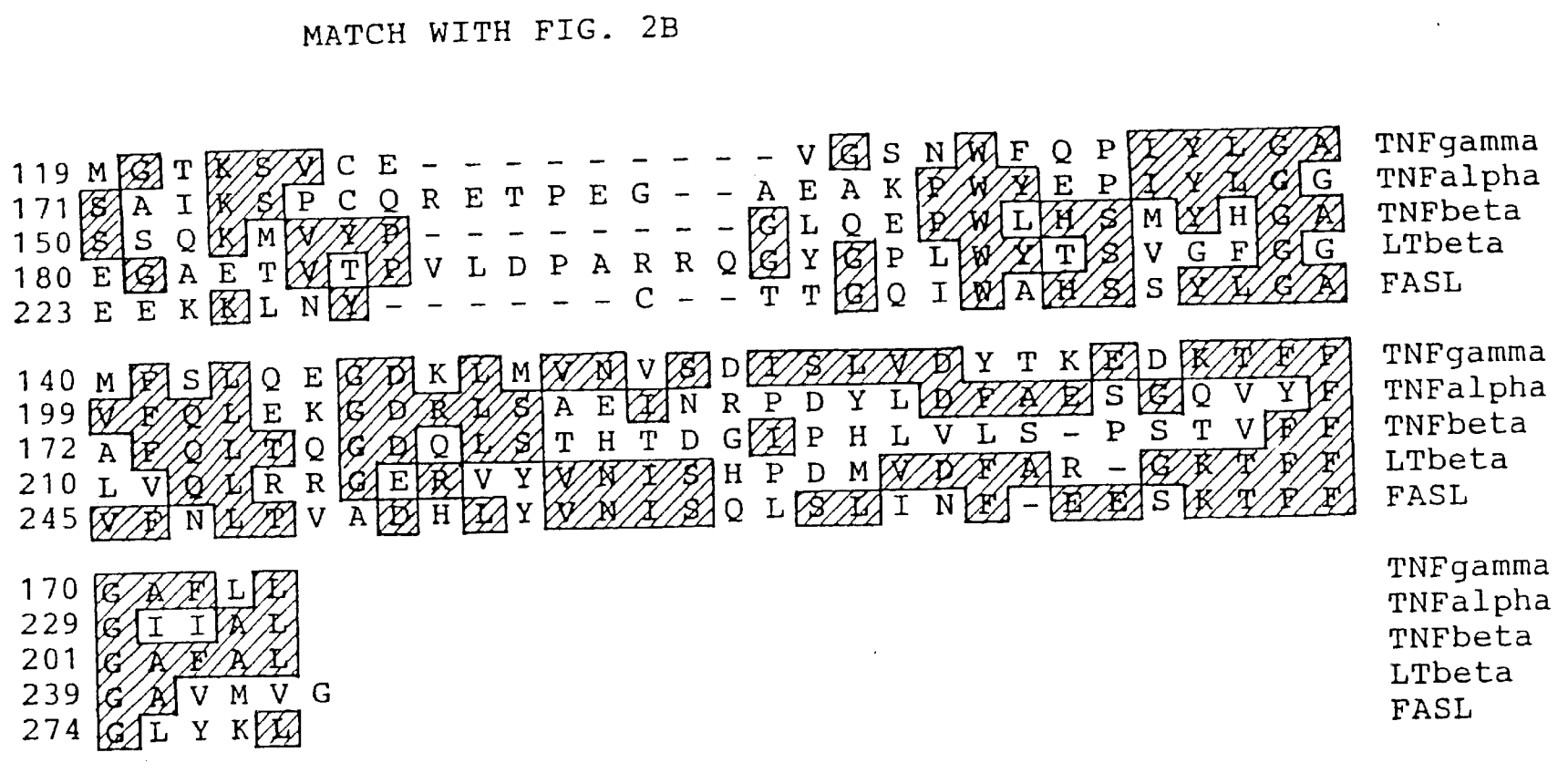

FIGS. 2A–C illustrate an amino acid sequence alignment between TNF-gamma-alpha (SEQ ID NO:2) and other members of the TNF family including human TNF-alpha (GenBank No. Z15026; SEQ ID NO:3), human TNF-beta (GenBank No. Z15026; SEQ ID NO:4), human lymphotoxin-beta (LTbeta; GenBank No. L11016; SEQ ID NO:5), and rat Fas Ligand (FASL: GenBank No. NM_012908; SEQ ID NO:6). TNF-gamma contains the conserved amino acid residues of the TNF family as shown by the boxed and shaded areas. The aligned molecules are presented in their entirety as FIGS. 2A, 2B, and 2C.

FIG. 3A shows a distinct band. Other lanes seem to show strong hybridization, however, these are actually non-specific smears.

FIG. 4 illustrates the relative expression of TNF-gamma in proliferating or quiescent endothelial cells. The TNF-gamma mRNA levels in cultured HUVEC cells were determined by Northern blotting analysis. Identical amounts of total RNA (15 $\mu$g) were loaded on each lane, as indicated by the intensity of β-actin. The signal which corresponds to TNF-gamma is designated "VEGI". Total RNA was prepared at the indicated time point (days post-seeding). The number of cells in each culture flask was determined simultaneously. The experiment was carried out in duplicate. Cells were seeded at 125,00 cells per flask (T-25).

FIG. 6 is a photograph of a gel showing the relative purity and mobility of baculovirus-expressed TNF-gamma. The expression and purification of TNF-gamma using the baculovirus system is described in Example 2.

FIGS. 18A–D show an alignment of the nucleotide sequences of TNF-gamma-alpha (SEQ ID NO:1) and TNF-gamma-beta (SEQ ID NO:19) constructed by using the computer program BESTFIT set at default paramters.

FIG. 19 shows an alignment of the amino acid sequences of TNF-gamma-alpha (SEQ ID NO:2) and TNF-gamma-beta (SEQ ID NO:20) constructed using the default parameters of the computer program BESTFIT.

FIGS. 20A and B illustrate the cDNA (SEQ ID NO:19) and corresponding deduced amino acid sequence (SEQ ID NO:20) of the polypeptide of the TNF-gamma-beta of the present invention. The standard one-letter abbreviations for amino acids are used. Amino acids methionine-1 to tryptophan-35 are the predicted intracellular domain. Amino acid residues alanine-36 through alanine-61 (underlined) are the putative transmembrane sequence. Amino acid residues glutamine-62 through leucine-251 (underlined) are the putative transmembrane sequence. Potential asparagine-linked glycosylation sites are marked in FIGS. 20A and B with a bolded asparagine symbol (N) in the TNF-gamma-beta amino acid sequence and a bolded pound sign (#) above the first nucleotide encoding that asparagine residue in the TNF-gamma-alpha nucleotide sequence. Potential N-linked glycosylation sequences are found at the following locations in the TNF-gamma-beta amino acid sequence: N-133 through N-136 (N-133, Y-134, T-135, N-136) and N-229 through D-232 (N-229, V-230, S-231, D-232). Potential Protein Kinase C (PKC) phosphorylation sites are also marked in FIGS. 20A and B with a bolded serine or threonine symbol (S or T) in the TNF-gamma-beta amino acid sequence and an asterisk (*) above the first nucleotide encoding that threonine residue in the TNF-gamma-beta nucleotide sequence. Potential PKC phosphorylation sequences are found at the following locations in the TNF-gamma-beta amino acid sequence: S-23 through R-25 (S-23, C-24, R-25); S-32 through R-34 (S-32, A-33, R-34); T-135 through K-137 (T-135, N-136, K-137); and T-154 through R-156 (T-154, F-155, R-156). Potential Casein Kinase II (CK2) phosphorylation sites are also marked in FIGS. 20A and B with a bolded serine or threonine symbol (S or T) in the TNF-gamma-beta amino acid sequence and an asterisk (*) above the first nucleotide encoding the appropriate serine or threonine residue in the TNF-gamma-beta nucleotide sequence. Potential CK2 phosphorylation sequences are found at the following locations in the TNF-gamma-beta amino acid sequence: S-8 through E-11 (S-8, F-9, G-10, E-11); S-187 through E-190 (S-187, Y-188, P-189, E-190); S-200 through E-203 (S-200, V-201, C-202, E-203); S-219 through E-222 (S-219, L-220, Q-221, E-222); S-234 through D-237 (S-234, L-235, V-236, D-237); and T-239 through D-242 (T-239, K-240, E-241, D-242). Potential myristylation sites are also marked in FIGS. 20A and B with a double underline in the TNF-gamma-beta amino acid sequence. Potential myristylation sequences are found at the following locations in the TNF-gamma-beta amino acid sequence: G-6 through E-11 (G-6, L-7, S-8, F-9, G-10, E-11); G-124 through G-129 (G-124, L-125, A-126, F-127, T-128, K-129); and G-215 through L-220 (G-215, A-216, M-217, F-218, S-219, L-220).

DETAILED DESCRIPTION

The present invention provides isolated nucleic acid molecules comprising a polynucleotide encoding a TNF-gamma-alpha polypeptide having the amino acid sequence shown in FIGS. 1A and B (SEQ ID NO:2), which was determined by sequencing a cloned cDNA (HUVE091). As shown in FIGS. 2A–2C, the TNF-alpha polypeptide of the present invention shares sequence homology with human TNF-alpha (SEQ ID NO:3), TNF-beta (SEQ ID NO:4), human lymphotoxin-beta (SEQ ID NO:5) and FAS ligand (SEQ ID NO:6). The TNF-gamma-alpha of the invention functions at least in the inhibition of angiogenesis, as an anti-tumor cytokine-like molecule, as a treatment for arthritiis by the inhibition of angiogenesis and/or endothelial cell proliferation associated with invading pannus in bone and cartilage, as an inducer of NF-kB and c-Jun kinase (JNK), an inducer of cell adhsion, and as an inducer apoptosis (See Examples, particularly Examples 12–15). The nucleotide sequence shown in SEQ ID NO:1 was obtained by sequencing a cDNA clone (HUVE091), which was deposited on Oct. 26, 1994 at the American Type Culture Collection, 10801 University Boulevard Manassas, Va. 20110-2209 and given accession number 75927. The deposited plasmid is contained in pBluescript SK(−) plasmid (Stratagene, La Jolla, Calif.). Further characterization of the protein encoded by clone HUVEO91 is presented in copending U.S. Provisional Application Serial No. 60/074,047, filed Feb. 9, 1998; the entire disclosure of which is hereby incorporated by reference.

The present invention also provides isolated nucleic acid molecules comprising a polynucleotide (SEQ ID NO:19) encoding a TNF-gamma-beta polypeptide having the amino acid sequence shown in FIGS. 20A and B (SEQ ID NO:20), which was determined by sequencing a cloned cDNA (HEMCZ56). The TNF-gamma-beta polypeptide is a splice variant of the TNF-gamma-alpha polypeptide disclosed herein. The nucleotide sequence shown in SEQ ID NO:19 was obtained by sequencing a cDNA clone (HEMCZ56), which was deposited on Jul. 9, 1998 at the American Type Culture Collection, 10801 University Boulevard, Manassas, Va. 20110-2209, and given accession number 203055. The deposited plasmid is contained in pBluescript SK(−) plasmid (Stratagene, La Jolla, Calif.).

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the nucleotide sequence in FIGS. 1A and B (SEQ ID NO:1), or the nucleotide sequence in FIGS. 20A and B (SEQ ID NO:19) a nucleic acid molecule (i.e., polynucleotide) of the present invention encoding a TNF-gamma-alpha or TNF-gamma-beta polypeptide may be obtained using standard cloning and screening procedures, such as, for example, those for cloning cDNAs using mRNA as the starting material. For example, polynucleotides encoding TNF-gamma-alpha polypeptides may routinely be obtained from any cell or tissue source that expresses TNF-gamma-alpha, such as, for example, human kidney and umbilical vein endothelial cells. Illustrative of the invention, the nucleic acid molecules described in FIGS. 1A and B (SEQ ID NO:1) was discovered in a cDNA library derived from human umbilical vein endothelial cells. The cDNA clone corresponding to TNF-gamma-alpha (clone HUVE091) contains an open reading frame encoding a protein of 174 amino acid residues of which approximately the first 27 amino acids residues are the putative leader sequence such that the mature protein comprises 147 amino acids. The protein exhibits the highest degree of homology at the C-terminus to Rabbit TNF-α (Ito, H., et al., *DNA* 5:157–165 (1986); GenBank Accession No. M12846; SEQ ID NO:7) with 38% identity and 58% similarity over a 111 amino acid stretch. Sequences conserved throughout the members of the TNF family are also conserved in TNF-gamma (see FIGS. 2A–2C). The shaded letters indicate conserved amino acid residues. The TNF-gamma mRNA is specifically expressed in human umbilical vein endothelial cells as shown in the RNA blot analysis of FIG. 3B.

Further, polynucleotides encoding a TNF-gamma-beta polypeptide may routinely be obtained from induced and resting endothelial cells, umbilical vein, tonsils, and several other cell and tissue types. Illustrative of the invention, the nucleic acid molecules described in FIGS. 20A and B (SEQ ID NO:19) was discovered in a cDNA library derived from induced endothelial cells. The cDNA clone corresponding to TNF-gamma-alpha (HEMCZ56) contains an open reading frame encoding a protein of 251 amino acid residues of

Figure 3A:
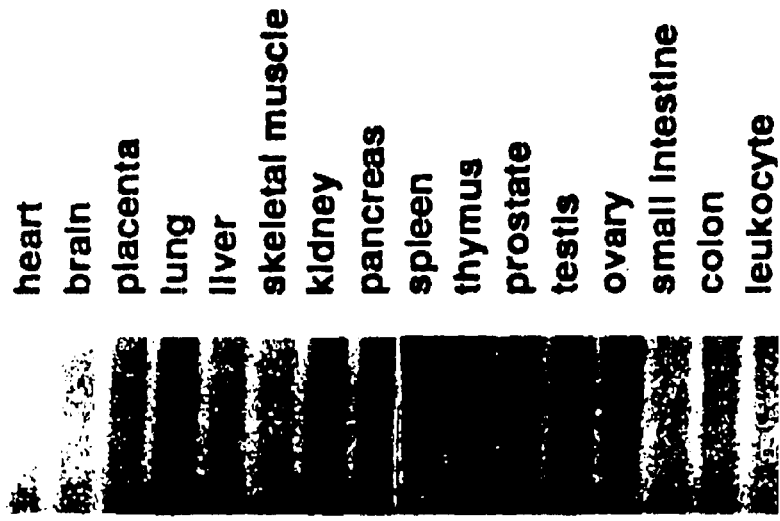
FIG. 3A is an RNA blot analysis showing the human tissues where TNF-gamma is expressed. RNA from the tissues indicated were probed with labeled TNF-gamma cDNA. TNF-gamma-alpha mRNA exists predominantly in the kidney since

which approximately the first 35 amino acids residues are the putative intracellular domain and amino acids 36–61 are a putative transmembrane domain and amino acid residues 62–251 are a putative extracellular domain.

The amino acid residues constituting the extracellular, transmembrane, and intracellular domains have been predicted by computer analysis. Thus, as one of ordinary skill would appreciated, the amino acid residues constituting these domains may vary slightly (e.g., by about 1 to about 15 amino acid residues) depending on the criteria used to define each domain.

In accordance with an aspect of the present invention, there is provided an isolated nucleic acid (polynucleotide) which encodes for the mature polypeptide having the deduced amino acid sequence of FIGS. 1A and B (SEQ ID NO:2), or for the mature polypeptide encoded by the cDNA of the clone designated HUVEO91 deposited as ATCC Deposit No. 75927 on Oct. 26, 1994.

In addition, in accordance with another aspect of the present invention, there is provided an isolated nucleic acid (polynucleotide) which encodes for the mature polypeptide having the deduced amino acid sequence of FIGS. 20A and B (SEQ ID NO:20), or for the mature polypeptide encoded by the cDNA of the clone designated HEMCZ56 deposited as ATCC Deposit No. 203055 on Jul. 9, 1998.

By "isolated" nucleic acid molecule(s) or polynucleotide is intended a molecule, DNA or RNA, which has been removed form its native environment. For example, recombinant DNA molecules (polynucleotides) contained in a vector are considered isolated for the purposes of the present invention. Furhther examples of isolated DNA molecules (polynucleotides) include recombinant DNA molecules maintained in heterologous host cells or purified (partially or substantially) DNA molecules in solution. Isolated RNA molecules (polynculeotides) include in vivo or in vitro RNA transcripts of the DNA molecules (polynucleotides) of the present invention. Isolated nucleic acid molecules or polynucleotides according to the present invention further include such molecules produced synthetically.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand.

Isolated nucleic acid molecules of the present invention include the polynucleotide sequence depicted in FIGS. 1A and B (SEQ ID NO:1) encoding the mature TNF-gamma-alpha polypeptide, the polynucleotide sequence depicted in FIGS. 20A and B (SEQ ID NO:19) encoding the mature TNF-gamma-beta polypeptide, the polynucleotide sequences contained in deposited clone (HUVE091) deposited as ATCC Deposit No. 75927 encoding the mature TNF-gamma-alpha polypeptide, the polynucleotide sequences contained in deposited clone (HEMCZ56) deposited as ATCC Deposit No. 203055 encoding the mature TNF-gamma-beta polypeptide, and polynucleoitde sequences which comprise a sequence different from those described above, but which due to the degeneracy of the genetic code, encodes the same mature polypeptide as the DNA of FIGS. 1A and B, FIGS. 20A and B, or the deposited cDNA. Of course, the genetic code is well known in the art. Thus, it would be routine for one skilled in the art to generate such degenerate variants.

The amino acid sequence of the complete TNF-gamma-alpha protein includes a leader sequence and a mature protein, as shown in FIGS. 1A and B (SEQ ID NO:2). More in particular, the present invention provides nucleic acid molecules encoding a mature form of the TNF-gamma-alpha protein. Thus, according to the signal hypothesis, once export of the growing protein chain across the rough endoplasmic reticulum has been initiated, proteins secreted by mammalian cells have a signal or secretory leader sequence which is cleaved from the complete polypeptide to produce a secreted "mature" form of the protein. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature TNF-gamma-alpha polypeptide having the amino acid sequence encoded by the cDNA clone contained in ATCC Deposit No. 75927. By the "mature TNF-gamma-alpha polypeptide having the amino acid sequence encoded by the cDNA clone in ATCC Deposit No. 75927" is meant the mature form(s) of the TNF-gamma-alpha protein produced by expression in a mammalian cell (e.g., COS cells, as described below) of the complete open reading frame encoded by the human DNA sequence of the deposited clone.

The polynucleotide which encodes for the mature polypeptide of FIGS. 20A and B or for the mature polypeptide encoded by the deposited cDNA (HEMCZ56) may include, but is not limited to: only the coding sequence for the mature polypeptide; the coding sequence for the mature polypeptide and additional coding sequence such as a leader or secretory sequence or a transmembrane sequence or a proprotein sequence; the coding sequence for the mature polypeptide (and optionally additional coding sequence) and non-coding sequence, such as introns or non-coding sequence 5' and/or 3' of the coding sequence for the mature polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments (i.e., portions), analogs and derivatives of the polypeptide having the deduced amino acid sequence of FIGS. 1A and B, FIGS. 20A and B, and the polypeptide encoded by the cDNA of the deposited clones. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A and B, or the mature polypeptide encoded by the cDNA of the deposited clone HUVEO91 as well as variants of such polynucleotides which variants encode for a fragment, derivative or analog of the polypeptide of FIGS. 1A and B, or the polypeptide encoded by the cDNA of the deposited clone HUVEO91. Such nucleotide variants include deletion variants, substitution variants and addition or insertion variants.

Additionally, the present invention includes polynucleotides encoding the mature polypeptide as shown in FIGS. 20A and B, or the mature polypeptide encoded by the cDNA of the deposited clone HEMCZ56 as well as variants of such polynucleotides which variants encode for a fragment, derivative or analog of the polypeptide of FIGS. 20A and B, or the polypeptide encoded by the cDNA of the deposited clone HEMCZ56. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A and 1B or of the coding sequence of the deposited clone HUVEO91. Alternatively, the polynucleotide may have a coding sequence which is a naturally occurring allelic variant of the coding sequence shown in FIGS. 20A and B or of the coding sequence of the deposited clone HEMCZ56. As known in the art, an allelic variant is an alternate form of a polynucleotide sequence which may have a substitution, deletion or addition of one or more nucleotides, which does not substantially alter the function of the encoded polypeptide.

The present invention is further directed to fragments of the isolated nucleic acid molecules described herein. By a fragment of an isolated nucleic acid molecule having the nucleotide sequence of the deposited cDNAs (HUVEO91 and HEMCZ56), or the nucleotide sequence shown in FIGS. 1A and B (SEQ ID NO:1), FIGS. 20A and B (SEQ ID NO:19), or the complementary strand thereto, is intended fragments at least 15 nt, and more preferably at least 20 nt, still more preferably at least 30 nt, and even more preferably, at least 40, 50, 100, 150, 200, 250, 300, 400, or 500 nt in length. These fragments have numerous uses which include, but are not limited to, diagnostic probes and primers as discussed herein. Of course, larger fragments 50–1500 nt in length are also useful according to the present invention as are fragments corresponding to most, if not all, of the nucleotide sequence of the deposited cDNA clone HUVEO91, the deposited cDNA clone HEMCZ56, the nucleotide sequence depicted in FIGS. 1A and B (SEQ ID NO:1), or the nucletoide sequence depicted in FIGS. 20A and B (SEQ ID NO 20). By a fragment at least 20 nt in length, for example, is intended fragments which include 20 or more contiguous bases from the nucleotide sequence of the deposited cDNA clones (HUVEO91 and HEMCZ56), the nucleotide sequence as shown in FIGS. 1A and B (SEQ ID NO:1), or the nucleotide sequence as shown in FIGS. 20A and B.

In specific embodiments, the polynucleotide fragments of the invention encode a polypeptide which demonstrates a functional activity. By a polypeptide demonstrating "functional activity" is meant, a polypeptide capable of displaying one or more known functional activities associated with a complete or mature TNF-gamma polypeptide. Such functional activities include, but are not limited to, biological activity ((e.g., inhibition of angiogenesis, inhibition of endothelial cell proliferation, induction of NF-kB and c-Jun kinase (JNK), induction of cell adhesion, and induction of apoptosis (See Examples, particularly Examples 12–15)), antigenicity [ability to bind (or compete with a TNF-gamma polypeptide for binding) to an anti-TNF-gamma antibody], immunogenicity (ability to generate antibody which binds to a TNF-gamma polypeptide), the ability to form polymers with other TNF-gamma polpeptides, and ability to bind to a receptor or ligand for a TNF-gamma polypeptide (e.g. DR3).

The invention also provides nucleic acid molecules having nucleotide sequences related to extensive fragments of SEQ ID NO:1 which have been determined from the following related cDNA clones: HUVEO91 (SEQ ID NO:8), HMPAP05 (SEQ ID NO:9), HSXCA44 (SEQ ID NO:10), HEMFG66 (SEQ ID NO:11), and HELAM93 (SEQ ID NO:12).

The invention also provides nucleic acid molecules having nucleotide sequences related to extensive fragments of SEQ ID NO:19 which have been determined from the following related cDNA clones: HUVEO91P01 (SEQ ID NO:21), HMPTI24R (SEQ ID NO:22), HELAM93R (SEQ ID NO:23), and HEMFG66R (SEQ ID NO:24).

In specific embodiments, the polynucleotide fragments of the invention comprise, or alternatively, consist of, a polynucleotide comprising any portion of at least 30 nucleotides, preferably at least 50 nucleotides, of SEQ ID NO:1 from nucleotide residue 1 to 2442, preferably excluding the nucleotide sequences determined from the abovelisted cDNA clones. Representative examples of the TNF-gamma-alpha polynucletoide fragments of the invention, include fragments that comprise, or alternativelty, consist of, nucleotides: 783–1304, 800–1300, 850–1300, 900–1300, 950–1300, 1000–1300, 1050–1300, 1100–1300, 1150–1300, 1200–1300, 1250–1300, 783–1250, 800–1250, 850–1250, 900–1250, 950–1250, 1000–1250, 1050–1250, 1100–1250, 1150–1250, 1200–1250, 783–1200, 800–1200, 850–1200, 900–1200, 950–1200, 1000–1200, 1050–1200, 1100–1200, 1150–1200, 783–1150, 800–1150, 850–1150, 900–1150, 950–1150, 1000–1150, 1050–1150, 1100–1150, 783–1100, 800–1100, 850–1100, 900–1100, 950–1100, 1000–1100, 1050–1100, 783–1050, 800–1050, 850–1050, 900–1050, 950–1050, 1000–1050, 783–1000, 800–1000, 850–1000, 900–1000, 950–1000, 783–950, 800–950, 850–950, 900–950, 783–900, 800–900, and 850–900 of SEQ ID NO:1, or the complementary polynucleotide strand thereto, or the cDNA contained in the deposited clone HUVEO91.

In additional specific embodiments, the polynucleotide fragments of the invention comprise, or alternatively, consist of, a polynucleotide comprising any portion of at least 30 nucleotides, preferably at least 50 nucleotides, of SEQ ID NO:19 from nucleotide residue 1 to 1116, preferably excluding the nucleotide sequences determined from the abovelisted cDNA clones (i.e., list from p.25).

Preferred embodiments of the invention encompass polynucleotides encoding polypeptides comprising, or alternatively consisting of, the amino acid sequence of residues −1–147 (i.e., −1 to 147), 1–147 (i.e., +1 to 147), 2–147, 3–147, 4–147, 5–147, 6–147, 7–147, 8–147, 9–147, 10–147, 11–147, 12–147, and 13–147 of SEQ ID NO:2. Polynucleotides encoding these polypeptides are also provided.

Representative examples of the TNF-gamma-beta polynucletoide fragments of the invention, include fragments that comprise, or alternativelty, consist of, nucleotides 1–1116, 50–1116, 100–1116, 150–1116, 200–1116, 250–1116, 300–1116, 350–1116, 400–1116, 450–1116, 500–1116, 550–1116, 600–1116, 650–1116, 700–1116, 750–1116, 800–1116, 850–1116, 900–1116, 950–1116, 1000–1116, 1050–1116, 1–1100, 50–1100, 100–1100, 150–1100, 200–1100, 250–1100, 300–1100, 350–1100, 400–1100, 450–1100, 500–1100, 550–1100, 600–1100, 650–1100, 700–1100, 750–1100, 800–1100, 850–1100, 900–1100, 950–1100, 1000–1100, 1050–1100, 1–1050, 50–1050, 100–1050, 150–1050, 200–1050, 250–1050, 300–1050, 350–1050, 400–1050, 450–1050, 500–1050, 550–1050, 600–1050, 650–1050, 700–1050, 750–1050, 800–1050, 850–1050, 900–1050, 950–1050, 1000–1050, 1–1000, 50–1000, 100–1000, 150–1000, 200–1000, 250–1000, 300–1000, 350–1000, 400–1000, 450–1000, 500–1000, 550–1000, 600–1000, 650–1000, 700–1000, 750–1000, 800–1000, 850–1000, 900–1000, 950–1000, 1–950, 50–950, 100–950, 150–950, 200–950, 250–950, 300–950, 350–950, 400–950, 450–950, 500–950, 550–950, 600–950, 650–950, 700–950, 750–950, 800–950, 850–950, 900–950, 1–900, 50–900, 100–900, 150–900, 200–900, 250–900, 300–900, 350–900, 400–900, 450–900, 500–900, 550–900, 600–900, 650–900, 700–900, 750–900, 800–900, 850–900, 1–850, 50–850, 100–850, 150–850, 200–850, 250–850, 300–850, 350–850, 400–850, 450–850, 500–850, 550–850, 600–850, 650–850, 700–850, 750–850, 800–850, 1–800, 50–800, 100–800, 150–800, 200–800, 250–800, 300–800, 350–800, 400–800, 450–800, 500–800, 550–800, 600–800, 650–800, 700–800, 750–800, 1–750, 50–750, 100–750, 150–750, 200–750, 250–750, 300–750, 350–750, 400–750, 450–750, 500–750, 550–750, 600–750, 650–750, 700–750, 1–700, 50–700, 100–700, 150–700, 200–700, 250–700, 300–700, 350–700, 400–700, 450–700, 500–700, 550–700, 600–700, 650–700, 1–650, 50–650, 100–650, 150–650, 200–650, 250–650, 300–650, 350–650, 400–650, 450–650, 500–650, 550–650, 600–650, 1–600, 50–600, 100–600, 150–600, 200–600, 250–600, 300–600, 350–600, 400–600, 450–600, 500–600, 550–600, 1–550, 50–550, 100–550, 150–550, 200–550, 250–550, 300–550, 350–550, 400–550, 450–550, 500–550, 1–500, 50–500, 100–500, 150–500, 200–500, 250–500, 300–500, 350–500, 400–500, 450–500, 1–450, 50–450, 100–450, 150–450, 200–450, 250–450, 300–450, 350–450, 400–450, 1–400, 50–400, 100–400, 150–400, 200–400, 250–400, 300–400, 350–400, 1–350, 50–350, 100–350, 150–350, 200–350, 250–350, 300–350, 1–300, 50–300, 100–300, 150–300, 200–300, 250–300, 1–250, 50–250, 100–250, 150–250, 200–250, 1–200, 50–200, 100–200, 150–200, 1–150, 50–150, 100–150, 1–100, 50–100, and 1–50 of SEQ ID NO:19 or the complementary polynucleotide strand thereto, or the cDNA contained in the deposited clone HEMCZ56.

Preferred nucleic acid fragments of the present invention also include nucleic acid molecules encoding one or more of the following domains of TNF-gamma-alpha (e.g., as described also in the legend to FIGS. 1A and 1B): potential asparagine-linked glycosylation sites N-29 through N-32 (N-29, Y-30, T-31, N-32) and N-125 through D-128 (N-125, V-126, S-127, D-128); potential Protein Kinase C (PKC) phosphorylation sites T-32 through K-34 (T-32, N-33, K-34) and T-50 through R-52 (T-50, F-51, R-52); potential Casein Kinase II (CK2) phosphorylation sites S-83 through E-86 (S-83, Y-84, P-85, E-86); S-96 through E-99 (S-96, V-97, C-98, E-99); S-115 through E-118 (S-115, L-116, Q-117, E-118); S-130 through D-133 (S-130, L-131, V-132, D-133); and T-135 through D-138 (T-135, K-136, E-137, D-138); and potential myristylation sites G-20 through K-25 (G-20, L-21, A-22, F-23, T-24, K-25) and G-111 through L-116 (G-111, A-112, M-113, F-114, S-115, L-116) of SEQ ID NO:2.

Among the especially preferred polynucleotides of the invention are those characterized by encoding structural or functional attributes of TNF-gamma. Such polynucleotides encode amino acid residues that comprise alpha-helix and alpha-helix forming regions ("alpha-regions"), beta-sheet and beta-sheet forming regions ("beta regions"), turn and turn-forming regions ("turn-regions"), coil and coil-forming regions ("coil regions"), hydrophilic regions, hydrophobic regions, alpha amphipathic regions, beta amphipathic regions, surface forming regions, and high antigenic index regions (i.e., having an antigenic regions of three or more contiguous amino acid residues each of which having an antigenic index of greater than or equal to 1.5) of TNF-gamma. Certain preferred regions are those set out in FIG. 17, and include, but are not limited to, regions of the aforementioned types identified by analysis of the amino acid sequence depicted in FIG. 1 (SEQ ID NO:2) using the default parameters of the identified computer programs, such preferred regions include; Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index.

Data which represent TNF-gamma-beta in a fashion as described above for TNF-gamma-alpha (see FIG. 17) may easily be prepared using the amino acid sequence shown in FIGS. 20A and 20B and in SEQ ID NO:20. As such, each of the abovelisted structural or functional attributes of TNF-gamma listed above (i.e. Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index, etc.) apply equally well to TNF-gamma-alpha and TNF-gamma-beta.

Figure 17:
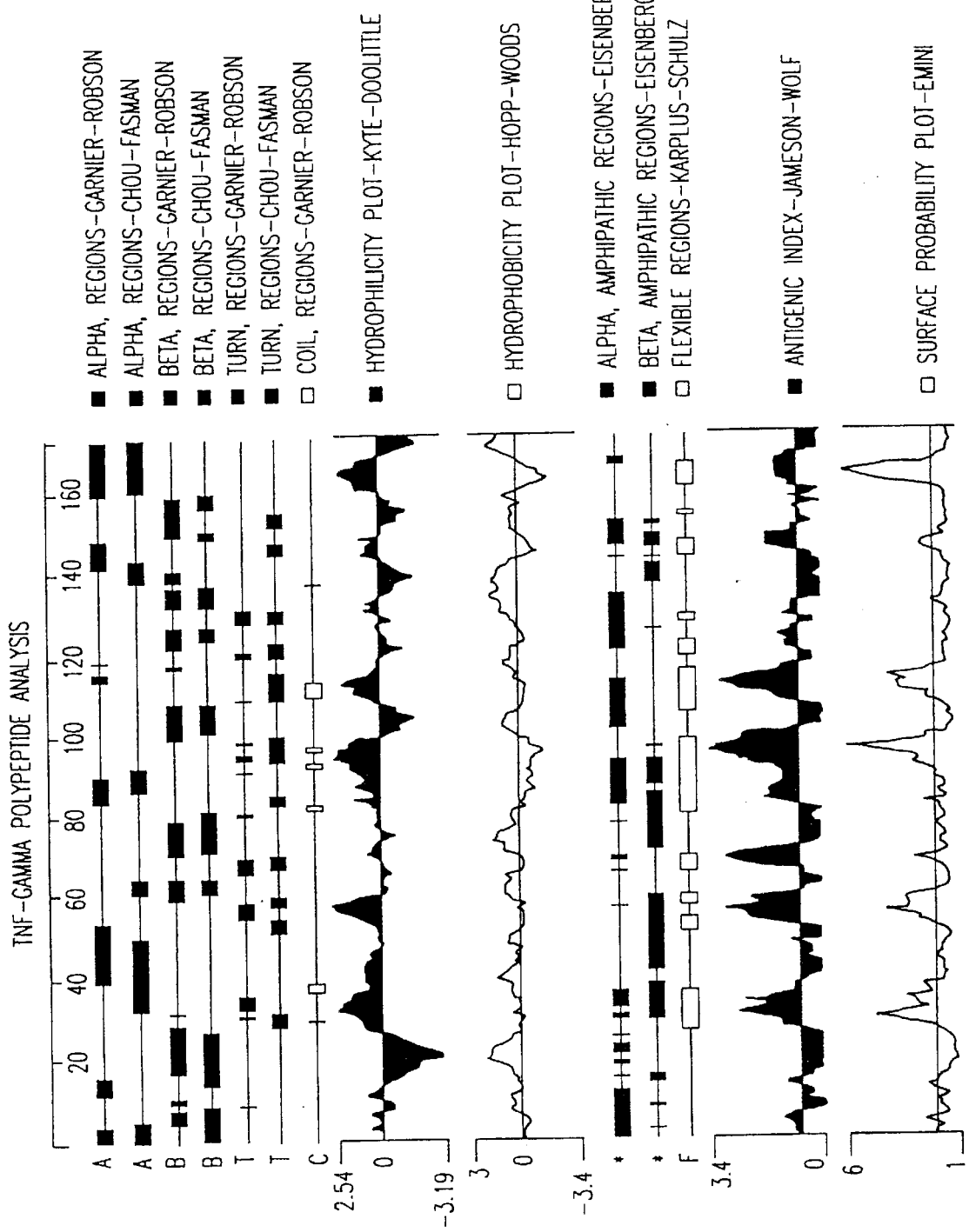
FIG. 17 shows an analysis of the TNF-gamma-alpha amino acid sequence (SEQ ID NO:2). Alpha, beta, turn and coil regions; hydrophilicity and hydrophobicity; amphipathic regions; flexible regions; antigenic index and surface probability are shown, as predicted using the default parameters of the recited computer programs. In the "Antigenic Index or Jameson-Wolf" graph, the positive peaks indicate locations of the highly antigenic regions of the TNF-gamma protein, i.e., regions from which epitope-bearing peptides of the invention can be obtained.

Certain preferred regions in these regards are set out in FIG. 17, but may also be represented or identified by using a tabular representation of the data presented in FIG. 17. The DNA*STAR computer algorithm used to generate FIG. 17 (set on the original default parameters) will easily present the data in FIG. 17 in such a tabular format. A tabular format of the data in FIG. 17 may be used to easily determine specific boundaries of a preferred region.

The above-mentioned preferred regions set out in FIG. 17 include, but are not limited to, regions of the aforementioned types identified by analysis of the amino acid sequence set out in FIGS. 1A and 1B. As set out in FIG. 17, such preferred regions include Garnier-Robson alpha-regions, beta-regions, turn-regions, and coil-regions, Chou-Fasman alpha-regions, beta-regions, and coil-regions, Kyte-Doolittle hydrophilic regions and hydrophobic regions. Eisenberg alpha- and beta-amphipathic regions, Karplus-Schulz flexible regions, Emini surface-forming regions and Jameson-Wolf regions of high antigenic index.

Among highly preferred fragments in this regard are those that comprise reigons of TNF-gamma-alpha and/or TNF-gamma-beta that combine several structural features, such as several (e.g., 1, 2, 3 or 4) of the features set out above.

Additional preferred nucleic acid fragments of the present invention include nucleic acid molecules encoding one or more epitope-bearing portions of the TNF-gamma polypeptide. In particular, such nucleic acid fragments of the present invention included nucleic acid molecules encoding: a polypeptide comprising amino acid residues from about Thr-24 to about Asn-32 in SEQ ID NO:2; a polypeptide comprising amino acid residues from about Ile-37 to about Ile-45 in SEQ ID NO:2; a polypeptide comprising amino acid residues from about Met-54 to about Arg-62 in SEQ ID NO:2; a polypeptide comprising amino acid residues from about Gln-63 to about Asp-71 in SEQ ID NO:2; a polypeptide comprising amino acid residues from about Glu-57 to about Gly-65 in SEQ ID NO:2; a polypeptide comprising amino acid residues from about Val-80 to about Thr-88 in SEQ ID NO:2; a polypeptide comprising amino acid residues from about Leu-116 to about Val-124 in SEQ ID NO:2; and a polypeptide comprising amino acid residues from about Asp-133 to about Phe-141 in SEQ ID NO:2. These polypeptide fragments have been determined to bear antigenic epitopes of the TNF-gamma protein by the analysis of the Jameson-Wolf antigenic index, as shown in FIG. 17, above. Methods for determining other such epitope-bearing portions of TNF-gamma are described in detail below.

Polypeptide fragments which bear antigenic epitopes of the TNF-gamma-beta protein may be easily determined by one of skill in the art using the above-described analysis of the Jameson-Wolf antigenic index, as shown in FIG. 17. Methods for determining other such epitope-bearing portions of TNF-gamma-beta are described in detail below.

Another embodiment of the invention is directed to polynucleotides that hybridize, preferably under stringent hybridization conditions, to a portion of the polynucleotide sequence of a polynucleotide of the invention such as, for instance, the cDNA clone contained in ATCC Deposit No. 75927, the cDNA clone contained in ATCC Deposit 203055 or a TNF-gamma polynucleotide fragment as described herein. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65° C. By a polynucleotide which hybridizes to a "portion" of a polynucleotide is intended a polynucleotide (either DNA or RNA) hybridizing to at least 15 nucleotides (nt), and more preferably at least 20 nt, still more preferably at least 30 nt, and even more preferably 30–70, or 80–150 nt, or the entire length of the reference polynucleotide. These are useful as diagnostic probes and primers as discussed above and in more detail below. Of course a polynucleotide which hybridizes only to a poly A sequence (such as the 3' terminal poly tract of the TNF-gamma cDNA shown in SEQ ID NO:1 or SEQ ID NO:19), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone generated using oligo dT as a primer).

In preferred embodiments, polynucleotides which hybridize to the reference polynucleotides disclosed herein encode polypeptides which either retain substantially the same biological function or activity as the mature polypeptide encoded by the polynucleotide sequences depicted in FIGS. 1A and 1B (SEQ ID NO:1) and/or FIGS. 20A and B (SEQ ID NO:19), or the cDNAs contained in the deposit.

Alternative embodiments are directed to polynucleotides which hybridize to the reference polynucleotide (i.e., a polynucleotide sequence disclosed herein), but do not retain biological activity. While these polynucleotides do not retain biological activity, they have uses, such as, for example, as probes for the polynucleotide of SEQ ID NO:1, for recovery of the polynucleotide, as diagnostic probes, and as PCR primers.

The present invention further relates to variants of the nucleic acid molecules of the present invention, which encode portions, analogs or derivatives of the TNF-gamma protein. Variants may occur naturally, such as a natural allelic variant. By an "allelic variant" is intended one of several alternate forms of a gene occupying a given locus on a chromosome of an organism (*Genes II*, Lewin, B., ed., John Wiley & Sons, New York (1985)). Non-naturally occurring variants may be produced using art-known mutagenesis techniques.

Such variants include those produced by nucleotide substitutions, deletions or additions of the polynucleotide sequences described herein (including fragments). The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the TNF-gamma protein or portions thereof. Also especially preferred in this regard are conservative substitutions.

Further embodiments of the invention are directed to isolated nucleic acid molecules comprising a polynucleotide sequence at least 70% or at least 80% identical, more preferably at least 90% identical, and still more preferably at least 95%, 96%, 97%, 98% or 99% identical to a polynucleotide having a nucleotide sequence selected from the group consisting of: (a) a nucleotide sequence encoding the TNF-gamma-alpha polypeptide having the complete amino acid sequence in SEQ ID NO:2 (i.e., positions –27 to 147 of SEQ ID NO:2); (b) a nucleotide sequence encoding the TNF-gamma-alpha polypeptide having the complete amino acid sequence in SEQ ID NO:2 excepting the N-terminal methionine (i.e., positions –26 to 147 of SEQ ID NO:2); (c) a nucleotide sequence encoding the mature TNF-gamma-alpha polypeptide having the amino acid sequence in SEQ ID NO:2 shown as positions 1 to 147 of SEQ ID NO:2; (d) a nucleotide sequence encoding the extracellular domain of the TNF-gamma-alpha polypeptide having the amino acid sequence in SEQ ID NO:2 shown as positions 1 to 147 of SEQ ID NO:2; (e) a nucleotide sequence encoding the TNF-gamma-alpha polypeptide having the complete amino acid sequence encoded by the cDNA clone HUVEO91 contained in ATCC Deposit No. 75927; (f) a nucleotide sequence encoding the TNF-gamma-alpha polypeptide having the complete amino acid sequence excepting the N-terminal methionine encoded by the cDNA clone HUVEO91 contained in ATCC Deposit No. 75927; (g) a nucleotide sequence encoding the mature TNF-gamma-alpha polypeptide having the amino acid sequence encoded by the cDNA clone HUVEO91 contained in ATCC Deposit No. 75927; (h) a nucleotide sequence encoding the extracellular domain of the TNF-gamma-alpha polypeptide having the amino acid sequence encoded by the cDNA clone HUVEO91 contained in ATCC Deposit No. 75927; (i) a nucleotide sequence encoding a polyeptide fragment described herein; and (j) a nucleotide sequence complementary to any of the nucleotide sequences in (a), (b), (c), (d), (e), (f), (g), (h) or (i), above. The polypeptides of the present invention also include polypeptides having an amino acid sequence at least 80% identical, more preferably at least 90% identical, and still more preferably 95%, 96%, 97%, 98% or 99% identical to those described in (a), (b), (c), (d), (e), (f), (g), (h), (i) or (j), above, as well as polypeptides having an amino acid sequence with at least 90% similarity, and more preferably at least 95% similarity, to those above.

Further embodiments of the invention are directed to isolated nucleic acid molecules comprising a polynucleotide sequence at least 70% or at least 80% identical, more preferably at least 90% identical, and still more preferably at least 95%, 96%, 97%, 98% or 99% identical to a polynucleotide having a nucleotide sequence selected from the group consisting of: (a) a nucleotide sequence encoding the TNF-gamma-beta polypeptide having the complete amino acid sequence in SEQ ID NO:20 (i.e., positions 1 to 251 of SEQ ID NO:20); (b) a nucleotide sequence encoding the TNF-gamma-beta polypeptide having the complete amino acid sequence in SEQ ID NO:20 excepting the N-terminal methionine (i.e., positions 2 to 251 of SEQ ID NO:20); (c) a nucleotide sequence encoding the mature TNF-gamma-beta polypeptide having the amino acid sequence in SEQ ID NO:20 shown as positions 62 to 251 of SEQ ID NO:20; (d) a nucleotide sequence encoding the intracellular domain of the TNF-gamma-beta polypeptide having the amino acid sequence in SEQ ID NO:20 shown as positions 1 to 35 of SEQ ID NO:20; (e) a nucleotide sequence encoding the extracellular domain of the TNF-gamma-beta polypeptide having the amino acid sequence in SEQ ID NO:20 shown as positions 62 to 251 of SEQ ID NO:20; (f) a nucleotide sequence encoding the TNF-gamma-beta polypeptide having the complete amino acid sequence encoded by the cDNA clone HEMCZ56 contained in ATCC Deposit No. 203055; (g) a nucleotide sequence encoding the TNF-gamma-beta polypeptide having the complete amino acid sequence excepting the N-terminal methionine encoded by the cDNA clone HEMCZ56 contained in ATCC Deposit No. 203055; (h) a nucleotide sequence encoding the mature TNF-gamma-beta polypeptide having the amino acid sequence encoded by the cDNA clone HEMCZ56 contained in ATCC Deposit No. 203055; (i) a nucleotide sequence encoding the intracellular domain of the TNF-gamma-beta polypeptide having the amino acid sequence encoded by the cDNA clone HEMCZ56 contained in ATCC Deposit No. 203055; (j) a nucleotide sequence encoding the extracellular domain of the TNF-gamma-beta polypeptide having the amino acid sequence encoded by the cDNA clone HEMCZ56 contained in ATCC Deposit No. 203055; and (k) a nucleotide sequence complementary to any of the nucleotide sequences in (a), (b), (c), (d), (e), (f), (g), (h), (i) or (j), above. The polypeptides of the present invention also include polypeptides having an amino acid sequence at least 80% identical, more preferably at least 90% identical, and still more preferably 95%, 96%, 97%, 98% or 99% identical to those described in (a), (b), (c), (d), (e), (f), (g), (h), (i), (j) or (k), above, as well as polypeptides having an amino acid sequence with at least 90% similarity, and more preferably at least 95% similarity, to those above.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the TNF-gamma polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The reference (query) sequence may be the entire nucleotide sequence shown in FIGS. 1A and B (SEQ ID NO:1) and FIGS. 20A and B (SEQ ID NO:19), or any fragment as described herein.

As a practical matter, whether any particular nucleic acid molecule is at least 70%, 80%, 90%, 95%, 96%, 97%, 98% or 99% identical to, for instance, the nucleotide sequence shown in FIGS. 1A and B (SEQ ID NO:1), FIGS. 20A and B (SEQ ID NO:19), or to the nucleotide sequence of the deposited cDNA clones can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

In further embodiments, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

In further embodiments, the present invention is directed to polynucleotides having at least a 70% identity, preferably at least 90% and more preferably at least a 95% identity to a polynucleotide which encodes the polypeptide of SEQ ID NO:20 as well as fragments thereof, which fragments have at least 30 bases and preferably at least 50 bases and to polypeptides encoded by such polynucleotides.

The present application is directed to nucleic acid molecules at least 70%, 80%, 90%, 95%, 96%, 97%, 98% or 99% identical to the polynucleotide sequence shown in FIGS. 1A and B (SEQ ID NO:1), FIGS. 20A and B (SEQ ID NO:19), or to the nucleic acid sequence of the deposited cDNA clones or fragments thereof, irrespective of whether they encode a polypeptide having TNF-gamma functional activity. This is because even where a particular nucleic acid molecule does not encode a polypeptide having TNF-gamma functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having TNF-gamma functional activity include, inter alia, (1) isolating the TNF-gamma gene or allelic variants thereof in a cDNA library; (2) in situ hybridization (e.g., "FISH") to metaphase chromosomal spreads to provide precise chromosomal location of the TNF-gamma gene, as described in Verma et al., *Human Chromosomes: A Manual of Basic Techniques,* Pergamon Press, N.Y. (1988); and (3) Northern Blot analysis for detecting TNF-gamma mRNA expression in specific tissues.

Preferred, however, are nucleic acid molecules having sequences at least 70%, 80%, 90%, 95%, 96%, 97%, 98% or 99% identical to the nucleic acid sequence shown in FIGS. 1A and B (SEQ ID NO:1), FIGS. 20A and B (SEQ ID NO:19), or to the nucleic acid sequence of the deposited cDNA clones, or fragments thereof, which do, in fact, encode a polypeptide having TNF-gamma functional activity. By "a polypeptide having TNF-gamma functional activity" is intended polypeptides exhibiting activity similar, but not necessarily identical, to an activity of the TNF-gamma polypeptide of the invention (either the full-length protein or, preferably, the mature protein), as measured in a particular immunoassay and/or biological assay. For example, TNF-gamma activity can be measured using an apoptosis assay as described in Example 7, by determining the relative ability of TNF-gamma to inhibit the FGF-2-induced formation of capillary-like tubular structure formation in cultures of ABAE cells as described in detail in Example 9 or in a chorioallantoic membrane (CAM) angiogenesis assay as described in Example 10, by its effect(s) on the activation of cellular NP-B and c-Jun kinase (JNK) as described in Example 12, and in several additional ways described in the remaining Examples and in the art.

Of course, due to the degeneracy of the genetic code, one of ordinary skill in the art will immediately recognize that a large number of the nucleic acid molecules having a sequence at least 70%, 80%, 90%, 95%, 96%, 97%, 98%, or 99% identical to the nucleic acid sequence of the deposited cDNA or the nucleic acid sequence shown in FIGS. 1A and 1B (SEQ ID NO:1), FIGS. 20A and 20B (SEQ ID NO:19), or fragments thereof, will encode a polypeptide "having TNF-gamma activity." In fact, since degenerate variants of these nucleotide sequences all encode the same polypeptide, in many instances this will be clear to the skilled artisan even without performing the above described assay. It will be further recognized in the art that, for such nucleic acid molecules that are not degenerate variants, a reasonable number will also encode a polypeptide having TNF-gamma activity. This is because the skilled artisan is fully aware of amino acid substitutions that are either less likely or not likely to significantly effect protein function (e.g., replacing one aliphatic amino acid with a second aliphatic amino acid). For example, guidance concerning how to make phenotypically silent amino acid substitutions is provided in J. U. Bowie et al., "Deciphering the Message in Protein Sequences: Tolerance to Amino Acid Substitutions," *Science* 247:1306–1310 (1990), wherein the authors indicate that proteins are surprisingly tolerant of amino acid substitutions.

Additional embodiments of the invention are directed to isolated nucleic acid molecules comprising a polynucleotide which encodes the amino acid sequence of a TNF-gamma polypeptide (e.g., a TNF-gamma polypeptide fragment described herein) having an amino acid sequence which contains at least one conservative amino acid substitution but not more than 50 conservative amino acid substitutions even more preferably, not more than 40 conservative amino acid substitutions, still more preferably, not more than 30 conservative amino acid substitutions, and still even more preferably, not more than 20 conservative amino acid substitutions, 10–20 conservative amino acid substitutions, 5–10 conservative amino acid substitutions, 1–5 conservative amino acid substitutions, 3–5 conservative amino acid substitutions, or 1–3 conservative amino acid substitutions. Of course, in order of ever-increasing preference, it is highly preferable for a polynucleotide which encodes the amino acid sequence of a TNF-gamma polypeptide to have an amino acid sequence which contains not more than 10, 9, 8, 7, 6, 5, 4, 3, 2 or 1 conservative amino acid substitutions.

Polynucleotide Assays

The invention also encompasses the use of TNF-gamma polynucleotides to detect complementary polynucleotides, such as, for example, as a diagnostic reagent for detecting diseases or susceptibility to diseases related to the presence of mutated TNF-gamma-alpha or TNF-gamma-beta. Such diseases are related to an under-expression of TNF-gammaalpha or TNF-gamma-beta, such as, for example, abnormal cellular proliferation such as tumors and cancers.

Individuals carrying mutations in the human TNF-gamma gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding TNF-gamma-alpha or TNF-gamma-beta can be used to identify and analyze TNF-gamma mutations. For example, deletions and insertions can be detected by a change in size of the amplified product in comparison to the normal genotype. Point mutations can be identified by hybridizing amplified DNA to radiolabeled TNF-gamma RNA or alternatively, radiolabeled TNF-gamma antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al, Science, 230:1242 (1985)).

Sequence changes at specific locations may also be revealed by nuclease protection assays, such as RNase and S1 protection or the chemical cleavage method (e.g., Cotton et al, PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

Vectors and Host Cells

The present invention also relates to vectors which include the isolated polynucleotides of the present invention, host cells which are genetically engineered with the recombinant vectors, or which are otherwise engineered to produce the polypeptides of the invention, and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the TNF-gamma genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operably associated with an appropriate expression control sequence (s) (promoter) to direct mRNA synthesis. As representative examples of such promoters, there may be mentioned: LTR or SV40 promoter, the *E. coli* lac or trp, the phage lambda P promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Salmonella typhimurium;* fungal cells, such as yeast; insect cells such as Drosophila S2 and Sf9; animal cells such as CHO, COS or Bowes melanoma, adenoviruses, plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably associated with the sequence. Large numbers of suitable vectors and promoters are known to those of skill in the art, and are commercially available. The following vectors are provided by way of example. Bacterial: pHE4–5 (ATCC Accession No. 209311; and variations thereof), pQE70, pQE60, pQE-9 (Qiagen), pBS, pD10, phagescript, psiX174, pBluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include *lacI, lacZ,* T3, T7, gpt, lambda P, P, and *trp*. Eukaryotic promoters include CMV immediate early, HSV thymidine kinase, early and late SV40, LTRs from retroviruses, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., TNF-gamma coding sequence), and/or to include genetic material (e.g., heterologous polynucleotide sequences) that is operably associated with TNF-gamma polynucleotides of the invention, and which activates, alters, and/or amplifies endogenous TNF-gamma polynucleotides. For example, techniques known in the art may be used to operably associate heterologous control regions (e.g., promoter and/or enhancer) and endogenous TNF-gamma polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRPI gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, for example, stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium,* and various species within the genera Pseudomonas, Streptomyces, and Staphylococcus, although others may also be employed as a matter of choice.

As a representative, but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman (*Cell* 23:175 (1981)), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The TNF-gamma polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

At least fifteen TNF-gamma-alpha expression constructs have been generated by the inventors herein to facilitate the production of TNF-gamma polypeptides of several sizes and in several systems. Of these, four have been constructed which encode a full-length TNF-gamma polypeptide. The full-length constructs are: (i) pQE9TNFg-27/147, (ii) pQE70TNFg, (iii) pC1TNFg, and pcDNA3TNFg. In the case of the first expression construct listed (pQE9TNFg-27/147), the construct was used to produce a full-length TNF-gamma-alpha polypeptide with an N-terminal six histidine amino acid tag according to the method of Example 1. A full-length TNF-gamma-alpha polypeptide lacking the histidine tag was produced in bacteria by using the pQE70TNFg construct essentially as was done in Example 1. In addition, a full-length TNF-gamma-alpha polypeptide lacking a histidine tag was produced in mammalian cells by using either the pC1TNFg or pcDNA3TNFg constructs according to the method of Example 3. Further, the mature TNF-gamma-alpha polypeptide was produced and secreted from mammalian cells under direction of the interleukin (IL)-6 signal peptide from a construct designated pcDNA3/IL6TNFg-1/149 (see Example 11).

The remaining TNF-gamma-alpha expression constructs were used to express various TNF-gamma muteins from bacterial, baculoviral, and mammalian systems. Four N-terminal deletion mutations have been generated using the pQE60 bacterial expression vector. These N-terminal deletion mutation constructs are: (I) pQE60TNFg-3/147 (representing a possible mature TNF-gamma polypeptide; the polypeptide expressed by this construct is identical to amino acid residues 107–251 of the TNF-gamma-beta of SEQ ID NO:20), (ii) pQE60TNFg12/147 (representing amino acid residues 12–147 of SEQ ID NO:2 and residues 116–251 of SEQ ID NO:20), (iii) pQE60TNFg22/147 (representing amino acid residues 22–147 of SEQ ID NO:2 and residues 126–251 of SEQ ID NO:20), and (iv) pQE60TNFg28/147 (representing amino acid residues 28–147 of SEQ ID NO:2 and residues 132–251 of SEQ ID NO:20). Each of these expression constructs can be used to produce a TNF-gamma polypeptide in a bacterial system which exhibits an N-terminal deletion of 29, 38, 48 and 54 amino acids, respectively, with regard to the full-length TNF-gamma-alpha polypeptide or an N-terminal deletion of 106, 115, 125, and 131 amino acids, respectively, with regard to the full-length TNF-gamma-beta polypeptide.

Further N-terminal deletion mutation bacterial expression constructs have been generated. A construct designated pHE4 VEGI T30-L174 has been generated using the bacterial expression vector pHE4 to express amino acids threonine-30 to leucine-174 of the TNF-gamma-alpha sequence shown in FIGS. 1A and 1B (residues threonine-3 to leucine-147 of SEQ ID NO:2) which correspond exactly to amino acid residues threonine-107 to leucine-251 of the TNF-gamma-beta sequence shown in FIGS. 20A and 20B (residues threonine-107 to leucine-251 of SEQ ID NO:20). Additional bacterial expression constructs generated include pQE9.VEGI.his.T28-L 174, pHE4.VEGI.T28-L174, pHE4.VEGI.T51-L174, and pHE4.VEGI.T58-L174. These constructs are based on either the pQE9 or pHE4 bacterial expression vectors. The construct designations indicate the expression vector, the gene name, and the amino acid residues expressed by the construct (e.g. pQE9.VEGI.T28-L174 indicates that the pQE9 bacterial expression vector is used to express amino acids threonine (T)-28 through leucine (L)-174 of the TNF-gamma-alpha polypeptide (VEGI is a laboratory designation for TNF-gamma-alpha)).

A TNF-gamma expression construct has been generated which can be used to produce a secreted mature TNF-gamma polypeptide from a mammalian system. The construct has been designated pC1/IL6TNFg-3/147. It encodes the signal peptide from the human IL-6 gene fused to the mature TNF-gamma sequence. A similar construct has been generated which contains the CK-β8 signal peptide (amino acids −21 to −1 of the CK-β8 sequence disclosed in published PCT application PCT/US95/09058; filed Jun. 23, 1995) fused to the amino terminus of amino acids 12–149 of TNF-gamma-alpha (SEQ ID NO:2; that is amino acids 116–251 of TNF-gamma-beta (SEQ ID NO:20)) in the context of the pC4 mammalian expression vector. This construct has been designated pC4/CK-β8TNFg12/147. A variant of this construct has been generated which can be used to express amino acids 12–147 of TNF-gamma fused to the human IgG Fc region at the TNF-gamma carboxy terminus. This fusion protein is also secreted under the direction of the CK-β8 signal peptide and has been designated pC4/CK-β8TNFg12/147/Fc. The sequence of the human Fc portion of the fusion molecule is shown in SEQ ID NO:18. Other sequences could be used which are known to those of skill in the art.

Amino acids −3 to 147 of TNF-gamma-alpha (SEQ ID NO:2; which correspond to amino acid residues 102 to 251 of TNF-gamma-beta (SEQ ID NO:20)) can be expressed and secreted from a baculovirus system by using a construct designated pA2GPTNFg-3/147. This expression construct encodes the mature TNF-gamma coding sequence fused at its amino terminus to the baculoviral GP signal peptide.

Two retroviral TNF-gamma expression constructs have also been generated. The first of these has been designated pG1SamEN/TNFg-3/149. This expression construct can be used to produce full-length TNF-gamma protein from a mammalian system. A related construct, pG1SamEN/CK-β8TNFg12/149, has been generated which can be used to produce and secrete mature TNF-gamma protein from a mammalian system under the direction of the CK-β8 signal peptide.

Further polypeptides of the present invention include polypeptides which have at least 90% similarity, more preferably at least 95% similarity, and still more preferably at least 96%, 97%, 98% or 99% similarity to those described above. The polypeptides of the invention also comprise those which are at least 80% identical, more preferably at least 90% or 95% identical, still more preferably at least 96%, 97%, 98% or 99% identical to the polypeptide encoded by the deposited cDNA or to the polypeptide of SEQ ID NO:2, and also include portions of such polypeptides with at least 30 amino acids and more preferably at least 50 amino acids.

Polypeptides and Fragments

The present invention further relates to an isolated TNF-gamma-alpha polypeptide which has the deduced amino acid sequence of FIGS. 1A and 1B (SEQ ID NO:2) or which has the amino acid sequence encoded by the deposited cDNA HUVEO91, as well as fragments, analogs and derivatives of such polypeptide.

The present invention also relates to a TNF-gamma-beta polypeptide which has the deduced amino acid sequence of FIGS. 20A and 20B (SEQ ID NO:20) or which has the amino acid sequence encoded by the deposited cDNA HEMCZ56, as well as fragments, analogs and derivatives of such polypeptide.

The polypeptides and polynucleotides of the present invention are preferably provided in an isolated form, and preferably are purified to a point within the range of near complete (e.g., >90% pure) to complete (e.g., >99% pure) homogeneity. The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Also intended as an "isolated polypeptide" are polypeptides that have been purified partially or substantially from a recombinant host cell. For example, a recombinantly produced version of a TNF-gamma polypeptide can be substantially purified by the one-step method described by Smith and Johnson (*Gene* 67:31–40 (1988)). Such polynucleotides could be part of a vector and/or such polynucleotides or polypeptides could be part of a composition, and still be isolated in that such vector or composition is not part of its natural environment. Isolated polypeptides and polynucleotides according to the present invention also include such molecules produced naturally or synthetically. Polypeptides and polynucleotides of the invention also can be purified from natural or recombinant sources using anti-TNF-gamma antibodies of the invention in methods which are well known in the art of protein purification.

The terms "fragment," "derivative" and "analog" when referring to the polypeptides of FIGS. 1A and 1B or FIGS. 20A and 20B, and those polypeptides encoded by the deposited cDNAs, means a polypeptide which retains a TNF-gamma functional activity, i.e., displays one or more functional activities associated with a full-length and/or mature TNF-gamma polypeptide disclosed in FIGS. 1A and B (SEQ ID NO:2), FIGS. 20A and B (SEQ ID NO:20), and/or encoded by one or both of the deposited clones (HUVEO91 and HEMCZ56). As one example, such fragments, derivatives, or analogs, which have the desired immunogenicity or antigenicity can be used, for example, in immunoassays, for immunization, for inhibition of TNF-gamma activity, etc. Thus, a specific embodiment of the invention relates to a TNF-gamma fragment that can be bound by an antibody that specifically binds the TNF-gamma polypeptide sequence disclosed in FIGS. 1A and B (SEQ ID NO:2), FIGS. 20A and B SEQ ID NO:20)), and/or which is encoded by one or both of the deposited clones (HUVEO91 and HEMCZ56).

As another example, TNF-gamma fragments, derivatives or analogs which have TNF-gamma biological activity (e.g., a mature TNF-gamma-alpha polypeptide or the extracellular domain of a TNF-gamma-beta polypeptide) are provided. TNF-gamma fragments, derivatives, and analogs that retain, or alternatively lack a desired TNF-gamma property of interest (e.g., inhibition of cell proliferation, tumor inhibition, inhibition of angiogenesis, anti-arthritis by the inhibition of angiogenesis and/or endothelial cell proliferation associated with invading pannus in bone and cartilage, an inducer of NF-κB and c-Jun kinase (JNK), an inducer of cell adhsion, and as an inducer apoptosis (See Examples, particularly Examples 12–15)) can be used as inducers or inhibitors, respectively, of such properties and its physiological correlates.

The polypeptides of the invention may exist as a membrane bound receptor having a transmembrane region and an intra- and extracellular region or they may exist in soluble form wherein the transmembrane domain is lacking. One example of such a form of TNF-gamma is the TNF-gamma-beta polypeptide sequence shown in FIGS. 20A and B (SEQ ID NO:20) which contains a transmembrane, intracellular and extracellular domain.

It will be recognized in the art that some amino acid sequences of the TNF-gamma polypeptide can be varied without significant effect of the structure or function of the protein. If such differences in sequence are contemplated, it should be remembered that there will be critical areas on the protein which determine activity. Thus, the invention further includes variations of the TNF-gamma polypeptide which show substantial TNF-gamma polypeptide activity or which include regions of TNF-gamma protein such as the polypeptide fragments disclosed herein. Such variants include deletions, insertions, inversions, repeats, and type substitutions selected according to general rules known in the art so as have little effect on activity. For example, guidance concerning how to make phenotypically silent amino acid substitutions is provided wherein the authors indicate that there are two main approaches for studying the tolerance of an amino acid sequence to change (Bowie et al., *Science* 247:1306–1310 (1990)). The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described by Bowie and coworkers (supra) and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative or analog of the polypeptide of SEQ ID NO:2, or of SEQ ID NO:20, or those encoded by the deposited cDNAs, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature form of the TNF-gamma polypeptide is fused with another compound, such as a compound to increase the half-life of the polypeptide (for example, polyethylene glycol), or (iv) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein.

Thus, the TNF-gamma of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Embodiments of the invention are directed to polypeptides which comprise the amino acid sequence of a TNF-gamma polypeptide descrubed hereub, but having an amino acid sequence which contains at least one conservative amino acid substitution, but not more than 50 conservative amino acid substitutions, even more preferably, not more than 40 conservative amino acid substitutions, still more preferably, not more than 30 conservative amino acid substitutions, and still even more preferably, not more than 20 conservative amino acid substitutions, when compared with the TNF-gamma polynucleotide sequence described herein. Of course, in order of ever-increasing preference, it is highly preferable for a peptide or polypeptide to have an amino acid sequence which comprises the amino acid sequence of a TNF-gamma polypeptide, which contains at least one, but not more than 10, 9, 8, 7, 6, 5, 4, 3, 2 or 1 conservative amino acid substitutions.

In further specific embodiments, the number of substitutions, additions or deletions in the amino acid sequence of FIGS. 1A and B (SEQ ID NO:2), FIGS. 20A and B (SEQ ID NO:20), a polypeptide sequence encoded by the deposited clones, and/or any of the polypeptide fragments described herein (e.g., the extracellular domain or intracellular domain) is 75, 70, 60, 50, 40, 35, 30, 25, 20, 15, 10, 9, 8, 7, 6, 5, 4, 3, 2, 1 or 150-50, 100-50, 50-20, 30-20, 20-15, 20-10, 15-10, 10-1, 5-10, 1-5, 1-3 or 1-2.

To improve or alter the characteristics of TNF-gamma polypeptides, protein engineering may be employed. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

Thus, the invention also encompasses TNF-gamma derivatives and analogs that have one or more amino acid residues deleted, added, or substituted to generate TNF-gamma polypeptides that are better suited for expression, scale up, etc., in the host cells chosen. For example, cysteine residues can be deleted or substituted with another amino acid residue in order to eliminate disulfide bridges; N-linked glycosylation sites can be altered or eliminated to acheive, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognitions sequences in the TNF-gamma polypeptides of the invention, and/or an amino acid deletion at the second position of any one or more such recognition sequences will prevent glycosylation of the TNF-gamma polypeptide at the modified tripeptide sequence (see, e.g., Miyajimo et al., EMBO J 5(6):1193–1197).

Amino acids in the TNF-gamma protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard, et al., *Clin. Exp. Immunol.* 2:331–340 (1967); Robbins, et al., *Diabetes* 36:838–845 (1987); Cleland, et al., *Crit. Rev. Therapeutic Drug Carrier Systems* 10:307–377 (1993)).

Since TNF-gamma is a member of the TNF-related protein family, to modulate rather than completely eliminate biological activities of TNF-gamma preferably additions, substitutions, or deletions are made in sequences encoding amino acids in the conserved TNF-like domain, i.e., in positions 17–147 of SEQ ID NO:2 or positions 121–251 of SEQ ID NO:20, more preferably in residues within this region which are not conserved in all members of the TNF-related protein family (see FIGS. 2A–2C). Also forming part of the present invention are isolated polynucleotides comprising nucleic acid sequences which encode the above TNF-gamma variants.

Several amino acids of the TNF-gamma polypeptide are highly conserved across the known members of the TNF-related protein family. By making a specific mutation in TNF-gamma in such residues as tryptophan-15 (as numbered in SEQ ID NO:2), leucine-35, glycine-41, tyrosine-43, tyrosine-46, glutamine-48, leucine-90, leucine-116, glycine-119, aspartic acid-120, phenylalanine-141, phenylalanine-142, and leucine-147, it is likely that an noticeable effect on biological activity will be observed. These identical amino acid residues are, of course, present in the corresponding positions of TNF-gamma-beta shown in SEQ ID NO:20.

The present invention also encompasses fragments of the above-described TNF-gamma polypeptides. Polypeptide fragments of the present invention include polypeptides comprising an amino acid sequence contained in SEQ ID NO:2, encoded by the cDNA contained in the deposited clone (HUVEO91), or encoded by nucleic acids which hybridize (e.g. under stringent hybridization conditions) to the nucleotide sequence contained in the deposited clones, that shown in FIGS. 1A and 1B (SEQ ID NO:1) and/or FIGS. 20A and 20B (SEQ ID NO:19), or the complementary strand thereto.

Polypeptide fragments may be "free-standing" or comprised within a larger polypeptide of which the fragment forms a part or region, most preferably as a single continuous region. Representative examples of polypeptide fragments of the invention, included, for example, fragmens that comprise or alternatively, consist of, from about amino acid residues, 1 to 20, 21 to 40, 41 to 60, 61 to 83, 84 to 100, 101 to 120, 121 to 140, 141 to 160, 160 to 167, 161 to 174, 161 to 180, 181 to 200, 201 to 220, 221 to 240, 241 to 251 of SEQ ID NO:2 and/or SEQ ID NO:20. Moreover, polypeptide fragments can be at least about 20, 30, 40, 50, 60, 70, 80, 90, 100, 110, 120, 130, 140 or 150 amino acids in length. In this context "about" includes the particularly recited ranges, larger or smaller by several (i.e. 5, 4, 3, 2 or 1) amino acids, at either extreme or at both extremes.

In other embodiments, the fragments or polypeptides of the invention (i.e., those described herein) are not larger than 250, 225, 200, 185, 175, 170, 165, 160, 155, 150, 145, 140, 135, 130, 125, 120, 115, 110, 105, 100, 90, 80, 75, 60, 50, 40, 30 or 25 amino acids residues in length.

Further preferred embodiments encompass polypeptide fragments comprising, or alternatively consisting of, the mature domain of TNF-gamma-alpha (amino acid residues 1–147 of SEQ ID NO:2), the intracellular domain of TNF-gamma-beta (amino acid residues 1–35 of SEQ ID NO:20), the transmembrane domain of TNF-gamma-beta (amino acid residues 36–61 of SEQ ID NO:20), and/or the extracellular domain of TNF-gamma-beta (amino acid residues 62–251 of SEQ ID NO:20).

In specific embodiments, polypeptide fragments of the invention comprise, or alternatively consist of, amino acid residues leucine-35 to valine-49, tryptophan-104 to leucine-116, glycine-119 to serine-127, lysine-139 to leucine-147 of SEQ ID NO:2). These domains are regions of high identity identified by comparison of the TNF family member polypeptides shown in FIGS. 2A, 2B, and 2C.

Among the especially preferred fragments of the invention are fragments characterized by structural or functional attributes of TNF-gamma. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophillic regions, hydrophobic regions, alpha amphipathic regions, beta amphipathic regions, surface forming regions, and high antigenic index regions (i.e., regions of polypeptides consisting of amino acid residues having an antigenic index of or equal to greater than 1.5, as identified using the default parameters of the Jameson-Wolf program) of TNF-gamma. Certain preferred regions are those disclosed in FIG. 17 and include, but are not limited to, regions of the aforementioned types identified by analysis of the amino acid sequence depicted in FIGS. 1A and B, such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

Additionally, analogs of the invention include a proprotein which can be activated by cleavage of the proprotein portion to produce an active mature polypeptide.

In another embodiment, the invention provides a TNF-gamma polypeptide (e.g., fragment) comprising, or alternatively, consisting of, an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope". The number of immunogenic epitopes of a protein generally is less than the number of antigenic epitopes (see, for instance, Geysen, et al., *Proc. Natl. Acad. Sci. USA* 81:3998–4002 (1983)).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein (see, for instance, Sutcliffe, J. G., et aL, *Science* 219:660–666 (1983)). Peptides capable of eliciting protein-reactive sera are frequently represented in the primary sequence of a protein can be characterized by a set of simple chemical rules and are confined neither to immunodominant regions of intact proteins (i.e., immunogenic epitopes) nor to the amino or carboxyl termini. Antigenic epitope-bearing peptides and polypeptides of the invention are therefore useful to raise antibodies, including monoclonal antibodies, that bind specifically to a polypeptide of the invention (see, for instance, Wilson, et aL. *Cell* 37:767–778 (1984)).

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention. Non-limiting examples of antigenic polypeptides or peptides that can be used to generate TNF-gamma-specific antibodies include: a polypeptide comprising amino acid residues from about Thr-24 to about Asn-32 in SEQ ID NO:2; a polypeptide comprising amino acid residues from about Ile-37 to about Ile-45 in SEQ ID NO:2; a polypeptide comprising amino acid residues from about Met-54 to about Arg-62 in SEQ ID NO:2; a polypeptide comprising amino acid residues from about Gln-63 to about Asp-71 in SEQ ID NO:2; a polypeptide comprising amino acid residues from about Glu-57 to about Gly-65 in SEQ ID NO:2; a polypeptide comprising amino acid residues from about Val-80 to about Thr-88 in SEQ ID NO:2; a polypeptide comprising amino acid residues from about Leu-116 to about Val-124 in SEQ ID NO:2; and a polypeptide comprising amino acid residues from about Asp-133 to about Phe-141 in SEQ ID NO:2. These polypeptide fragments have been determined to bear antigemc epitopes of the TNF-gamma protein by the analysis of the Jameson-Wolf antigenic index, as shown in FIG. 17, above.

One of ordinary skill in the art may easily determine antigenic regions for TNF-gamma-beta by using data prepared through a DNA*STAR analysis of the TNF-gamma-beta polypeptide sequence (SEQ ID NO:20) using the default parameters and selecting regions with a high antigenic index as described above.

The epitope-bearing peptides and polypeptides of the produced by any conventional means (see, for example, Houghten, R. A., et aL, *Proc. Natl. Acad Sci. USA* 82:5131–5135 (1985); and U.S. Pat. No. 4,631,211 to Houghten, et al. (1986)).

Epitope-bearing peptides and polypeptides of the invention invention have uses which include, but are not limited to, inducing antibodies according to methods well known in the art (see, for instance, Sutcliffe, et aL, supra; Wilson, et aL, supra; Chow, M., et al, *Proc. NatL Acad Sci. USA* 82:910–914; and Bittle, F. J., et aL, *J Gen. ViroL* 66:2347–2354 (1985)). Immunogenic epitope-bearing peptides of the invention, i.e., those parts of a protein that elicit an antibody response when the whole protein is the immunogen, are identified according to methods known in the art (see, for instance, Geysen, et aL, supra). Further still, U.S. Pat. No. 5,194,392, issued to Geysen, describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092, issued to Geysen, describes a method of detecting or determining a sequence of monomers which is a topographical equivalent of a ligand which is complementary to the ligand binding site of a particular receptor of interest (e.g. DR3). Similarly, U.S. Pat. No. 5,480,971, issued to Houghten and colleagues, on Peralkylated Oligopeptide Mixtures discloses linear C1–C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

As one of skill in the art will appreciate, TNF-gamma-alpha and/or TNF-gamma-beta polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker, et al, *Nature* 331:84–86 (1988)). Fusion proteins that have a disulfide-linked dimeric structure due to the IgG part can also be more efficient in binding and neutralizing other molecules than the monomeric TNF-gamma protein or protein fragment alone (Fountoulakis, et al., *J. Biochem.* 270:3958–3964 (1995)). As an example, one such TNF-gamma-Fc fusion has been produced herein as described above.

Fragments (i.e., portions) of the TNF-gamma polypeptides of the present on have uses which include, but are not limited to, intermediates for producing full-length polypeptides.

For many proteins, including the extracellular domain of a membrane associated protein or the mature form(s) of a secreted protein, it is known in the art that one or more amino acids may be deleted from the N-terminus or C-terminus without substantial loss of biological function. For instance, Ron and colleagues (*J. Biol. Chem.,* 268:2984–2988 (1993)) reported modified KGF proteins that had heparin binding activity even if 3, 8, or 27 N-terminal amino acid residues were missing. Further, several investigators have reported TNF-α muteins in which two, four or seven N-terminal amino acids had been removed which showed a 2- to 3-fold increase in functional acitivity when compared to the naturally-occurring TNF-α polypeptide (Creasey, A. A., et al., *Cancer Res.* 47:145–149 (1987); Sidhu, R. S. and Bollon, A. P. *Anticancer Res.* 9:1569–1576 (1989); Kamijo, R., et al., *Biochem. Biophys. Res. Comm.* 160:820–827 (1989)). Further, even if deletion of one or more amino acids from the N-terminus or C-terminus of a protein results in modification or loss of one or more biological functions of the protein, other TNF-gamma functional activities may still be retained.

In the present case, since the proteins of the invention are members of the TNF polypeptide family, deletions of N-terminal amino acids up to the leucine residue at position 35 of SEQ ID NO:2 (which corresponds exactly to the leucine residue at position 134 of SEQ ID NO:20) may retain some biological activity such as regulation of growth and differentiation of many types of hematopoietic and endothelial cells. Polypeptides having further N-terminal deletions including the leucine-36 residue in SEQ ID NO:2 (corresponding to leucine-135 in SEQ ID NO:20) would not be expected to retain such biological activities because it is known that this residue in TNF-related polypeptides is in the beginning of the conserved domain required for biological activities.

However, even if deletion of one or more amino acids from the N-terminus of a full-length TNF-gamma polypeptide results in modification or loss of one or more biological functions of the polypeptide, other biological activities may still be retained. Thus, the ability of the shortened polypeptide to induce and/or bind to antibodies which recognize the full-length or mature form of the polypeptide generally will be retained when less than the majority of the residues of the full-length or mature polypeptide are removed from the N-terminus. Whether a particular polypeptide lacking N-terminal residues of a complete polypeptide retains such immunologic activities can readily be determined by routine methods described herein and otherwise known in the art.

Accordingly, the present invention further provides polypeptides having one or more residues deleted from the amino terminus of the amino acid sequence of the TNF-gamma-alpha shown in SEQ ID NO:2, up to the leucine residue at position number 35, and polynucleotides encoding such polypeptides. In particular, the present invention provides polypeptides comprising the amino acid sequence of residues $n^1$-149 of SEQ ID NO:2, where $n^1$ is an integer in the range of −27 to 35, and 35 is the position of the first residue from the N-terminus of the complete TNF-gamma polypeptide (shown in SEQ ID NO:2) believed to be required for regulation of growth and differentiation of many types of hematopoietic and endothelial cells.

In specific embodiments, the invention provides polynucleotides encoding polypeptides comprising, or alternatively, consisting of, the amino acid sequence of residues: −27 to 147, −26 to 147, −25 to 147, −24 to 147, −23 to 147, −22 to 147, −21 to 147, −20 to 147, −19 to 147, −18 to 147, −17 to 147, −16 to 147, −15 to 147, −14 to 147, −13 to 147, −12 to 147, −11 to 147, −10 to 147, −9 to 147, −8 to 147, −7 to 147, −6 to 147, −5 to 147, −4 to 147, to 147, −2 to 147, −2 to 147, −1 to 147, 2 to 147, 3 to 147, 4 to 147, 5 to 147, 6 to 147, 7 to 147, 8 to 147, 9 to 147, 10 to 147, 11 to 147, 12 to 147, 13 to 147, 14 to 147, 15 to 147, 16 to 147, 17 to 147, 18 to 147, 19 to 147, 20 to 147, 21 to 147, 22 to 147, 23 to 147, 24 to 147, 27 to 147, 26 to 147, 27 to 147, 28 to 147, 29 to 147, 30 to 147, 31 to 147, 32 to 147, 33 to 147, 34 to 147, and 35 to 147 of SEQ ID NO:2. Polynucleotides encoding these polypeptides are also encompassed by the invention.

Accordingly, the present invention further provides polypeptides having one or more residues deleted from the amino terminus of the amino acid sequence of the TNF-gamma-beta shown in SEQ ID NO:20, up to the leucine residue at position number 134, and polynucleotides encoding such polypeptides. In particular, the present invention provides polypeptides comprising the amino acid sequence of residues $n^2$-251 of SEQ ID NO:20, where $n^2$ is an integer in the range of 1 to 134, and 135 is the position of the first residue from the N-terminus of the complete TNF-gamma-beta polypeptide (shown in SEQ ID NO:20) believed to be required for regulation of growth and differentiation of many types of hematopoietic and endothelial cells activity of the TNF-gamma-beta polypeptide.

In specific embodiments, the invention provides polynucleotides encoding polypeptides comprising, or alternatively, consisting of, the amino acid sequence of residues: 1 to 251, 2 to 251, 3 to 251, 4 to 251, 5 to 251, 6 to 251, 7 to 251, 8 to 251, 9 to 251, 10 to 251, 11 to 251, 12 to 251, 13 to 251, 14 to 251, 15 to 251, 16 to 251, 17 to 251, 18 to 251, 19 to 251, 20 to 251, 21 to 251, 22 to 251, 23 to 251, 24 to 251, 25 to 251, 26 to 251, 27 to 251, 28 to 251, 29 to 251, 30 to 251, 31 to 251, 32 to 251, 33 to 251, 34 to 251, 35 to 251, 36 to 251, 37 to 251, 38 to 251, 39 to 251, 40 to 251, 41 to 251, 41 to 251, 42 to 251, 43 to 251, 44 to 251, 45 to 251, 46 to 251, 47 to 251, 48 to 251, 49 to 251, 50 to 251, 51 to 251, 52 to 251, 53 to 251, 54 to 251, 55 to 251, 56 to 251, 57 to 251, 58 to 251, 59 to 251, 60 to 251, 61 to 251, 62 to 251, 63 to 251, 64 to 251, 65 to 251, 66 to 251, 67 to 251, 68 to 251, 69 to 251, 70 to 251, 71 to 251, 72 to 251, 73 to 251, 74 to 251, 75 to 251, 76 to 251, 77 to 251, 78 to 251, 79 to 251, 80 to 251, 81 to 251, 82 to 251, 83 to 251, 84 to 251. 85 to 251, 86 to 251, 87 to 251, 88 to 251, 89 to 251, 90 to 251, 91 to 251, 92 to 251, 93 to 251, 94 to 251, 95 to 251, 96 to 251, 97 to 251, 98 to 251, 99 to 251, 100 to 251, 101 to 251, 102 to 251, 103 to 251, 104 to 251, 105 to 251, 106 to 251, 107 to 251, 108 to 251, 109 to 251, 110 to 251, 111 to 251, 112 to 251, 113 to 251, 114 to 251, 115 to 251, 116 to 251, 117 to 251, 118 to 251, 119 to 251, 120 to 251, 121 to 251, 122 to 251, 123 to 251, 124 to 251, 125 to 251, 126 to 251, 127 to 251, 128 to 251, 129 to 251, 130 to 251, 131 to 251, 133 to 251, 134 to 251, and 134 to 251 of SEQ ID NO:20. Polynucleotides encoding these polypeptides are also encompassed by the invention.

As mentioned above, even if deletion of one or more amino acids from the N-terminus of a polypeptide results in modification of loss of one or more biological functions of the polypeptide, other biological activities may still be retained. Thus, the ability of the shortened TNF-gamma-alpha mutein to induce and/or bind to antibodies which recognize the full-length or mature form of the polypeptide generally will be retained when less than the majority of the residues of the full-length or mature polypeptide are removed from the N-terminus. Whether a particular polypeptide lacking N-terminal residues of a complete protein retains such immunologic activities can readily be determined by routine methods described herein and otherwise known in the art. It is not unlikely that a TNF-gamma-alpha mutein with a large number of deleted N-terminal amino acid residues may retain some biological or immunogenic activities. In fact, peptides composed of as few as six TNF-gamma-alpha amino acid residues may often evoke an immune response.

Accordingly, the present invention further provides polypeptides having one or more residues deleted from the amino terminus of the predicted mature amino acid sequence of the TNF-gamma-alpha shown in FIGS. 1A and 1B (SEQ ID NO:2), up to the phenylalanine residue at position number 169 of the sequence shown in FIGS. 1A and 1B (which corresponds to position number 142 of SEQ ID NO:2) and polynucleotides encoding such polypeptides. In particular, the present invention provides polypeptides comprising the amino acid sequence of residues $n^3$-174 of the sequence shown in FIGS. 1A and 1B ($n^3$-147 of SEQ ID NO:2), where $n^3$ is an integer in the range of 1 to 169, and 170 is the position of the first residue from the N-terminus of the complete TNF-gamma-alpha polypeptide believed to be required for at least immunogenic activity of the TNF-gamma-alpha polypeptide.

More in particular, the invention provides polynucleotides encoding polypeptides comprising, or alternatively consisting of, the amino acid sequence of residues of R-2 to L-174; R-3 to L-174; F-4 to L-174; L-5 to L-174; S-6 to L-174; K-7 to L-174; V-8 to L-174; Y-9 to L-174; S-10 to L-174; F-11 to L-174; P-12 to L-174; M-13 to L-174; R-14 to L-174; K-15 to L-174; L-16 to L-174; I-17 to L-174; L-18 to L-174; F-19 to L-174; L-20 to L-174; V-21 to L-174; F-22 to L-174; P-23 to L-174; V-24 to L-174; V-25 to L-174; R-26 to L-174; Q-27 to L-174; T-28 to L-174; P-29 to L-174; T-30 to L-174; Q-31 to L-174; H-32 to L-174; F-33 to L-174; K-34 to L-174; N-35 to L-174; Q-36 to L-174; F-37 to L-174; P-38 to L-174; A-39 to L-174; L-40 to L-174; H-41 to L-174; W-42 to L-174; E-43 to L-174; H-44 to L-174; E-45 to L-174; L-46 to L-174; G-47 to L-174; L-48 to L-174; A-49 to L-174; F-50 to L-174; T-51 to L-174; K-52 to L-174; N-53 to L-174; R-54 to L-174; M-55 to L-174; N-56 to L-174; Y-57 to L-174; T-58 to L-174; N-59 to L-174; K-60 to L-174; F-61 to L-174; L-62 to L-174; L-63 to L-174; I-64 to L-174; P-65 to L-174; E-66 to L-174; S-67 to L-174; G-68 to L-174; D-69 to L-174; Y-70 to L-174; F-71 to L-174; I-72 to L-174; Y-73 to L-174; S-74 to L-174; Q-75 to L-174; V-76 to L-174; T-77 to L-174; F-78 to L-174; R-79 to L-174; G-80 to L-174; M-81 to L-174; T-82 to L-174; S-83 to L-174; E-84 to L-174; C-85 to L-174; S-86 to L-174; E-87 to L-174; I-88 to L-174; R-89 to L-174; Q-90 to L-174; A-91 to L-174; G-92 to L-174; R-93 to L-174; P-94 to L-174; N-95 to L-174; K-96 to L-174; P-97 to L-174; D-98 to L-174; S-99 to L-174; I-100 to L-174; T-101 to L-174; V-102 to L-174; V-103 to L-174; I-104 to L-174; T-105 to L-174; K-106 to L-174; V-107 to L-174; T-108 to L-174; D-109 to L-174; S-110 to L-174; Y-111 to L-174; P-112 to L-174; E-113 to L-174; P-114 to L-174; T-115 to L-174; Q-116 to L-174; L-117 to L-174; L-118 to L-174; M-119 to L-174; G-120 to L-174; T-121 to L-174; K-122 to L-174; S-123 to L-174; V-124 to L-174; C-125 to L-174; E-126 to L-174; V-127 to L-174; G-128 to L-174; S-129 to L-174; N-130 to L-174; W-131 to L-174; F-132 to L-174; Q-113 to L-174; P-114 to L-174; I-135 to L-174; Y-136 to L-174; L-137 to L-174; G-128 to L-174; A-129 to L-174; M-140 to L-174; F-141 to L-174; S-142 to L-174; L-143 to L-174; Q-144 to L-174; E-145 to L-174; G-146 to L-174; D-147 to L-174; K-148 to L-174; L-149 to L-174; M-150 to L-174; V-151 to L-174; N-152 to L-174; V-153to L-174; S-154 to L-174; D-155 to L-174; I-156 to L-174; S-157 to L-174; L-158 to L-174; V-159 to L-174; D-160 to L-174; Y-161 to L-174; T-162 to L-174; K-163 to L-174; E-164 to L-174; D-165 to L-174; K-166 to L-174; T-167 to L-174; F-168 to L-174; and F-169 to L-174 of the TNF-gamma-alpha sequence shown in FIGS. 1A and 1B (the TNF-gamma-alpha amino acid sequence shown in FIGS. 1A and 1B is identical to that in SEQ ID NO:2, however, the numbering scheme differs between the two; the numbering of the above amino acid residues in this case reflects that of FIGS. 1A and 1B). Polynucleotides encoding these polypeptides are also encompassed by the invention.

Accordingly, the present invention further provides polypeptides having one or more residues deleted from the amino terminus of the predicted mature amino acid sequence of the TNF-gamma-beta shown in SEQ ID NO:20, up to the phenylalanine residue at position number 246 and polynucleotides encoding such polypeptides. In particular, the present invention provides polypeptides comprising the amino acid sequence of residues $n^4$-251 of SEQ ID NO:20, where $n^4$ is an integer in the range of 2 to 246, and 247 is the position of the first residue from the N-terminus of the complete TNF-gamma-beta polypeptide believed to be required for at least immunogenic activity of the TNF-gamma-beta protein.

More in particular, the invention provides polynucleotides encoding polypeptides comprising, or alternatively consisting of, the amino acid sequence of residues of A-2 to L-251; E-3 to L-251; D-4 to L-251; L-5 to L-251; G-6 to L-251; L-7 to L-251; S-8 to L-251; F-9 to L-251; G-10 to L-251; E-11 to L-251; T-12 to L-251; A-13 to L-251; S-14 to L-251; V-15 to L-251; E-16 to L-251; M-17 to L-251; L-18 to L-251; P-19 to L-251; E-20 to L-251; H-21 to L-251; G-22 to L-251; S-23 to L-251; C-24 to L-251; R-25 to L-251; P-26 to L-251; K-27 to L-251; A-28 to L-251; R-29 to L-251; S-30 to L-251; S-31 to L-251; S-32 to L-251; A-33 to L-251; R-34 to L-251; W-35 to L-251; A-36 to L-251; L-37 to L-251; T-38 to L-251; C-39 to L-251; C-40 to L-251; L-41 to L-251; V42 to L-251; L-4 to L-251; L-44 to L-251 P-45 to L-251; F-46 to L-251; L-47 to L-251; A-48 to L-251; G-49 to L-251; L-50 to L-251; T-51 to L-251; T-52 to L-251; Y-53 to L-251; L-54 to L-251; L-55 to L-251; V-56 to L-251; S-57 to L-251; Q-58 to L-251; L-59 to L-251; R-60 to L-251; A-61 to L-251; Q-62 to L-251; G-63 to L-251; E-64 to L-251; A-65 to L-251; C-66 to L-251; V-67 to L-251; Q-68 to L-251; F-69 to L-251; Q-70 to L-251; A-71 to L-251; L-72 to L-251; K-73 to L-251; G-74 to L-251; Q-75 to L-251; E-76 to L-251; F-77 to L-251; A-78 to L-251; P-79 to L-251; S-80 to L-251; H-81 to L-251; Q-82 to L-251; Q-83 to L-251; V-84 to L-251; Y-85 to L-251; A-86 to L-251; P-87 to L-251; L-88 to L-251; R-89 to L-251; A-90 to L-251; D-91 to L-251; G-92 to L-251; D-93 to L-251; K-94 to L-251; P-95 to L-251; R-96 to L-251; A-97 to L-251; H-98 to L-251; L-99 to L-251; T-100 to L-251; V-101 to L-251; V-102 to L-251; R-103 to L-251; Q-104 to L-251; T-105 to L-251; P-106 to L-251; T-107 to L-251; Q-108 to L-251; H-109 to L-251; F-110 to L-251; K-111 to L-251; N-112 to L-251; Q-113 to L-251; F-114 to L-251; P-115 to L-251 A-116 to L-251; L-117 to L-251; H-118 to L-251; W-119 to L-251; E-120 to L-251; H-121 to L-251; E-122 to L-251; L-123 to L-251; G-124 to L-251; L-125 to L-251; A-126 to L-251; F-127 to L-251; T-128 to L-251; K-129 to L-251; N-130 to L-251. R-131 to L-251; M-132 to L-251; N-133 to L-251; Y-134 to L-251; T-135 to L-251; N-136 to L-251; K-137 to L-251; F-138 to L-251; L-139 to L-251; L-140 to L-251; I-141 to L-251; P-142 to L-251; E-143 to L-251; S-144 to L-251; G-145 to L-251; D-146 to L-251; Y-147 to L-251; F-148 to L-251; I-149 to L-251; Y-150 to L-251; S-151 to L-251; Q-152 to L-251; V-153 to L-251; T-154 to L-251; F-155 to L-251; R-156 to L-251; G-157 to L-251; M-158 to L-251; T-159 to L-251; S-160 to L-251; E-161 to L-251; C-162 to L-251; S-163 to L-251; E-164 to L-251; I-165 to L-251; R-166 to L-251; Q-167 to L-251; A-168 to L-251; G-169 to L-251; R-170 to L-251; P-171 to L-251; N-172 to L-251; K-173 to L-251; P-174 to L-251; D-175 to L-251; S-176 to L-251; I-177 to L-251; T-178 to L-251; V-179 to L-251;V-180 to L-251; I-181 to L-251; T-182 to L-251 K-183 to L-251; V-184 to L-251; T-185 to L-251; D-186 to L-251; S-187 to L-251; Y-188 to L-251; P-189 to L-251; E-190 to L-251; P-191 to L-251; T-192 to L-251; Q-193 to L-251; L-194 to L-251; L-195 to L-251; M-196 to L-251; G-197 to L-251; T-198 to L-251; K-199 to L-251;S-200 to L-251; V-201 to L-251; C-202 to L-251; E-203 to L-251; V-204 to L-251; G-205 to L-251; S-206 to L-251; N-207 to L-251; W-208 to L-251; F-209 to L-251; Q-210 to L-251; P-211 to L-251; I-212 to L-251; Y-213 to L-251; L-214 to L-251; G-215 to L-251; A-216 to L-251; M-217 to L-251; F-218 to L-251; S-219 to L-251; L-220 to L-251; Q-221 to L-251; E-222 to L-251; G-223 to L-251; D-224 to L-251; K-225 to L-251; L-226 to L-251; M-227 to L-251; V-228 to L-251; N-229 to L-251; V-230 to L-251; S-231 to L-251; D-232 to L-251; I-233 to L-251; S-234 to L-251; L-235 to L-251; V-236 to L-251; D-237 to L-251; Y-218 to L-251; T-239 to L-251; K-240 to L-251; E-241 to L-251; D-242 to L-251; K-243 to L-251; T-244 to L-251; F-245 to L-251; and F-246 to L-251 of the TNF-gamma-beta sequence shown in SEQ ID NO:20. Polynucleotides encoding these polypeptides are also encompassed by the invention.

Similarly, many examples of biologically functional C-terminal deletion muteins are known. For instance, Interferon gamma shows up to ten times higher activities by deleting 8 to 10 amino acid residues from the carboxy terminus of the protein (Dobeli, et al., *J. Biotechnology* 7:199–216 (1988)). Further, several investigators have reported biologically inactive TNF-α muteins in which as few as two amino acids had been removed from the C-terminus (Carlino, J. A., et al., *J. Biol. Chem.* 262:958–961 (1987); Creasey, A. A., et al., *Cancer Res.* 47:145–149 (1987); Sidhu, R. S. and Bollon, A. P. *Anticancer Res.* 9:1569–1576 (1989); Gase, K., et al. *Immunology* 71:368–371 (1990)).

In the present case, since the proteins of the invention are members of the TNF polypeptide family, deletions of C-terminal amino acids up to the leucine at position 146 of SEQ ID NO:2 (which corresponds to the leucine at position 250 of SEQ ID NO:20) may retain some biological activity such as regulation of growth and differentiation of many types of hematopoietic and endothelial cells. Polypeptides having further C-terminal deletions including the leucine residue at position 146 of SEQ ID NO:2 (or the leucine residue at position 250 of SEQ ID NO:20) would not be expected to retain such biological activities because it is known that this residue in TNF-related polypeptides is in the beginning of the conserved domain required for biological activities.

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art.

In additional embodiments, the present invention further provides polypeptides having one or more residues removed from the carboxy terminus of the amino acid sequence of the TNF-gamma-alpha shown in SEQ ID NO:2, up to the leucine residue at position 146 of SEQ ID NO:2, and polynucleotides encoding such polypeptides. In particular, the present invention provides polypeptides having the amino acid sequence of residues $-27\text{-}m^1$ of the amino acid sequence in SEQ ID NO:2, where $m^1$ is any integer in the range of 146 to 147, and residue 146 is the position of the first residue from the C-terminus of the complete TNF-gamma-alpha polypeptide (shown in SEQ ID NO:2) believed to be required for regulation of growth and differentiation of many types of hematopoietic and endothelial cells by the TNF-gamma-alpha polypeptide.

More in particular, the invention provides polynucleotides encoding polypeptides having the amino acid sequence of residues -27–146 and -27–147 of SEQ ID NO:2. Polynucleotides encoding these polypeptides also are provided.

The present invention also provides polypeptides having one or more residues removed from the carboxy terminus of the amino acid sequence of the TNF-gamma-beta shown in SEQ ID NO:20, up to the leucine residue at position 250 of SEQ ID NO:20, and polynucleotides encoding such polypeptides. In particular, the present invention provides polypeptides having the amino acid sequence of residues $1\text{-}m^2$ of the amino acid sequence in SEQ ID NO:20, where $m^2$ is any integer in the range of 250 to 251, and residue 249 is the position of the first residue from the C-terminus of the complete TNF-gamma-beta polypeptide (shown in SEQ ID NO:20) believed to be required for regulation of growth and differentiation of many types of hematopoietic and endothelial cells.

More in particular, the invention provides polynucleotides encoding polypeptides having the amino acid sequence of residues 1–250 and 1–251 of SEQ ID NO:20. Polynucleotides encoding these polypeptides also are provided.

The invention also provides polypeptide fragments comprising, or alternatively consisting of, one or more amino acids deleted from both the amino and the carboxyl termini of TNF-gamma-alpha, which may be described generally as having residues $n^1\text{-}m^1$ of SEQ ID NO:2, where n and m are integers as described above. The invention further provides polypeptides having one or more amino acids deleted from both the amino and the carboxyl termini of TNF-gamma-beta, which may be described generally as having residues $n^2\text{-}m^2$ of SEQ ID NO:20, where $n^2$ and $m^2$ are integers as described above.

As mentioned above, even if deletion of one or more amino acids from the C-terminus of a polypeptide results in modification of loss of one or more biological functions of the polypeptide, other biological activities may still be retained. Thus, the ability of the shortened TNF-gamma-alpha mutein to induce and/or bind to antibodies which recognize the full-length or mature of the polypeptide generally will be retained when less than the majority of the residues of the complete or mature polypeptide are removed from the C-terminus. Whether a particular polypeptide lacking C-terminal residues of a full-length polypeptide retains such immunologic activities can readily be determined by routine methods described herein and otherwise known in the art. It is not unlikely that a TNF-gamma-alpha mutein with a large number of deleted C-terminal amino acid residues may retain some biological or immungenic activities. In fact peptides composed of as few as six TNF-gamma-alpha amino acid residues may often evoke an immune response.

Accordingly, the present invention further provides polypeptides having one or more residues deleted from the carboxy terminus of the amino acid sequence of the TNF-gamma-alpha shown in FIGS. 1A and 1B (or in SEQ ID NO:2), up to the serine residue at position number 6 in FIGS. 1A and 1B (or -22 in SEQ ID NO:2), and polynucleotides encoding such polypeptides. In particular, the present invention provides polypeptides comprising the amino acid sequence of residues $1\text{-}m^3$ of SEQ ID NO:2, where $m^3$ is an integer in the range of 6 to 174, and 6 is the position of the first residue from the C-terminus of the complete TNF-gamma-alpha polypeptide believed to be required for at least immunogenic activity of TNF-gamma-alpha.

More in particular, the invention provides polynucleotides encoding polypeptides comprising, or alternatively consisting of, the amino acid sequence of residues M-1 to L-173; M-1 to F-172; M-1 to A-171; M-1 to G-170; M-1 to F-169; M-1 to F-168; M-1 to T-167; M-1 to K-166; M-1 to D-165; M-1 to E-164; M-1 to K-163; M-1 to T-162; M-1 to Y-161; M-1 to D-160; M-1 to V-159; M-1 to L-158; M-1 to S-157; M-1 to I-156; M-1 to D-155; M-1 to S-154; M-1 to V-153; M-1 to N-152; M-1 to V-151; M-1 to M-150; M-1 L-149; M-1 to K-148; M-1 to D-147; M-1 to G-146; M-1 to E-145; M-1 to Q-144; M-1 to L-143; M-1 to S-142; M-1 to F-141; M-1 to M-140; M-1 to A-139; M-1 to G-138; M-1 to L-137; M-1 to Y-136; M-1 to I-135; M-1 to P-134; M-1 to Q-133; M-1 to F-132; M-1 to W-131; M-1 to N-130; M-1 to S-129; M-1 to G-128; M-1 to V-127; M-1 to E-126; M-1 to C-125; M-1 to V-124; M-1 to S-123; M-1 to K-122; M-1 to T-121; M-1 to G-120; M-1 to M-119; M-1 to L-118; M-1 to L-117; M-1 to Q-116; M-1 to T-115; M-1 to P-114; M-1 to E-113; M-1 to P-112; M-1 to Y-111; M-1 to S-110; M-1 to D-109; M-1 to T-108; M-1 to V-107; M-1 to K-106; M-1 to T-105; M-1 to I-104; M-1 to V-103; M-1 to V-102; M-1 to T-101; M-1 to I-100; M-1 to S-99; M-1 to D-98; M-1 to P-97; M-1 to K-96; M-1 to N-95; M-1 to P-94; M-1 to R-93; M-1 to G-92; M-1 to A-91; M-1 to Q-90; M-1 to R-89; M-1 to I-88; M-1 to E-87; M-1 to S-86; M-1 to C-85; M-1 to E-84; M-1 to R-83; M-1 to T-82; M-1 to M-81; M-1 to S-80; M-1 to R-79; M-1 to F-78; M-1 to T-77; M-1 to V-76; M-1 to Q-75; M-1 to S-74; M-1 to Y-73; M-1 to I-72; M-1 to F-71; M-1 to Y-70; M-1 to D-69; M-1 to S-68; M-1 to S-67; M-1 to E-66; M-1 to P-65; M-1 to I-64; M-1 to L-63; M-1 to L-62; M-1 to F-61; M-1 to K-60; M-1 to N-59; M-1 to T-58; M-1 to Y-57; M-1 to N-56; M-1 to M-55; M-1 to R-54; M-1 to N-53; M-1 to K-52; M-1 to T-51; M-1 to F-50; M-1 to A-49; M-1 to L-48; M-1 to G-47; M-1 to L-46; M-1 to E-45; M-1 to H-44; M-1 to E-43; M-1 to W-42; M-1 to H-41; M-1 to L-40; M-1 to A-39; M-1 to P-38; M-1 to F-37; M-1 to Q-36; M-1 to N-35; M-1 to K-34; M-1 to F-33; M-1 to H-32; M-1 to Q-31; M-1 to T-30; M-1 to P-29; M-1 to T-28; M-1 to Q-27; M-1 to R-26; M-1 to V-25; M-1 to V-24; M-1 to P-23; M-1 to F-22; M-1 to V-21; M-1 to L-20; M-1 to F-19; M-1 to L-18; M-1 to I-17; M-1 to L-16; M-1 to K-15; M-1 to R-14; M-1 to M-13; M-1 to P-12; M-1 to F-11; M-1 to S-10; M-1 to Y-9; M-1 to V-8; M-1 to K-7; and M-1 to S-6 of the sequence of the TNF-gamma-alpha sequence shown in FIGS. 1A and 1B (the TNF-gamma-alpha amino acid sequence shown in FIGS. 1A and 1B is identical to that in SEQ ID NO:2, however, the numbering scheme differs between the two; the numbering of the above amino acid residues in this case reflects that of FIGS. 1A and 1B). Polynucleotides encoding these polypeptides also are provided.

The invention also provides polypeptides having one or more amino acids deleted from both the amino and the carboxyl termini of a TNF-gamma-alpha polypeptide, which may be described generally as having residues $n^3$-$m^3$ of SEQ ID NO:2, where $n^3$ and $m^3$ are integers as described above. Polynucleotides encoding the polypeptides are also encompassed by the invention.

The present invention further provides polypeptides having one or more residues deleted from the carboxy terminus of the amino acid sequence of the TNF-gamma-beta shown in SEQ ID NO:20, up to the glycine residue at position number 6, and polynucleotides encoding such polypeptides. In particular, the present invention provides polypeptides comprising the amino acid sequence of residues 1-$m^4$ of SEQ ID NO:20, where $m^4$ is an integer in the range of 6 to 250, and 6 is the position of the first residue from the C-terminus of the complete TNF-gamma-beta polypeptide believed to be required for at least immunogenic activity of the TNF-gamma-beta protein.

More in particular, the invention provides polynucleotides encoding polypeptides comprising, or alternatively consisting of, the amino acid sequence of residues M-1 to L-250; M-1 to F-249; M-1 to A-248; M-1 to G-247; M-1 to F-246; M-1 to F-245; M-1 to T-244; M-1 to K-243; M-1 to D-242; M-1 to E-241; M-1 to K-240; M-1 to T-239; M-1 to Y-238; M-1 to D-237; M-1 to V-236; M-1 to L-235; M-1 to S-234; M-1 to 1-233; M-1 to D-232; M-1 to S-231; M-1 to V-230; M-1 to N-229; M-1 to V-228; M-1 to M-227; M-1 to L-226; M-1 to K-225; M-1 to D-224; M-1 to G-223; M-1 to E-222; M-1 to Q-221; M-1 to L-220; M-1 to S-219; M-1 to F-218; M-1 to M-217; M-1 to A-216; M-1 to G-215; M-1 to L-214; M-1 to Y-213; M-1 to I-212; M-1 to P-211; M-1 to Q-210; M-1 to F-209; M-1 to W-208; M-1 to N-207; M-1 to S-206; M-1 to G-205; M-1 to V-204; M-1 to E-203; M-1 to C-202; M-1 to V-201; M-1 to S-200; M-1 to K-199; M-1 to T-198; M-1 to G-197; M-1 to M-196; M-1 to L-195; M-1 to L-194; M-1 to Q-193; M-1 to T-192; M-1 to P-191; M-1 to E-190; M-1 to P-189; M-1 to Y-188; M-1 to S-187; M-1 to D-186; M-1 to T-185; M-1 to V-184; M-1 to K-183; M-1 to T-182; M-1 to I-181; M-1 to V-180; M-1 to V-179; M-1 to T-178; M-1 to I-177; M-1 to S-176; M-1 to D-175; M-1 to P-174; M-1 to K-173; M-1 to N-172; M-1 to P-171; M-1 to R-170; M-1 to G-169; M-1 to A-168; M-1 to Q-167; M-1 to R-166; M-1 to I-165; M-1 to E-164; M-1 to S-163; M-1 to C-162; M-1 to E-161; M-1 to S-160; M-1 to T-159; M-1 to M-158; M-1 to G-157; M-1 to R-156; M-1 to F-155; M-1 to T-154; M-1 to V-153; M-1 to Q-152; M-1 to S-151; M-1 to Y-150; M-1 to I-149; M-1 to F-148; M-1 to Y-147; M-1 to D-146; M-1 to G-145; M-1 to S-144; M-1 to E-143; M-1 to P-142; M-1 to I-141; M-1 to L-140; M-1 to L-139; M-1 to F-138; M-1 to K-137; M-1 to N-136; M-1 to T-135; M-1 to Y-134; M-1 to N-133; M-1 to M-132; M-1 to R-131; M-1 to N-130; M-1 to K-129; M-1 to T-128; M-1 to F-127; M-1 to A-126; M-1 to L-125; M-1 to G-124; M-1 to L-123; M-1 to E-122; M-1 to H-121; M-1 to E-120; M-1 to W-119; M-1 to H-118; M-1 to L-117; M-1 to A-116; M-1 to P-115; M-1 to F-114; M-1 to Q-113; M-1 to N-112; M-1 to K-111; M-1 to F-110; M-1 to H-109; M-1 to Q-108; M-1 to T-107; M-1 to P-106; M-1 to T-105; M-1 to Q-104; M-1 to R-103; M-1 to V-102; M-1 to V-101; M-1 to T-100; M-1 to L-99; M-1 to H-98; M-1 to A-97; M-1 to R-96; M-1 to P-95; M-1 to K-94; M-1 to D-93; M-1 to G-92; M-1 to D-91; M-1 to A-90; M-1 to R-89; M-1 to L-88; M-1 to P-87; M-1 to A-86; M-1 to Y-85; M-1 to V-84; M-1 to Q-83; M-1 to Q-82; M-1 to H-81; M-1 to S-80; M-1 to P-79; M-1 to A-78; M-1 to F-77; M-1 to E-76; M-1 to Q-75; M-1 to G-74; M-1 to K-73; M-1 to L-72; M-1 to A-71; M-1 to Q-70; M-1 to F-69; M-1 to Q-68; M-1 to V-67; M-1 to C-66; M-1 to A-65; M-1 to E-64; M-1 to G-63; M-1 to Q-62; M-1 to A-61; M-1 to R-60; M-1 to L-59; M-1 to Q-58; M-1 to S-57; M-1 to V-56; M-1 to L-55; M-1 to L-54; M-1 to Y-53; M-1 to T-52; M-1 to T-51; M-1 to L-50; M-1 to G-49; M-1 to A-48; M-1 to L-47; M-1 to F-46; M-1 to P-45; M-1 to L-44; M-1 to L-43; M-1 to V-42; M-1 to L-41; M-1 to C-40; M-1 to C-39; M-1 to T-38; M-1 to L-37; M-1 to A-36; M-1 to W-35; M-1 to R-34; M-1 to A-33; M-1 to S-32; M-1 to S-31; M-1 to S-30; M-1 to R-29; M-1 to A-28; M-1 to K-27; M-1 to P-26; M-1 to R-25; M-1 to C-24; M-1 to S-23; M-1 to G-22; M-1 to H-21; M-1 to E-20; M-1 to P-19; M-1 to L-18; M-1 to M-17; M-1 to E-16; M-1 to V-15; M-1 to S-14; M-1 to A-13; M-1 to T-12; M-1 to E-11; M-1 to G-10; M-1 to F-9; M-1 to S-8; M-1 to L-7; and M-1 to G-6 of the sequence of the TNF-gamma-beta sequence shown in SEQ ID NO:20. Polynucleotides encoding these polypeptides also are provided.

The invention also provides polypeptides having one or more amino acids deleted from both the amino and the carboxyl termini of a TNF-gamma-beta polypeptide, which may be described generally as having residues $n^4$-$m^4$ of SEQ ID NO:20, where $n^4$ and $m^4$ are integers as described above. Polynucleotides encoding these polypeptides are also encompassed by the invention.

Further embodiments of the invention are directed to polypeptide fragments comprising, or alternatively, consisting of, amino acids described by the general formula $m^x$ to $n^x$, where m and n correspond to any one of the amino acid residues specified above for these symbols, respectively, and x represents any integer. Polynucleotides encoding these polypeptides are also encompassed by the invention.

Specific embodiments of the invention are directed to nucleotide sequences encoding a polypeptide consisting of a portion of the complete TNF-gamma-alpha amino acid sequence encoded by the cDNA clone contained in ATCC Deposit No. 75927, where this portion excludes from 1 to about 62 amino acids from the amino terminus of the complete amino acid sequence encoded by the cDNA clone contained in ATCC Deposit No. 75927, or about 1 amino acid from the carboxy terminus, or any combination of the above amino terminal and carboxy terminal deletions, of the complete amino acid sequence encoded by the cDNA clone contained in ATCC Deposit No. 75927. Polynucleotides encoding all of the above deletion mutant polypeptide forms also are provided.

In another embodiment, the invention is directed to a nucleotide sequence encoding a polypeptide consisting of a portion of the complete TNF-gamma-beta amino acid sequence encoded by the cDNA clone contained in ATCC Deposit No. 203055, where this portion excludes from 1 to about 134 amino acids from the amino terminus of the complete amino acid sequence encoded by the cDNA clone contained in ATCC Deposit No. 203055, or excludes a number of amino acids from the amino terminus of the complete amino acid sequence encoded by the cDNA clone contained in ATCC Deposit No. 203055 (where the number is selected from any integer from 1 to 134), or about 1 amino acid from the carboxy terminus, or any combination of the above amino terminal and carboxy terminal deletions, of the complete amino acid sequence encoded by the cDNA clone contained in ATCC Deposit No. 203055. Polynucleotides encoding all of the above polypeptides are also encompassed by the invention.

The invention further provides an isolated TNF-gamma polypeptide comprising an amino acid sequence selected from the group consisting of: (a) the amino acid sequence of the full-length TNF-gamma-alpha polypeptide having the complete amino acid sequence shown in SEQ ID NO:2 (i.e., positions −27 to 147 of SEQ ID NO:2); (b) the amino acid sequence of the full-length TNF-gamma-alpha polypeptide having the complete amino acid sequence shown in SEQ ID NO:2 excepting the N-terminal methionine (i.e., positions −26 to 147 of SEQ ID NO:2); (c) the amino acid sequence of the predicted mature TNF-gamma-alpha polypeptide having the amino acid sequence at positions 1–147 in SEQ ID NO:2 (d) the complete amino acid sequence encoded by the cDNA clone HUVEO91 contained in the ATCC Deposit No. 75927; (e) the complete amino acid sequence excepting the N-terminal methionine encoded by the cDNA clone contained in the ATCC Deposit No. 75927; and (f) the complete amino acid sequence of the predicted mature TNF-gamma polypeptide encoded by the cDNA clone HUVEO91 contained in the ATCC Deposit No. 75927. The polypeptides of the present invention also include polypeptides having an amino acid sequence at least 70% identical, at least 80% identical, more preferably at least 90% identical, and still more preferably 95%, 96%, 97%, 98% or 99% identical to those described in (a), (b), (c), (d), (e) or (f), above, or fragments thereof, as described herein.

The invention further provides an isolated TNF-gamma polypeptide comprising an amino acid sequence selected from the group consisting of: (a) the amino acid sequence of the full-length TNF-gamma-beta polypeptide having the complete amino acid sequence shown in SEQ ID NO:20 (i.e., positions 1 to 251 of SEQ ID NO:20); (b) the amino acid sequence of the full-length TNF-gamma-beta polypeptide having the complete amino acid sequence shown in SEQ ID NO:20 excepting the N-terminal methionine (i.e., positions 2 to 251 of SEQ ID NO:20); (c) the amino acid sequence of the predicted mature TNF-gamma-beta polypeptide having the amino acid sequence at positions 62–251 in SEQ ID NO:20; (d) the complete amino acid sequence encoded by the cDNA clone HEMCZ56 contained in the ATCC Deposit No. 203055; (e) the complete amino acid sequence excepting the N-terminal methionine encoded by the cDNA clone HEMCZ56 contained in the ATCC Deposit No. 203055; and (f) the complete amino acid sequence of the predicted mature TNF-gamma polypeptide encoded by the cDNA clone HEMCZ56 contained in the ATCC Deposit No. 203055. The polypeptides of the present invention also include polypeptides having an amino acid sequence at least 70% identical, at least 80% identical, more preferably at least 90% identical, and still more preferably 95%, 96%, 97%, 98% or 99% identical to those described in (a), (b), (c), (d), (e) or (f), above, or fragments thereof, as described herein. In specific embodiments, these polypeptides are at least 10 amino acids, at least 15 amino acids, at least 20 amino acids, at least 25 amino acids, at least 30 amino acids and more preferably at least 50 amino acids.

By a polypeptide having an amino acid sequence at least, for example, 95% "identical" to a reference amino acid sequence of a TNF-gamma polypeptide is intended that the amino acid sequence of the polypeptide is identical to the reference sequence except that the polypeptide sequence may include up to five amino acid alterations per each 100 amino acids of the reference amino acid of the TNF-gamma polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIGS. 1A and B (SEQ ID NO:2), the amino acid sequence encoded by deposited cDNA clone HUVEO91, or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty= 0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

The polypeptides of the present invention also include the polypeptide of SEQ ID NO:20 (in particular the extracellular domain of the polypeptide) as well as polypeptides which have at least 70% similarity (preferably at least 70% identity) to the polypeptide of SEQ ID NO:20 and more preferably at least 90% similarity (more preferably at least 90% identity) to the polypeptide of SEQ ID NO:20 and still more preferably at least 95% similarity (still more preferably at least 95% identity) to the polypeptide of SEQ ID NO:20 and also include portions of such polypeptides with such portion of the polypeptide generally containing at least 30 amino acids and more preferably at least 50 amino acids.

Further polypeptides of the present invention include polypeptides have at least 70% similarity, at least 90% similarity, more preferably at least 95% similarity, and still more preferably at least 96%, 97%, 98% or 99% similarity to those polypeptides described herein. The polypeptides of the invention also comprise those which are at least 70% identical, at least 80% identical more preferably at least 90% or 95% identical, still more preferably at least 96%, 97%, 98% or 99% identical to the polypeptides disclosed herein. In specific embodiments, such polypeptides comprise at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide. By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482–489, 1981) to find the best segment of similarity between two sequences.

The invention also encompasses fusion proteins in which the full length TNF-gamma polypeptide or fragment, variant, derivative, or analog thereof is fused to an unrelated protein. These fusion proteins can be routinely designed on the basis of the TNF-gamma nucleotide and polypeptide sequences disclosed herein. For example, as one of skill in the art will appreciate, TNF-gamma-alpha and/or TNF-gamma-beta polypeptides and fragments (including epitope-bearing fragments) thereof described herein can be combined with parts of the constant domain of immunoglobulins (IgG), resulting in chimeric (fusion) polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker, et aL, Nature 331:84–86 (1988)). Fusion proteins that have a disulfide-linked dimeric structure due to the IgG part can also be more efficient in binding and neutralizing other molecules than the monomeric TNF-gamma protein or protein fragment alone (Fountoulakis, et al., J. Biochem. 270:3958–3964 (1995)). As an example, one such TNF-gamma-Fc fusion has been produced herein as described above. Additional examples of TNF-gamma fusion proteins that are encompassed by the invention include, but are not limited to, fusion of the TNF-gamma polypeptide sequence to any amino acid sequence that allows the fusion protein to be displayed on the cell surface; or fusions to an enzyme, fluorescent protein, or luminescent protein which provides a marker function.

The polypeptides of the present invention have uses which include, but are not limited to, molecular weight marker on SDS-PAGE gels or on molecular sieve gel filtration columns using methods well known to those of skill in the art.

Functional Activities

The functional activity of TNF-gamma polypeptides, and fragments, variants derivatives, and analogs thereof, can be assayed by various methods.

For example, in one embodiment where one is assaying for the ability to bind or compete with full-length TNF-gamma polypeptide for binding to anti-TNF-gamma antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention.

In another embodiment, where a TNF-ligand is identified, binding can be assayed, e.g., by means well-known in the art. In another embodiment, physiological correlates of TNF-gamma binding to its substrates (signal transduction) can be assayed.

In addition, assays described herein (see Examples 5, 6, and 9–15, and otherwise known in the art may routinely be applied to measure the ability of TNF-gamma polypeptides and fragments, variants derivatives and analogs thereof to elicit TNF-gamma related biological activity (e.g., to inhibit, or alternatively promote, cell proliferation, tumor formation, angiogenesis, NF-κB activation and cell adhesion in vitro or in vivo).

Other methods will be known to the skilled artisan and are within the scope of the invention.

Antibodies

Antibodies that specifically recognize one or more epitopes of TNF-gamma or epitopes of conserved variants of TNF-gamma, or polypeptide fragments of TNF-gamma, are also encompassed by the invention. Thus, the polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, F(ab') fragments, the products of an Fab expression library, anti-idiotypic antibodies, and epitope binding fragments of any of the above. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies have uses which include, but are not limited to, isolation of the polypeptide from tissue expressing that polypeptide and for detection of TNF-gamma in a biological sample, and may be used as part of a diagnostic or prognostic technique whereby patients may be tested for abnormal amounts of TNF-gamma. Such antibodies may also be used in a method of inhibition of TNF-gamma biological activity.

For the production of antibodies, various host animals may be immunized by injection with TNF-gamma polypeptide (e.g., one corresponding to a functional domain of the polypeptide, such as, the extracellular domain). Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein (*Nature* 256:495–497 (1975)); and U.S. Pat. No. 4,376,110), the human B-cell hybridoma technique (Kosbor, et al., *Immunology Today* 4:72 (1983); Cole, et al., *Proc. Natl. Acad. Sci. USA* 80:2026–2030 (1983), and the EBV-hybridoma technique (Cole, et al., Monoclonal Antibodies And Cancer Therapy, Alan R. Liss, Inc., pp. 77–96 (1985)). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison, et al., *Proc. Natl. Acad. Sci.*, 81:6851–6855 (1984); Neuberger, et al., *Nature* 312:604–608 (1984); Takeda, et al., *Nature* 314:452–454 (1985)) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

For in vivo use of anti-TNF-gamma in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art (Morrison, *Science* 229:1202 (1985); Oi, et al, *BioTechniques* 4:214 (1986); Cabilly, et aL, U.S. Pat. No. 4,816,567; Taniguchi, et al, EP 171496; Morrison, et al., EP 173494; Neuberger, et al., WO 8601533; Robinson, et al., WO 8702671; Boulianne, et al, *Nature* 312:643 (1984); Neuberger, et al, *Nature* 314:268 (1985).

Alternatively, techniques described for the production of single chain antibodies (U.S. Pat. No. 4,946,778; Bird, *Science* 242:423–426 (1988); Huston, et al., *Proc. Natl. Acad. Sci. USA* 85:5879–5883 (1988); and Ward, et al., *Nature* 334:544546 (1989)) can be adapted to produce single chain antibodies against TNF-gamma polypeptides. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')2 fragments which can be produced by pepsin digestion of the antibody molecule and the Fab fragments which can be generated by reducing the disulfide bridges of the F(ab')2 fragments. Alternatively, Fab expression libraries may be constructed (Huse, et al., *Science* 246:1275–1281 (1989)) to allow rapid and easy identification of monoclonal Fab fragments with the desired specificity.

Antibodies to the TNF-gamma polypepitde can, in turn, be utilized to generate anti-idiotype antibodies that "mimic" the ObR, using techniques well known to those skilled in the art. (See, e.g., Greenspan & Bona, *FASEB J.* 7(5):437–444; (1989) and Nissinoff, *J. Immunol.* 147(8):2429–2438 (1991)). For example, antibodies which bind to the TNF-gamma extracellular domain and competitively inhibit the binding of ligand to the TNF-gamma can be used to generate anti-idiotypes that "mimic" the TNF-gamma extracellular domain and, therefore, bind and neutralize TNF-gamma ligand. Such neutralizing anti-idiotypes or Fab fragments of such antiidiotypes can be used in therapeutic regimens to neutralize TNF-gamma ligand.

Immune and Circulatory Systems-Related Disorders Diagnosis

The present inventors have discovered that TNF-gamma is expressed in human umbilical vein endothelial cells, induced endothelial cells, macrophages, and substantia nigra tissue. For a number of immune and circulatory systems-related disorders, substantially altered (increased or decreased) levels of TNF-gamma-alpha and/or TNF-gamma-beta gene expression can be detected in immune and circulatory systems tissue or other cells or bodily fluids (e.g., sera, plasma, urine, synovial fluid or spinal fluid) taken from an individual having such a disorder, relative to a "standard" TNF-gamma-alpha and/or TNF-gamma-beta gene expression level, that is, the TNF-gamma-alpha and/or TNF-gamma-beta expression level in immune and circulatory systems tissues or bodily fluids from an individual not having the immune and circulatory systems disorder. Thus, the invention provides a diagnostic method useful during diagnosis of a immune and circulatory systems disorder, which involves measuring the expression level of the gene encoding the TNF-gamma-alpha and/or TNF-gamma-beta protein in immune and circulatory systems tissue or other cells or body fluid from an individual and comparing the measured gene expression level with a standard TNF-gamma-alpha and/or TNF-gamma-beta gene expression level, whereby an increase or decrease in the gene expression level compared to the standard is indicative of an immune and circulatory systems disorder.

In particular, it is believed that certain tissues in mammals with cancer of the immune and circulatory systems express significantly reduced levels of the TNF-gamma-alpha and/or TNF-gamma-beta protein and mRNA encoding the TNF-gamma-alpha and/or TNF-gamma-beta protein when compared to a corresponding "standard" level. Further, it is believed that enhanced levels of the TNF-gamma-alpha and/or TNF-gamma-beta protein can be detected in certain body fluids (e.g., sera, plasma, urine, and spinal fluid) from mammals with such a cancer when compared to sera from mammals of the same species not having the cancer.

Thus, the invention provides a diagnostic method useful during diagnosis of a immune and circulatory systems disorder, including cancers of these systems, which involves measuring the expression level of the gene encoding the TNF-gamma-alpha and/or TNF-gamma-beta protein in immune and circulatory systems tissue or other cells or body fluid from an individual and comparing the measured gene expression level with a standard TNF-gamma-alpha and/or TNF-gamma-beta gene expression level, whereby an increase or decrease in the gene expression level compared to the standard is indicative of an immune and circulatory systems disorder.

Where a diagnosis of a disorder in the immune and circulatory systems, including diagnosis of a tumor, has already been made according to conventional methods, the present invention is useful as a prognostic indicator, whereby patients exhibiting depressed TNF-gamma-alpha and/or TNF-gamma-beta gene expression will experience a worse clinical outcome relative to patients expressing the gene at a level nearer the standard level.

By "assaying the expression level of the gene encoding the TNF-gamma-alpha and/or TNF-gamma-beta protein" is intended qualitatively or quantitatively measuring or estimating the level of the TNF-gamma-alpha and/or TNF-gamma-beta protein or the level of the mRNA encoding the TNF-gamma-alpha and/or TNF-gamma-beta protein in a first biological sample either directly (e.g., by determining or estimating absolute protein level or mRNA level) or relatively (e.g., by comparing to the TNF-gamma-alpha and/or TNF-gamma-beta protein level or mRNA level in a second biological sample). Preferably, the TNF-gamma-alpha and/or TNF-gamma-beta protein level or mRNA level in the first biological sample is measured or estimated and compared to a standard TNF-gamma-alpha and/or TNF-gamma-beta protein level or mRNA level, the standard being taken from a second biological sample obtained from an individual not having the disorder or being determined by averaging levels from a population of individuals not having a disorder of the immune and circulatory systems. As will be appreciated in the art, once a standard TNF-gamma-alpha and/or TNF-gamma-beta protein level or mRNA level is known, it can be used repeatedly as a standard for comparison.

By "biological sample" is intended any biological sample obtained from an individual, body fluid, cell line, tissue culture, or other source which contains TNF-gamma-alpha and/or TNF-gamma-beta protein or mRNA. As indicated, biological samples include body fluids (such as sera, plasma, urine, synovial fluid and spinal fluid) which contain free TNF-gamma-alpha and/or TNF-gamma-beta protein, immune and circulatory systems tissue, and other tissue sources found to express complete or mature TNF-gamma-alpha and/or TNF-gamma-beta or a TNF-gamma-alpha and/or TNF-gamma-beta receptor. Methods for obtaining tissue biopsies and body fluids from mammals are well known in the art. Where the biological sample is to include mRNA, a tissue biopsy is the preferred source.

Total cellular RNA can be isolated from a biological sample using any suitable technique such as the single-step guanidinium-thiocyanate-phenol-chloroform method described by Chomczynski and Sacchi (Anal. Biochem. 162:156–159 (1987)). Levels of mRNA encoding the TNF-gamma-alpha and/or TNF-gamma-beta protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Assaying TNF-gamma-alpha and/or TNF-gamma-beta protein levels in a biological sample can occur using antibody-based techniques. For example, TNF-gamma-alpha and/or TNF-gamma-beta protein expression in tissues can be studied with classical immunohistological methods (Jalkanen, M., et al., J. Cell. Biol. 101:976–985 (1985); Jalkanen, M., et al., J. Cell. Biol. 105:3087–3096 (1987)). Other antibody-based methods useful for detecting TNF-gamma-alpha and/or TNF-gamma-beta protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}I$, $^{121}I$), carbon ($^{14}C$), sulfur ($^{35}S$), tritium ($^{3}H$), indium ($^{112}In$), and technetium ($^{99m}Tc$), and fluorescent labels, such as fluorescein and rhodamine, and biotin.

In addition to assaying TNF-gamma-alpha and/or TNF-gamma-beta protein levels in a biological sample obtained from an individual, TNF-gamma-alpha and/or TNF-gamma-beta protein can also be detected in vivo by imaging. Antibody labels or markers for in vivo imaging of TNF-gamma-alpha and/or TNF-gamma-beta protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A TNF-gamma-alpha and/or TNF-gamma-beta protein-specific antibody or antibody fragment which has been labeled with an appropriate detectable imaging moiety, such as a radioisotope (for example, $^{131}$I, $^{112}$In, $^{99m}$Tc), a radioopaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain TNF-gamma-alpha and/or TNF-gamma-beta protein. In vivo tumor imaging is described by Burchiel and coworkers (Chapter 13 in *Tumor Imaging: The Radiochemical Detection of Cancer*, Burchiel, S. W. and Rhodes, B. A., eds. Masson Publishing Inc. (1982)).

Treatment

As noted above, TNF-gamma-alpha and/or TNF-gamma-beta polynucleotides and polypeptides are useful for diagnosis of conditions involving abnormally high or low expression of TNF-gamma-alpha and/or TNF-gamma-beta activities. Given the cells and tissues where TNF-gamma-alpha and/or TNF-gamma-beta is expressed as well as the activities modulated by TNF-gamma-alpha and/or TNF-gamma-beta, it is readily apparent that a substantially altered (increased or decreased) level of expression of TNF-gamma-alpha and/or TNF-gamma-beta in an individual compared to the standard or "normal" level produces pathological conditions related to the bodily system(s) in which TNF-gamma-alpha and/or TNF-gamma-beta is expressed and/or is active.

It is well-known in the art that, in addition to a specific cellular function, cellular receptor molecules may also often be exploited by a virus as a means of initiating entry into a potential host cell. For example, it was recently discovered by Wu and colleagues (*J. Exp. Med.* 185:1681–1691 (1997)) that the cellular chemokine receptor CCR5 functions not only as a cellular chemokine receptor, but also as a receptor for macrophage-tropic human immunodeficiency virus (HIV)-1. In addition, RANTES, MIP-1α, and MIP-1β, which are agonists for the cellular chemokine receptor CCR5, inhibit entry of various strains of HIV-1 into susceptible cell lines (Cocchi, F., et al., *Science* 270:1811–1815 (1995)). Thus, the invention also provides a method of treating an individual exposed to, or infected with, a virus through the prophylactic or therapeutic administration of TNF-gamma-alpha and/or TNF-gamma-beta, or an agonist or antagonist thereof, to block or disrupt the interaction of a viral particle with the TNF-gamma-alpha and/or TNF-gamma-beta receptor and, as a result, block the initiation or continuation of viral infectivity.

The TNF-gamma-alpha and/or TNF-gamma-beta of the present invention binds to the TNF-gamma-alpha and/or TNF-gamma-beta receptor and, as such, is likely to block immuno- and endothelial cell-tropic viral infections. Expression patterns of the cDNA clone encoding the present invention suggests that this molecule is expressed primarily in endothelial cells and select hematopoietic tissues. When considered together, these observations suggest that agonists and antagonists, including a receptor, of TNF-gamma-alpha and/or TNF-gamma-beta may be useful as a method of blocking or otherwise regulating the infectivity of immunotropic viral infections. A non-limiting list of viruses which infect humans and can infect cells of the hematopoietic system includes such retroviruses as HIV-1, HIV-2, human T-cell lymphotropic virus (HTLV)-I, and HTLV-II, as well as other DNA and RNA viruses such as herpes simplex virus (HSV)-1, HSV-2, HSV-6, cytomegalovirus (CMV), Epstein-Barr virus (EBV), herpes samirii, adenoviruses, rhinoviruses, influenza viruses, reoviruses, and the like.

The ability of TNF-gamma-alpha and/or TNF-gamma-beta of the present invention, or agonists or antagonists thereof, to prophylactically or therapeutically block viral infection may be easily tested by the skilled artisan. For example, Simmons and coworkers (Science 276:276–279 (1997)) and Arenzana-Seisdedos and colleagues (*Nature* 383:400 (1996)) each outline a method of observing suppression of HIV-1 infection by an antagonist of the CCR5 chemokine receptor and of the CC chemokine RANTES, respectively, in cultured peripheral blood mononuclear cells. Cells are cultured and infected with a virus, HIV-1 in both cases noted above. An agonist or antagonist of the CC chemokine or its receptor is then immediately added to the culture medium. Evidence of the ability of the agonist or antagonist of the chemokine or cellular receptor is determined by evaluating the relative success of viral infection at 3, 6, and 9 days postinfection.

Administration of a pharmaceutical composition comprising an amount of an isolated TNF-gamma-alpha and/or TNF-gamma-beta, or an agonist or antagonist thereof, of the invention to an individual either infected with a virus or at risk for infection with a virus is performed as described below.

The present invention is also useful for diagnosis or treatment of various immune and circulatory system-related disorders in mammals, preferably humans. Such disorders include tumors (an incomplete list of human tumors includes breast cancer, colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, adenoma, and the like) and tumor metastasis, infections by bacteria, viruses, and other parasites, immunodeficiencies, inflammatory diseases, lymphadenopathy, autoimmune diseases, graft versus host disease, and any disregulation of immune and circulatory systems cell function including, but not limited to, autoimmunity, arthritis, leukemias, lymphomas, immunosuppression, immunity, humoral immunity, inflammatory bowel disease, myelo suppression, and the like.

Since TNF-gamma has been shown to induce activation of cellular NF-κB and c-jun N-terminal kinase (JNK), it is also useful in therapeutically regulating such cellular and immune systemic disorders as tumors and tumor metastases, infections by bacteria, viruses, and other parasites, immunodeficiencies, inflammatory diseases, lymphadenopathy, autoimmune diseases, graft versus host disease, autoimmunity, arthritis, leukemias, lymphomas, immunosuppression, inflammatory bowel disease, myelosuppression, and related sequelae.

Since TNF-gamma-alpha and TNF-gamma-beta belong to the TNF superfamily, they also also modulate angiogenesis. In addition, since TNF-gamma-alpha and/or TNF-gamma-beta inhibit immune cell functions, it will have a wide range of anti-inflammatory activities. TNF-gamma-alpha and/or TNF-gamma-beta may be employed as an antineovascularizing agent to treat solid tumors by stimulating the invasion and activation of host defense cells, e.g., cytotoxic T-cells and macrophages and by inhibiting the angiogenesis of tumors. Those of skill in the art will recognize other non-cancer indications where blood vessel proliferation is not wanted. They may also be employed to enhance host defenses against resistant chronic and acute infections, for example, myobacterial infections via the attraction and activation of microbicidal leukocytes. TNF-gamma-alpha and/or TNF-gamma-beta may also be employed to inhibit T-cell proliferation by the inhibition of IL-2 biosynthesis for the treatment of T-cell mediated autoimmune diseases and lymphocytic leukemias. TNF-gamma-alpha and/or TNF-gamma-beta may also be employed to stimulate wound healing, both via the recruitment of debris clearing and connective tissue promoting inflammatory cells. In this same manner, TNF-gamma-alpha and/or TNF-gamma-beta may also be employed to treat other fibrotic disorders, including liver cirrhosis, osteoarthritis and pulmonary fibrosis. TNF-gamma-alpha and/or TNF-gamma-beta also increases the presence of eosinophils which have the distinctive function of killing the larvae of parasites that invade tissues, as in schistosomiasis, trichinosis and ascariasis. TNF-gamma-alpha and/or TNF-gamma-beta may also be employed to regulate hematopoiesis, by regulating the activation and differentiation of various hematopoietic progenitor cells, for example, to release mature leukocytes from the bone marrow following chemotherapy, i.e., in stem cell mobilization. TNF-gamma-alpha and/or TNF-gamma-beta may also be employed to treat sepsis.

In a similar fashion, TNF-gamma-alpha and/or TNF-gamma-beta may be used to treat rheumatoid arthritis (RA) by inhibiting the increase in angiogensis or the increase in endothelial cell proliferation required to sustain an invading pannus in bone and cartilage as is often observed in RA. Endothelial cell proliferation is increased in the synovia of RA patients as compared to patients with osteoarthritis (OA) or unaffected individuals. Neovascularization is needed to sustain the increased mass of the invading pannus into bone and cartilage. Inhibition of angiogenesis is associated with a significant decrease in the severity of both early and chronic arthritis in animal models.

It will also be appreciated by one of ordinary skill that, since the TNF-gamma-alpha and/or TNF-gamma-beta proteins of the invention are members of the TNF family the mature secreted form of the protein may be released in soluble form from the cells which express TNF-gamma by proteolytic cleavage. Therefore, when TNF-gamma-alpha and/or TNF-gamma-beta mature form or soluble extracellular domain is added from an exogenous source to cells, tissues or the body of an individual, the protein will exert its physiological activities on its target cells of that individual. Also, cells expressing this type II transmembrane protein may be added to cells, tissues or the body of an individual and these added cells will bind to cells expressing receptor for TNF-gamma-alpha and/or TNF-gamma-beta, whereby the cells expressing TNF-gamma-alpha and/or TNF-gamma-beta can cause actions (e.g. regulation of endothelial cell growth and regulation) on the receptor-bearing target cells.

Therefore, it will be appreciated that conditions caused by a decrease in the standard or normal level of TNF-gamma-alpha and/or TNF-gamma-beta activities in an individual, particularly disorders of the immune and circulatory systems, can be treated by administration of TNF-gamma-alpha and/or TNF-gamma-beta polypeptide (in the form of the mature protein). Thus, the invention also provides a method of treatment of an individual in need of an increased level of TNF-gamma-alpha and/or TNF-gamma-beta activity comprising administering to such an individual a pharmaceutical composition comprising an amount of an isolated TNF-gamma-alpha and/or TNF-gamma-beta polypeptide of the invention, particularly a mature form of the TNF-gamma-alpha and/or TNF-gamma-beta protein of the invention, effective to increase the TNF-gamma-alpha and/or TNF-gamma-beta activity level in such an individual.

Figure 7A:
FIG. 7A consists of photographs of WEHI 164 cells which are untreated (FIG. 7Aa) and after exposure to TNF-α (FIG. 7Ab), TNF-gamma (FIG. 7Ac), and TNF-β (FIG. 7Ad). Cells which have an elongated non-round morphology have been lysed. The various TNF molecules were added at a concentration of approximately 0.5 $\mu$g/ml. Photographs were taken 72 hours after addition of the various TNF molecules.
Figure 7A:
Figure 7A:
Figure 7A:
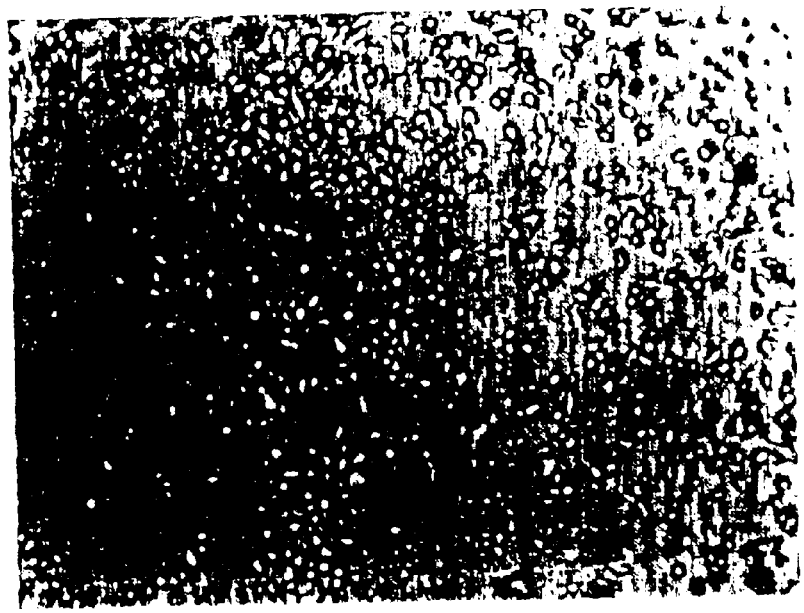
Figure 7B:
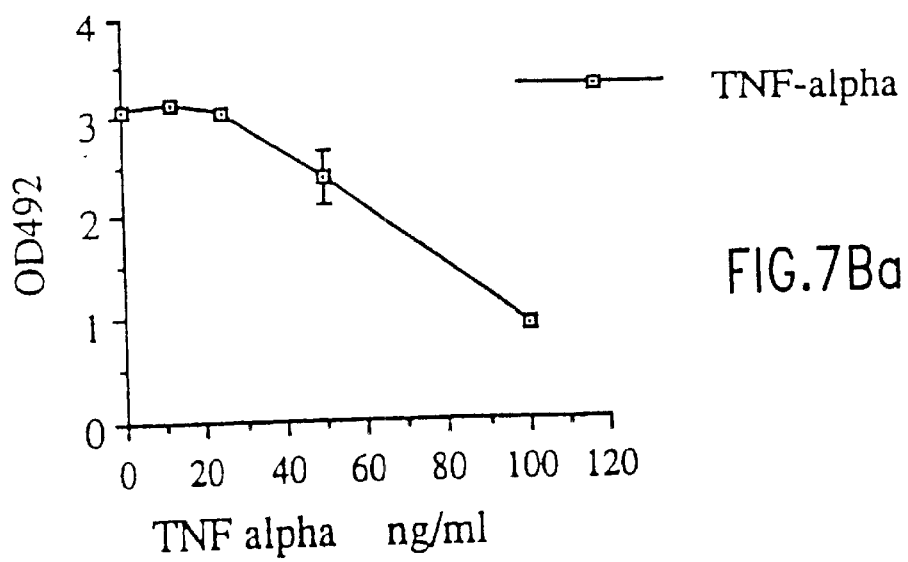
FIG. 7B illustrates the ability of TNF-gamma (FIG. 7Bc) in comparison to TNF-α (FIG. 7Ba) and TNF-β (FIG. 7Bb) to inhibit WEHI 164 cell growth.
Figure 7B:
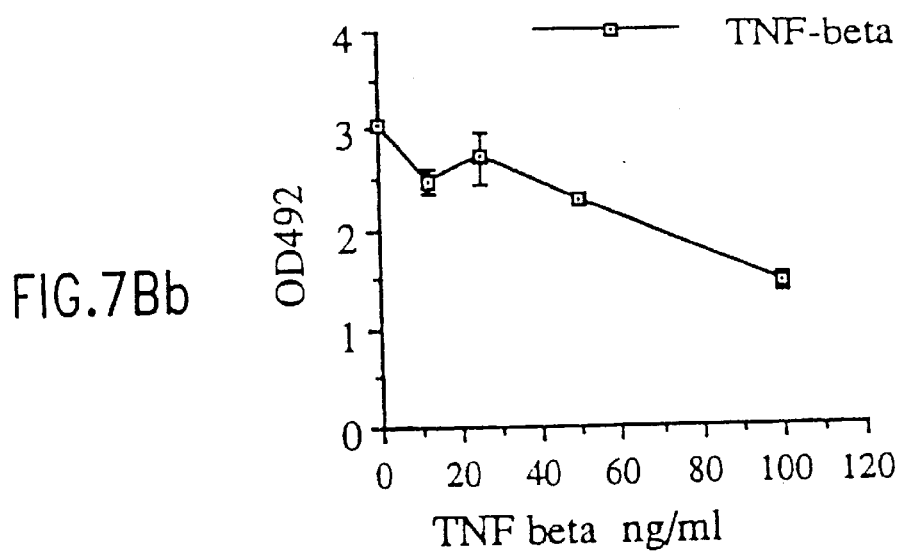
Figure 7B:
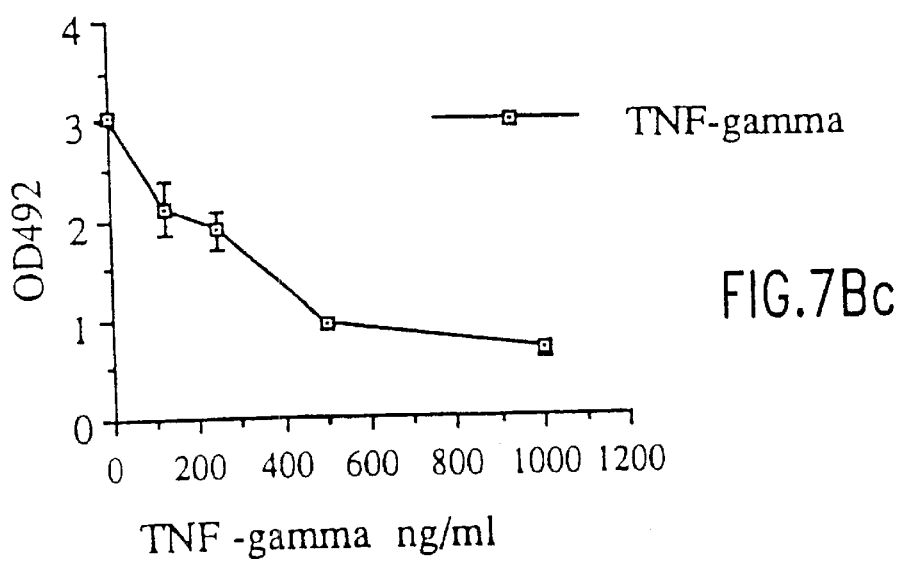
Figure 8B:
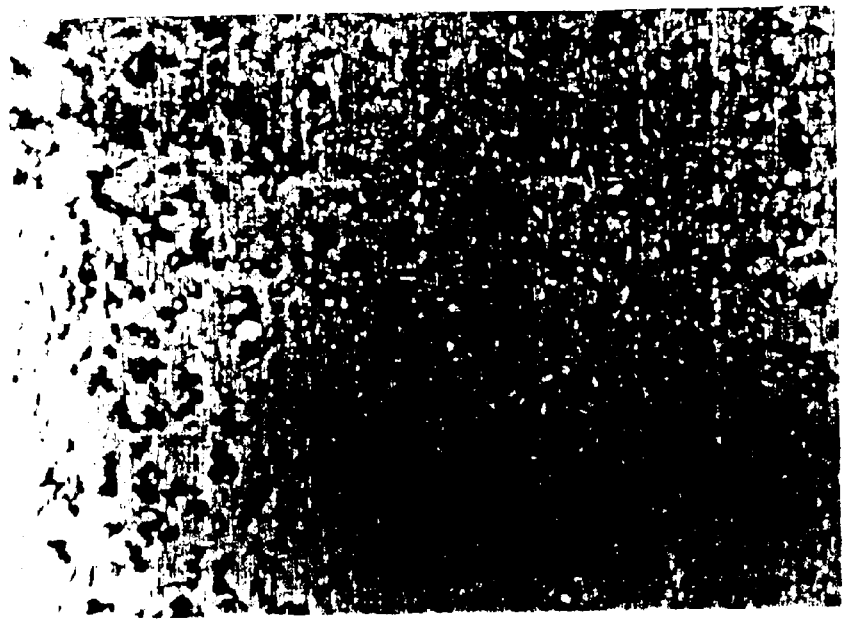
FIG. 8 illustrates the ability of recombinant TNF-α (FIG. 8B), TNF-β (FIG. 8D), and TNF-gamma (FIG. 8C) to induce morphological change in L929 cells with respect to untreated L929 cells (FIG. 8A). The morphology change is indicated by dark round cells. Cells were treated with the various recombinant TNF molecules (produced in *E. coli*) at approximately 0.5 µg/ml. The photographs were taken 72 hours after the addition of the various TNF molecules. The morphology change indicates that the cells have been killed.
Figure 8A:
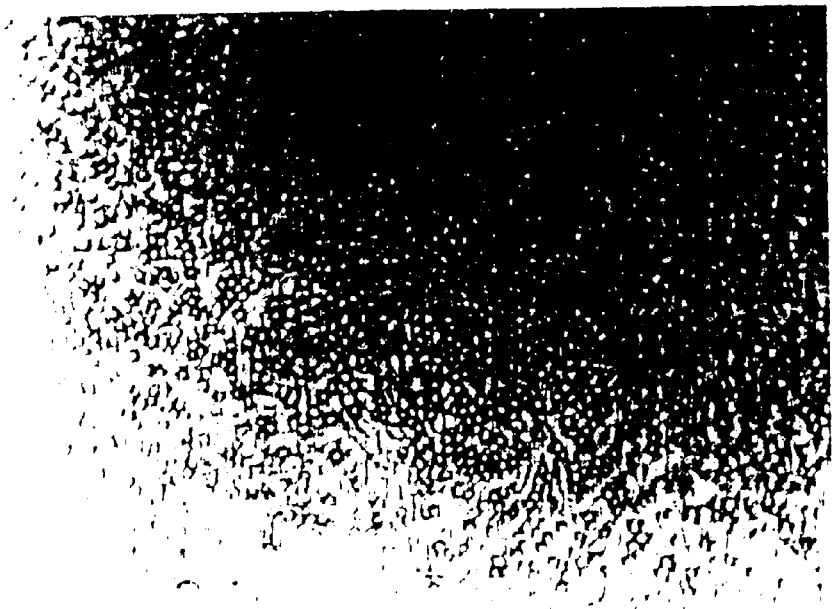
Figure 8D:
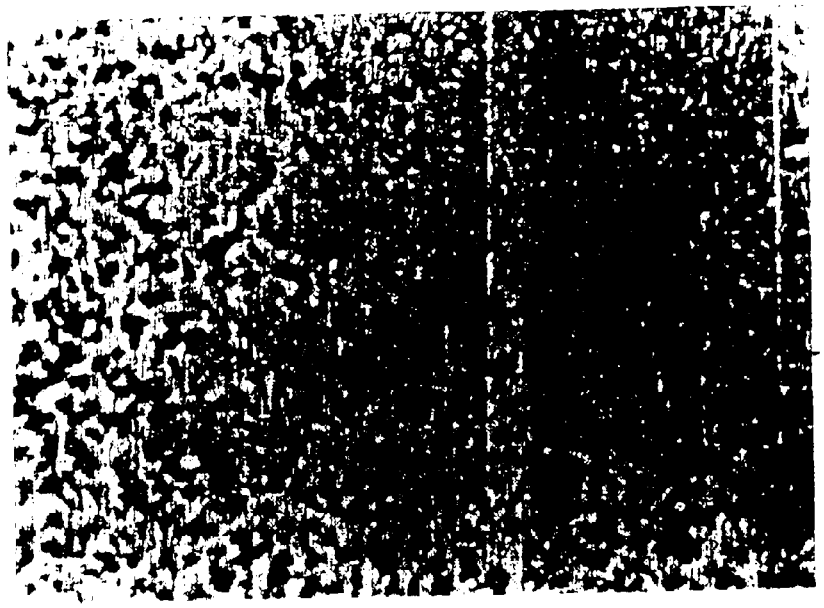
Figure 8C:
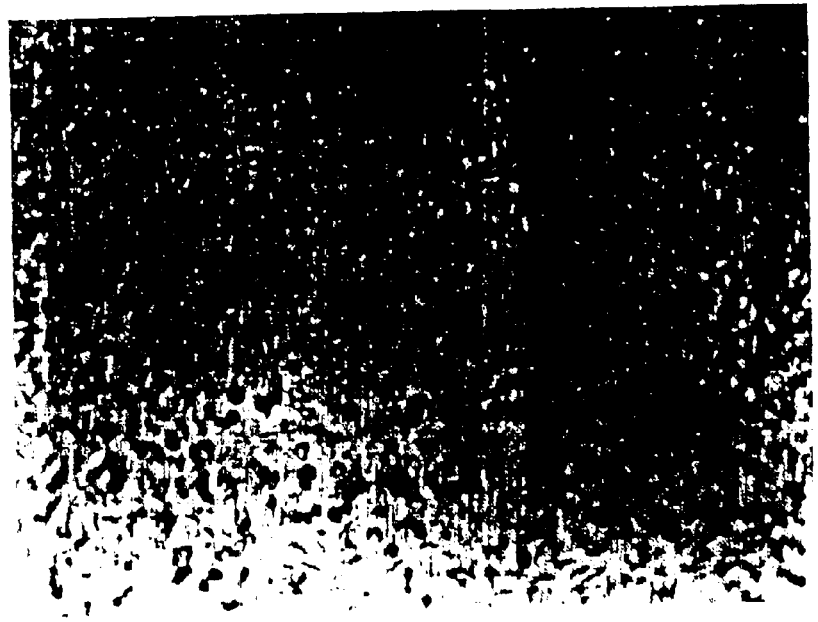
Figure 12:
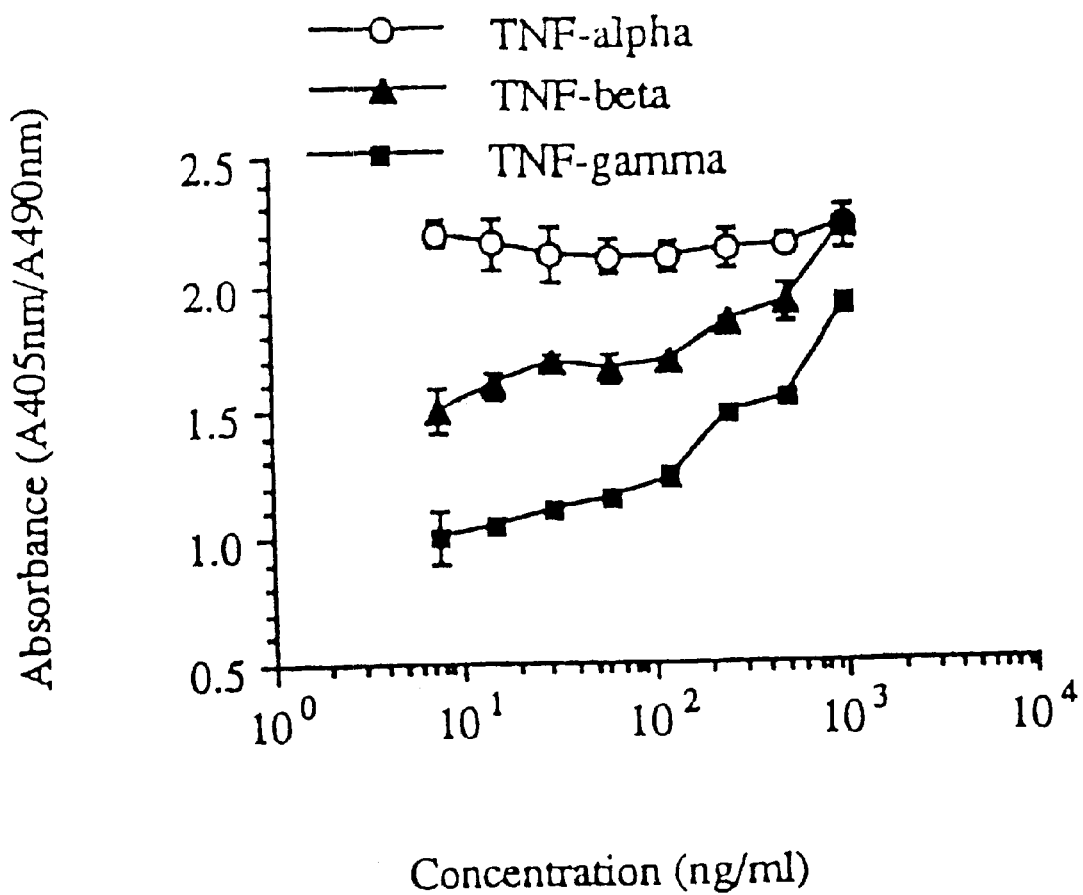
FIG. 12 illustrates the ability of recombinant TNF-gamma (represented by squares), TNF-α (represented by circles), and TNF-β (represented by triangles) to induce WEHI 164 cell death. Cell death is inversely proportional to the ratio of absorbance at 405 nm to that at 490 nm).

The TNF-gamma-alpha and/or TNF-gamma-beta polypeptide of the present invention may be employed to inhibit tumor cell growth or neoplasia. The TNF-gamma-alpha and/or TNF-gamma-beta polypeptide may be responsible for tumor destruction through apoptosis which is characterized by membrane blebbing (zeiosis), condensation of cytoplasma and the activation of an endogeneous endonuclease (FIG. 12). As shown in Table 1, TNF-gamma has strong cytotoxic activity for the cell lines tested which have abnormal cellular proliferation and regulation, for example the fibrosarcoma and carcinoma cell line. This is also illustrated in FIGS. 7A, 7B, and 8 where it is shown that TNF-gamma has the ability to inhibit L929 and WEHI 164 cell growth through cytotoxic activity. WEHI 164 cells are mouse fibrosarcoma cells. A preferable method of administering the TNF-gamma is by injection directly into the tumor.

The cell adhesion activity of TNF-gamma may be employed for wound healing. As shown in Table 1 and FIG. 9, TNF-gamma has a strong endothelial cell proliferation effect which is an indication that TNF-gamma plays a role in wound healing. TNF-gamma's cell adhesive effects may also play a role in wound healing.

TNF-gamma may also be employed to treat diseases which require growth promotion activity, for example, restenosis. As stated above, TNF-gamma is shown to have strong proliferation effects on endothelial cell growth. Accordingly, TNF-gamma may also be employed to regulate hematopoiesis and endothelial cell development.

The TNF-gamma polypeptide, through its ability to stimulate the activation of T-cells, is an important mediator of the immune response. Accordingly, this polypeptide may be used to stimulate an immune response against a variety of parasitic, bacterial and viral infections. TNF-gamma may lyse virus-infected cells and, therefore be employed to arrest HIV infected cells.

The TNF-gamma polypeptide may also be employed to treat autoimmune diseases such as Type I diabetes by enhancing the T-cell proliferative response.

TABLE 1

Summary of TNF-gamma activity

| Cell lines | Source and type | Cyto-toxicity | Pro-liferation | Diff-erentiation | Adhesion |
|---|---|---|---|---|---|
| L929 | mouse fibroblast | + | – | – | – |
| WEHI 164 | mouse fibrosarcoma | +++ | – | – | – |
| NRK-54E | rat kidney epithelial-like | + | – | – | – |
| THP-1 | human monocytic leukemia | + | – | ++ | ++ |
| HL-60 | human promyelocytic leukemia | – | – | – | ++ |

TABLE 1-continued

Summary of TNF-gamma activity

| Cell lines | Source and type | Cyto-toxicity | Pro-liferation | Diff-erentiation | Adhesion |
|---|---|---|---|---|---|
| Raji | human Burkitt lymphoma | – | – | – | – |
| Jurkat | human T-cell | ++ | – | – | – |
| Primary | lymphoma HUVEC | – | ++ | – | ? |
| Primary | human aterial endothelial | +* | ++ | – | ? |
| A-431 | human epidermoid carcinoma | ++ | – | – | – |
| 293 | human embryonal kidney | – | ++ | – | – |

Legend:
*At high dose only. The numbers of "+" indicate the relative level of activities. "–" indicates no detected activity at the concentration range tested.

Figure 10:
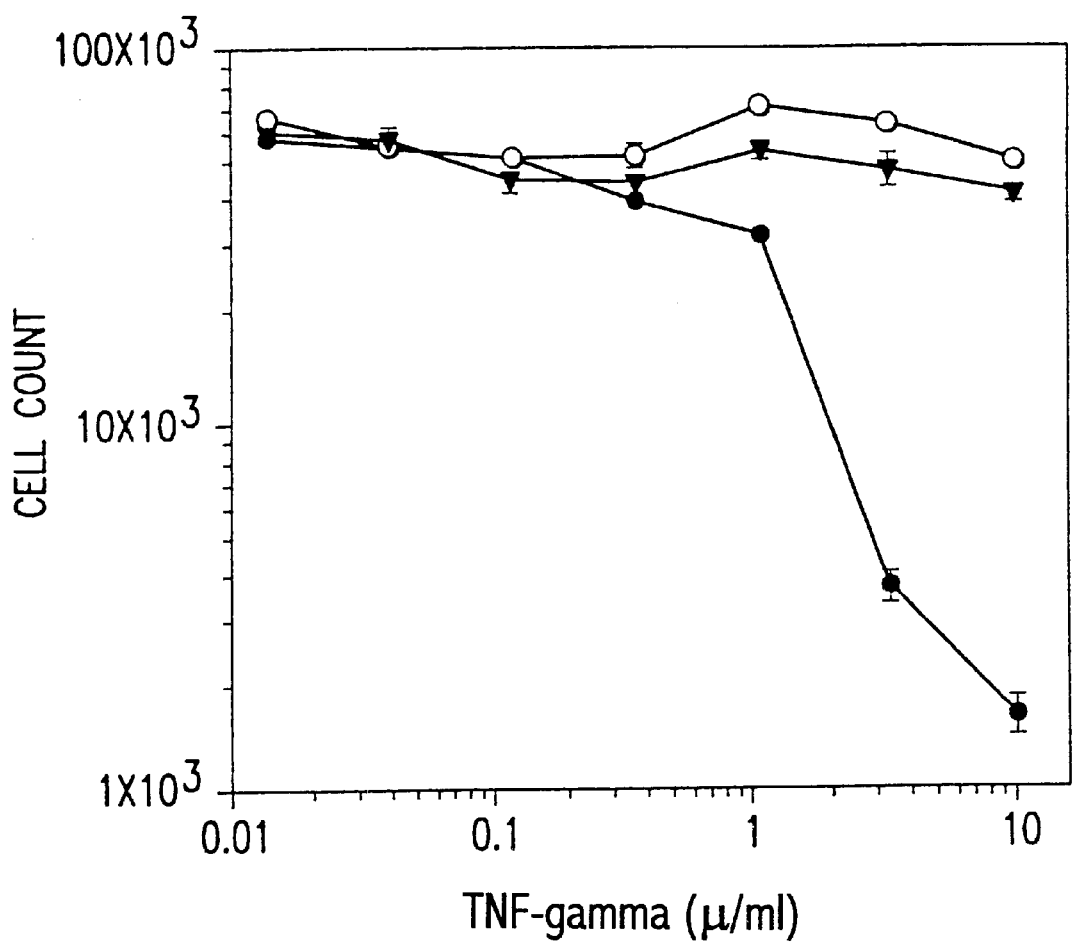
FIG. 10 shows the effect of TNF-gamma on the proliferation of endothelial cell and breast cancer cells. The number of cells are plotted against TNF-gamma concentration as indicated (TNF-gamma is designated "VEGI" in this figure). Inhibition of the growth of adult bovine aortic endothelial (ABAE) cells (dark circles), but not that of MDA-MB-231 (dark triangles) or MDA-MB-435 (open circles) cells. is shown. The cells were seeded at $2 \times 10^3$ cells/well in triplicate in 24-well plates. The ABAE cell culture media contained IMEM (Life Technologies, Inc., Rockville, Md.) supplemented with 10% FCS and (1 ng/ml) FGF-2. The cultures were maintained at 37° C., 5% $CO_2$, for 6 days. The cells were then trypsinized, and the number of cells determined by using a Coulter counter. One-fifth of the total number of recovered ABAE cells is shown in order to normalize the comparison with the MDA-MB-231 and MDA-MB-435 cells.

TNF-gamma may be used to inhibit the proliferation of enodothelial cells, for example, aortic endothelial cells. As illustrated in FIG. 10, at concentrations of up to 10 µg/ml, TNF-gamma can nearly completely inhibit the growth of endothelial cells while having no apparent effect on the growth of human breast cancer cells. As a result, TNF-gamma can be used to treat diseases and disorders in which inhibition of endothelial cell growth is advantageous. Inhibiting the growth of enodthelial cells is desirable in the treatment of many types of cancers which depend on the generation of new blood vessels to support growth of the tumor. TNF-gamma can be used to inhibit the growth of such tumors by inhibiting the growth of enodothelial cells which are a major cellular component of the blood vessel. Evidence of the ability of TNF-gamma to be effectively used in this fashion is presented in FIGS. 16A and 16B. These experiments are discussed in greater detail below.

In particular, TNF-gamma can be used to regulate endothelial cell growth when endothelial cells have already begun proliferating. Such a situation may when angiogenesis is occuring as a tumor-supporting mechanism as described above. Endogenous TNF-gamma expression is reduced in proliferating cultures of endothelial cells, whereas the expression of endogenous TNF-gamma is enhanced in quiescent endothelial cell cultures (FIG. 4). As a result, it is preferable to use TNF-gamma of the present invention to reduce the rate of cell growth in cultures of proliferating endothelial cells, for example, during the increase in size of a tumor in a cancerous state.

Figure 14:
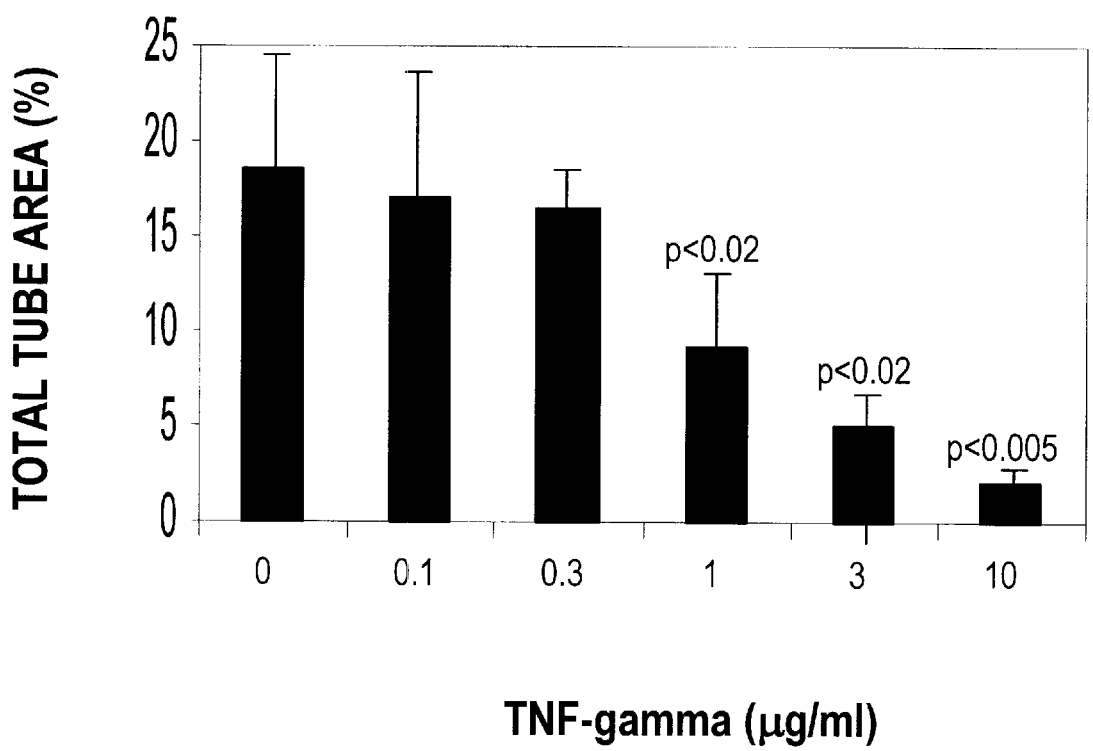
FIG. 14 demonstrates the effect of TNF-gamma on the ability of ABAE cells to form capillary-like tubes on collagen gels. The ability of recombinant TNF-gamma (residues 12–147 as shown in SEQ ID NO:2 and designated "VEGI" in this figure) to inhibit the formation of capillary-like tubes by ABAE cells is shown. The p-values (t-test) given above the columns are obtained by comparing the extent of the capillary-like tube formation by ABAE cells in the presence of various concentrations of TNF-gamma, as indicated, to that when TNF-gamma is absent from the culture media.
Figure 15:
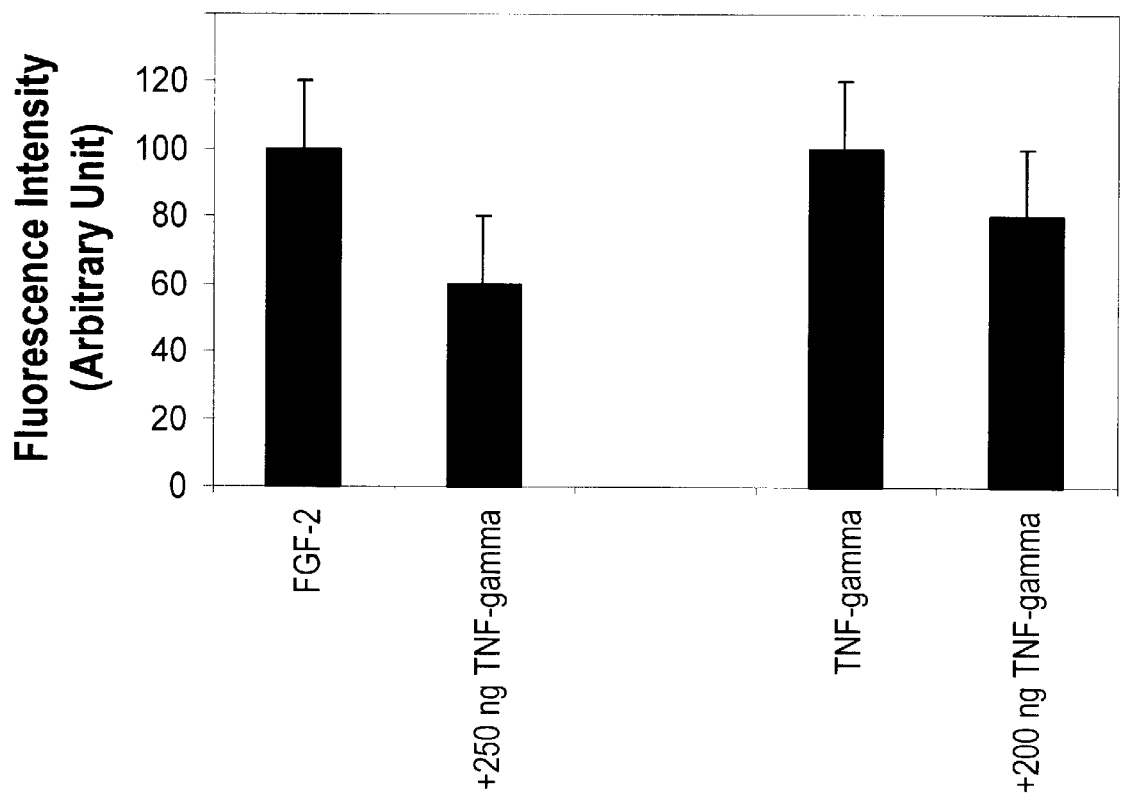
FIG. 15 shows the inhibition of angiogenesis in collagen gels placed on chicken embryonic chorioallantoic membrane (CAM) by TNF-gamma. The growth of new capillary vessels into collagen gel pellets placed on the CAM was induced by either FGF-2 (100 ng) or VEGF (250 ng). The extent of angiogenesis in the gels was determined by evaluation of the fluorescence intensity of FITC-dextran injected into the CAM circulation. Inhibition of the capillary vessel growth by the recombinant TNF-gamma (designated "VEGI" in this figure), as indicated by a lower value than 100, is shown. The experiment was carried out in triplicate.

TNF-gamma of the present invention has been used to reduce the formation of capillary-like tubular structures formed by endothelial cells in vitro. As illustrated in FIG. 14, TNF-gamma of the present invention can be used to inhibit the formation of endothelial cells organized into capillary-like tubular structures in response to angiogenic factors such as FGF-2. Furthermore, isolated TNF-gamma of the present invention can also be used to inhibit the growth and organization of endothelial cells into capillary vessels in a modified chicken embryo chorioallantoic membrane (CAM), as shown in FIG. 15. As a result, TNF-gamma of the present invention can be used to inhibit the formation of capillaries or capillary-like structures from endothelial cells in vitro.

TNF-gamma of the present invention can be used as an anti-cancer agent. As illustrated in FIG. 16, TNF-gamma was used to inhibit the growth of human breast cancer cells in a xenograft tumor model. Despite the high tumorigenicity of these cells, treatment with TNF-gamma of the present invention resulted in a marked inhibition of the growth of the xenograft tumors. TNF-gamma, or a mutein thereof, of the present invention, can be used to treat a number of cancers including, but not limited to, breast cancer, colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, adenoma, and the like.

The polynucleotides and polypeptides of the present invention may be employed as research reagents and materials for discovery of treatments and diagnostics to human disease.

This invention provides a method for identification of the receptor for TNF-gamma. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to TNF-gamma, and a cDNA library created from this RNA is divided into pools and used to transfect COS cells or other cells that are not responsive to TNF-gamma. Transfected cells which are grown on glass slides are exposed to labeled TNF-gamma. TNF-gamma can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clone that encodes the putative receptor.

As an alternative approach for receptor identification, labeled TNF-gamma can be photoaffinity-linked with cell membrane or extract preparations that express the receptor molecule. Cross-linked material is resolved by PAGE and exposed to X-ray film. The labeled complex containing the TNF-gamma-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

TNF-gamma does not bind significantly to two soluble TNF receptors, sTNF-RI (p55) and sTNF-RII (p75). Accordingly, TNF-gamma may have activities inclusive of and additional to known TNF proteins (see FIG. 13).

Formulations

The TNF-gamma polypeptide composition will be formulated and dosed in a fashion consistent with good medical practice, taking into account the clinical condition of the individual patient (especially the side effects of treatment with TNF-gamma polypeptide alone), the site of delivery of the TNF-gamma polypeptide composition, the method of administration, the scheduling of administration, and other factors known to practitioners. The "effective amount" of TNF-gamma polypeptide for purposes herein is thus determined by such considerations.

The antagonists may be employed in a composition with a pharmaceutically acceptable carrier, e.g., as hereinafter described.

The TNF-gamma polypeptides and agonists and antagonists of the present invention may be employed in combination with a suitable pharmaceutical carrier. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions of the present invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 g/kg body weight and in most cases they will be administered in an amount not in excess of about 8 mg/Kg body weight per day. In most cases, the dosage is from about 10 g/kg to about 1 mg/kg body weight daily, taking into account the routes of administration, symptoms, etc.

Gene Therapy

The TNF-gamma polypeptides and agonists and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral particle containing RNA encoding a polypeptide of the present invention.

Similarly, cells may be engineered in vivo for expression of a polypeptide in vivo by, for example, procedures known in the art. For example, a producer cell for producing a retroviral particle containing RNA encoding a polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus. Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described by Miller and colleagues (*Biotechniques* 7:980–990 (1989)), or any other promoter (e.g. cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, β-2, β-AM, PA12, T19-14X, VT-19-17-H2, CRE, β-CRIP, GP+E-86, GP+envAm12, and DAN cell lines as described by Miller (*Human Gene Therapy* 1:5–14 (1990)), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Agonists and Antagonists—Assays and Molecules

This invention is also related to a method of screening compounds to identify those which mimic TNF-gamma (agonists) or prevent the effect of TNF-gamma (antagonists). An example of such a method takes advantage of the ability of TNF-gamma to significantly stimulate the proliferation of human endothelial cells in the presence of the comitogen Con A. Endothelial cells are obtained and cultured in 96-well flat-bottomed culture plates (Costar, Cambridge, Mass.) in RPM1 1640 supplemented with 10% heat-inactivated fetal bovine serum (Hyclone Labs, Logan, Utah), 1% L-glutamine, 100 U/ml penicillin, 100 g/ml steptomycin, 0.1% gentamycin (Gibco Life Technologies, Grand Island, N.Y.) in the presence of 2 g/ml of Con-A (Calbiochem, La Jolla, Calif.). Con-A, and the compound to be screened are added to a final volume of 0.2 ml. After 60 h at 37° C., cultures are pulsed with 1 Ci of [$^3$H]thymidine (5 Ci/mmol; 1 Ci=37 BGq; NEN) for 12–18 h and harvested onto glass fiber filters (PhD; Cambridge Technology, Watertown, Mass.). Mean [$^3$H]thymidine incorporation (cpm) of triplicate cultures is determined using a liquid scintillation counter (Beckman Instruments, Irvine, Calif.). Significant [$^3$H]-thymidine incorporation indicates stimulation of endothelial cell proliferation.

Alternatively, the response of a known second messenger system following interaction of TNF-gamma and receptor would be measured and compared in the presence or absence of the compound. Such second messenger systems include but are not limited to, cAMP guanylate cyclase, ion channels or phosphoinositide hydrolysis.

To assay for antagonists, the assay described above is performed, however, in this assay TNF-gamma is added along with the compound to be screened and the ability of the compound to inhibit [$^3$H]thymidine incorporation in the presence of TNF-gamma, indicates that the compound is an antagonist to TNF-gamma. Alternatively, TNF-gamma antagonists may be detected by combining TNF-gamma and a potential antagonist with membrane-bound TNF-gamma receptors or recombinant receptors under appropriate conditions for a competitive inhibition assay. TNF-gamma can be labeled, such as by radioactivity, such that the number of TNF-gamma molecules bound to the receptor can determine the effectiveness of the potential antagonist.

Alternatively, a mammalian cell or membrane preparation expressing the TNF-gamma receptor is incubated with labeled TNF-gamma in the presence of the compound. The ability of the compound to enhance or block this interaction could then be measured.

In another aspect of this embodiment the invention provides a method for identifying a receptor protein or other ligand-binding protein which binds specifically to a TNF-gamma polypeptide (e.g. DR3). For example, a cellular compartment, such as a membrane or a preparation thereof, may be prepared from a cell that expresses a molecule that binds TNF-gamma. The preparation is incubated with labeled TNF-gamma and complexes of TNF-gamma bound to the receptor or other binding protein are isolated and characterized according to routine methods known in the art. Alternatively, the TNF-gamma polypeptide may be bound to a solid support so that binding molecules solubilized from cells are bound to the column and then eluted and characterized according to routine methods.

In the assay of the invention for agonists or antagonists, a cellular compartment, such as a membrane or a preparation thereof, may be prepared from a cell that expresses a molecule that binds TNF-gamma, such as a molecule of a signaling or regulatory pathway modulated by TNF-gamma. The preparation is incubated with labeled TNF-gamma in the absence or the presence of a candidate molecule which may be a TNF-gamma agonist or antagonist. The ability of the candidate molecule to bind the binding molecule is reflected in decreased binding of the labeled ligand. Molecules which bind gratuitously, i.e., without inducing the effects of TNF-gamma on binding the TNF-gamma binding molecule are most likely to be good antagonists. Molecules that bind well and elicit effects that are the same as or closely related to TNF-gamma are agonists.

TNF-gamma-like effects of potential agonists and antagonists may by measured, for instance, by determining activity of a second messenger system following interaction of the candidate molecule with a cell or appropriate cell preparation, and comparing the effect with that of TNF-gamma or molecules that elicit the same effects as TNF-gamma. Second messenger systems that may be useful in this regard include but are not limited to AMP guanylate cyclase, ion channel or phosphoinositide hydrolysis second messenger systems.

Another example of an assay for TNF-gamma antagonists is a competitive assay that combines TNF-gamma and a potential antagonist with membrane-bound TNF-gamma receptor molecules or recombinant TNF-gamma receptor molecules under appropriate conditions for a competitive inhibition assay. TNF-gamma can be labeled, such as by radioactivity, such that the number of TNF-gamma molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing TNF-gamma-induced activities, thereby preventing the action of TNF-gamma by excluding TNF-gamma from binding.

Other potential antagonists include antisense molecules. Antisense technology can be used to control gene expression through antisense DNA or RNA or through triple-helix formation. Antisense techniques are discussed in a number of studies (for example, Okano, *J. Neurochem.* 56:560 (1991); "Oligodeoxynucleotides as Antisense Inhibitors of Gene Expression." CRC Press, Boca Raton, Fla. (1988)). Triple helix formation is discussed in a number of studies, as well (for instance, Lee, et al., *Nucleic Acids Research* 6:3073 (1979); Cooney, et al., *Science* 241:456 (1988); Dervan, et al., *Science* 251:1360 (1991)). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of TNF-gamma. The antisense RNA oligonucleotide hybridizes to the mRNA in vivo and blocks translation of the mRNA molecule into TNF-gamma polypeptide. The oligonucleotides described above can also be delivered to cells such that the antisense RNA or DNA may be expressed in vivo to inhibit production of TNF-gamma protein.

Antibodies specific to TNF-gamma may be used as antagonists by binding to TNF-gamma and preventing it from binding to its receptor. Monoclonal antibodies are particularly effective in this regard. Antibodies specific to the TNF-gamma receptor, however, may mediate distinct cellular responses which tend to agonize the effects of TNF-gamma upon interaction with its receptor.

Potential TNF-gamma antagonists also include TNF-gamma mutants which bind to the TNF-gamma receptor and elicit no second messenger response to effectively block the receptor from its natural ligand. Specifically designed oligonucleotides and small molecules may also bind to the TNF-gamma receptor (e.g., DR3) and block it from TNF-gamma. Examples of small molecules include but are not limited to small peptides or peptide-like molecules.

Another potential TNF-gamma antagonist is a soluble form of the TNF-gamma receptor which binds to TNFgamma and prevents it from interacting with membrane-bound TNF-gamma receptors. In this way, the receptors are not stimulated by TNF-gamma.

Another potential TNF-gamma antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of TNF-gamma. The antisense RNA oligonucleotide hybridizes to the mRNA in vivo and blocks translation of the mRNA molecule into the TNF-gamma polypeptide (Antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of TNF-gamma.

TNF-antagonists may also be employed to treat cachexia which is a lipid clearing defect resulting from a systemic deficiency of lipoprotein lipase which is suppressed by TNF-gamma. The TNF-gamma antagonists are also employed to treat cerebral malaria in which TNF-gamma appears to play a pathogenic role. The antagonists may also be employed to treat rheumatoid arthritis by inhibiting TNF-gamma induced production of inflammatory cytokines such as IL-1 in the synovial cells. When treating arthritis TNF-gamma is preferably injected intra-articularly.

The TNF-gamma antagonists may also be employed to prevent graft rejection by preventing the stimulation of the immune system in the presence of a graft by TNF-gamma.

The TNF-gamma antagonists may also be employed to treat osteoporosis since TNF-gamma may induce bone resorption.

Antagonists to TNF-gamma may also be employed as anti-inflammation agents since TNF-gamma mediates an enhanced inflammatory response.

The antagonists may also be used to treat endotoxic shock also referred to as septic shock. This critical condition results from an exaggerated response to bacterial or other types of infection. This response leads to elevated levels of TNF-gamma which causes shock and tissue injury.

The present invention also relates to a diagnostic assay for detecting altered levels of TNF-gamma protein in various tissues since an over-expression of the proteins compared to normal control tissue samples may detect the presence of a disease or susceptibility to a disease, for example, tumors and cerebral malaria. Assays used to detect levels of TNF-gamma protein in a sample derived from a host are well-known to those of skill in the art and include radioimmunoassays, competitive-binding assays, Western Blot analysis, ELISA assays and "sandwich" assay. An ELISA assay (Coligan, et al., Current Protocols in Immunology, 1(2), Chapter 6, (1991)) initially comprises preparing an antibody specific to the TNF-gamma antigen, preferably a monoclonal antibody. In addition a reporter antibody is prepared against the monoclonal antibody. To the reporter antibody is attached a detectable reagent such as radioactivity, flourescence or in this example a horseradish peroxidase enzyme. A sample is removed from a host and incubated on a solid support, e.g. a polystyrene dish, that binds the proteins in the sample. Any free protein binding sites on the dish are then covered by incubating with a non-specific protein like BSA. Next, the monoclonal antibody is incubated in the dish during which time the monoclonal antibodies attach to any TNF-gamma proteins attached to the polystyrene dish. All unbound monoclonal antibody is washed out with buffer. The reporter antibody linked to horseradish perosxidase is now placed in the dish resulting in binding of the reporter antibody to any monoclonal antibody bound to TNF-gamma. Unattached reporter antibody is then washed out. Peroxidase substrates are then added to the dish and the amount of color developed in a given time preiod is a measurement of the amount of TNF-gamma protein present in a given volume of patient sample when compared against a standard curve.

A competition assay may be employed wherein antibodies specific to TNF-gamma are attached to a solid support and labeled TNF-gamma and a sample derived from the host are passed over the solid support and the amount of label detected, for example by liquid scintillation chromotagraphy, can be correlated to a quantity of TNF-gamma in the sample.

A "sandwich" assay is similar to an ELISA assay. In a "sandwich" assay TNF-gamma is passed over a solid support and binds to antibody attached to a solid support. A second antibody is then bound to the TNF-gamma. A third antibody which is labeled and specific to the second antibody is then passed over the solid support and binds to the second antibody and an amount can then be quantitated.

Gene Mapping

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the sequence is used to rapidly select primers that do not span more than one exon in the genomic DNA. thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Utilizing the techniques described above, the chromosomal location of TNF-gamma was determined with very high confidence to be 9q32. Previous chromosomal mapping studies have linked several developmental defects to loci in this area of chromosome 9.

EXAMPLES

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures, unless otherwise stated. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

Example 1

Bacterial Expression and Purification of TNF-Gamma

Figure 5:
FIG. 5 is a photograph of a polyacrylamide gel electrophoresis analysis of TNF-gamma protein. TNF-gamma was produced by bacterial expression and purified as described in Example 1.

The DNA sequence encoding the full-length TNF-gamma ORF, ATCC Deposit No. 75927, was initially amplified using PCR oligonucleotide primers corresponding to the 5' and 3' sequences of the TNF-gamma protein. Additional nucleotides corresponding to TNF-gamma were added to the 5' and 3' sequences respectively. The 5' oligonucleotide primer is shown as SEQ ID NO:13 and has the sequence 5'-GCG CGG ATC CAC CAT GAG ACG CTT TTT AAG CAA AGT C-3' which contains a Bam HI restriction enzyme site followed by the first 24 nucleotides of TNF-gamma coding sequence starting from the initiating methionine codon. The 3' sequence 5'-CGC GTC TAG ACT ATA GTA AGA AGG CTC CAA AGA AGG-3' (SEQ ID NO:14) contains sequences complementary to an Xba I site and 22 nucleotides of TNF-gamma. The restriction enzyme sites correspond to the restriction enzyme sites in the bacterial expression vector pQE-9 (Qiagen). pQE-9 was then digested with Bam HI and Xba I. The amplified sequences were ligated into pQE-9 and were inserted in frame with the sequence encoding for the histidine tag and the RBS. The ligation mixture was then used to transform an E. coli strain available from Qiagen under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan'). Transformants were identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture was used to inoculate a large culture at a ratio of 1:100 to 1:250. The cells were grown to an optical density 600 (O.D.$_{600}$) of between 0.4 and 0.6. IPTG ("Isopropyl-B-D-thiogalactopyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 M Guanidine HCl (Guanidine HCl concentrations of greater than or equal to 2.5 M were empirically found to resulat in a higher level of purity of recovered recombinant protein). After clarification, solubilized TNF-gamma was purified from this solution by chromatography on a Nickel-Chelate column under conditions that allow for tight binding by proteins containing the 6-His tag (Hochuli, E. et al., J. Chromatography 411:177–184 (1984)). TNF-gamma was further purified by a second run on the Nickel-chelate column. TNF-gamma (90% pure) was eluted from the column in 6 M guanidine HCl pH 5.0 and for the purpose of renaturation was dialyzed in PBS buffer. The expression product was electrophoresed by SDS-PAGE, and the results may be seen in FIG. 5 where lanes labeled "M" contain molecular weight markers; lane 1 is induced cell lysate; lane 2 is uninduced call lysate; lane 3 is the TNF-gamma protein after two Nickel-chelate column purifications; lane 4 is the TNF-gamma protein after 1 column purification.

One of ordinary skill in the art will recognize that bacterial expression vectors other than pQE-9 may also be used to express TNF-gamma. One such preferred bacterial expression vector is pHE4–5. pHE4–5 may be obtained as pHE4–5/MPIFΔ23 plasmid DNA (this construct contains an unrelated insert which encodes an unrelaed ORF). The pHE4–5/MPIFΔ23 plasmid was deposited with the American Type Culture Collection, 10801 University Boulevard Manassas, Va. 20110-2209 on Sep. 30, 1997 (Accession No. 209311). Using the Nde I and Asp 718 restriction sites flanking the unrelated MPIF ORF insert, one of ordinary skill in the art could easily use current molecular biological techniques to replace the unrelated ORF in the pHE4–5/MPIFΔ23 plasmid with the TNF-gamma ORF, or variations thereof, of the present invention.

Example 2

Cloning and Expression of TNF-Gamma Using the Baculovirus Expression System

The DNA sequence encoding the full length TNF-gamma protein, ATCC No. 75927, was amplified using PCR oligonucleotide primers corresponding to the 5' and 3' sequences of the gene: The 5' primer has the sequence 5'-GCG CGG ATC CAC C<u>AT</u> GAG ACG CTT TTT AAG CAA AGT C-3' (SEQ ID NO:15) and contains a Bam HI restriction enzyme site (in bold) followed by 24 nucleotides of the TNF-gamma gene (the initiation codon for translation "ATG" is underlined). The 3' primer has the sequence 5'-CGC GTC TAG ACT ATA GTA AGA AGG CTC CAA AGA AGG-3' (SEQ ID NO:16) and contains the cleavage site for the restriction endonuclease Xba 1 and 22 nucleotides complementary to the 3' non-translated sequence of the TNF-gamma gene. The amplified sequences were isolated from a 1% agarose gel using a commercially available kit ("Geneclean," BIO 101 Inc., La Jolla, Calif.). The fragment was then digested with the endonucleases Bam HI and Xba I and then purified again on a 1% agarose gel. This fragment was designated F2.

The vector pA2 (modification of pVL941 vector, discussed below) was used for the expression of the TNF-gamma protein using the baculovirus expression system (for review see: Summers, M. D. and Smith, G. E. 1987, *A manual of methods for baculovirus vectors and insect cell culture procedures,* Texas Agricultural Experimental Station Bulletin No. 1555). This expression vector contains the strong polyhedrin promoter of the *Autographa californica* nuclear polyhedrosis virus (AcMNPV) followed by the recognition sites for the restriction endonucleases Bam HI and Xba I. The polyadenylation site of the simian virus SV40 is used for efficient polyadenylation. For an easy selection of recombinant virus the beta-galactosidase gene from *E. coli* was inserted in the same orientation as the polyhedrin promoter followed by the polyadenylation signal of the polyhedrin gene. The polyhedrin sequences were flanked at both sides by viral sequences for the cell-mediated homologous recombination of cotransfected wild-type viral DNA. Many other baculovirus vectors could have been used in place of pA2, such as pRG1, pAc373, pVL941 and pAcIM1 (Luckow, V. A. and Summers, M. D., Virology, 170:31–39).

The plasmid was digested with the restriction enzymes Bam HI and Xba I and then dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA was designated V2.

Fragment F2 and the dephosphorylated plasmid V2 were ligated with T4 DNA ligase. *E. coli* XL1 blue cells were then transformed. The sequence of the cloned fragment was confirmed by DNA sequencing.

5 μg of the plasmid pBac TNF-gamma was cotransfected with 1.0 μg of a commercially available linearized baculovirus ("BaculoGold baculovirus DNA", Pharmingen, San Diego, Calif.) using the lipofection method (Felgner et al. Proc. Natl. Acad. Sci. USA, 84:7413–7417 (1987)).

1 μg of BaculoGold virus DNA and 5 μg of the plasmid pBac TNF-gamma were mixed in a sterile well of a microtiter plate containing 50 μl of serum free Grace's medium (Life Technologies Inc., Gaithersburg, Md.). Afterwards, 10 μl Lipofectin plus 90 μl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace' medium without serum. The plate was rocked back and forth to mix the newly added solution. The plate was then incubated for 5 hours at 27° C. After 5 hours, the transfection solution was removed from the plate and 1 ml of Grace's insect medium supplemented with 10% fetal calf serum was added. The plate was put back into an incubator and cultivation continued at 27° C. for four days.

After four days, the supernatant was collected and a plaque assay performed essentially as described by Summers and Smith (supra). As a modification, an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the virus was added to the cells, blue stained plaques were picked with the tip of an Eppendorf pipette. The agar containing the recombinant viruses was then resuspended in an Eppendorf tube containing 200 μl of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 4° C.

Figure 6:
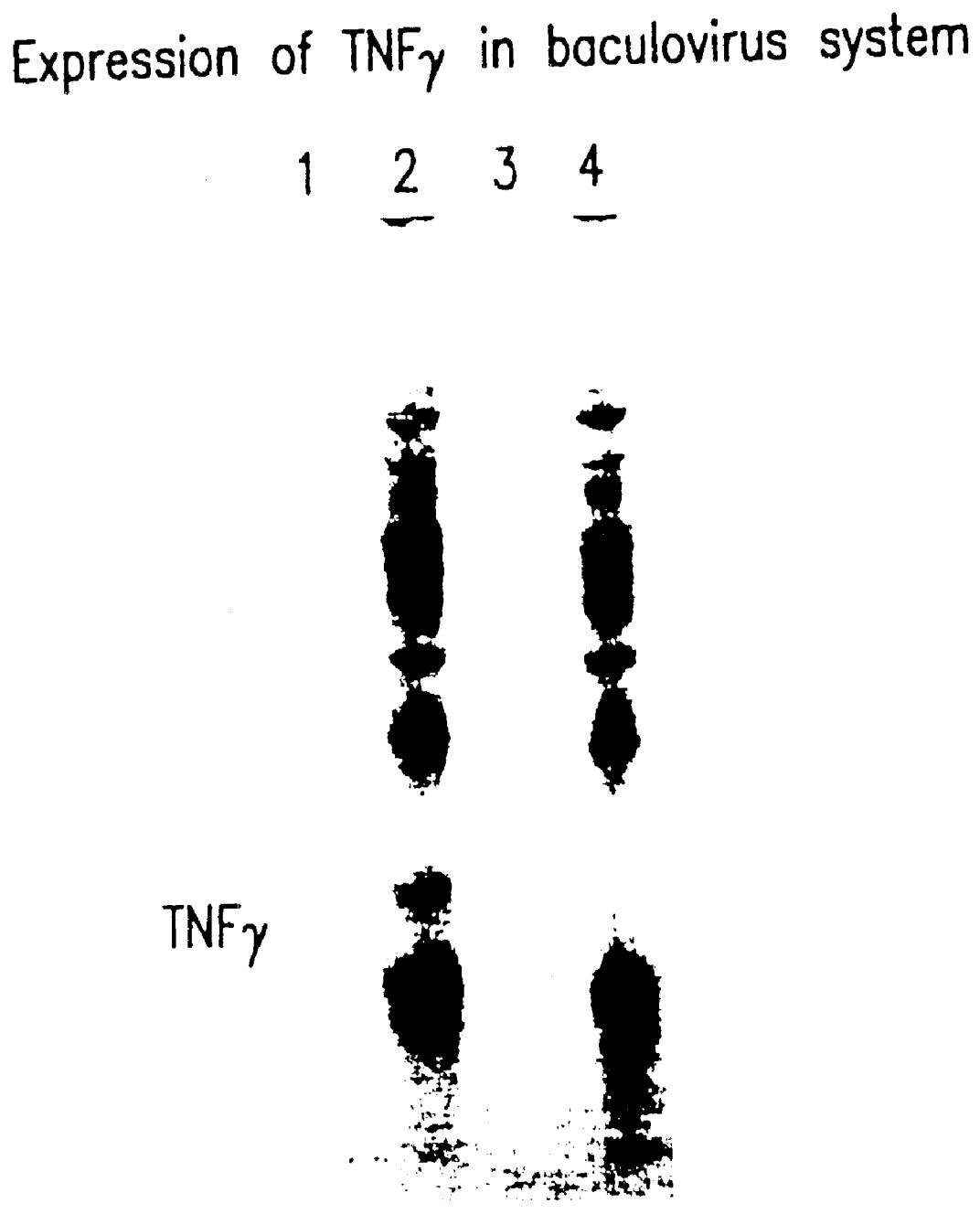

Sf9 cells were grown in Grace's medium supplemented with 10% heat-inactivated FBS. The cells were infected with the recombinant baculovirus V-TNF-gamma at a multiplicity of infection (MOI) of 2. Six hours later the medium was removed and replaced with SF900 II medium minus methionine and cysteine (Life Technologies Inc., Gaithersburg). 42 hours later 5 μCi of [$^{35}$S]-methionine and 5 μCi [$^{35}$S]-cysteine (Amersham) were added. The cells were further incubated for 16 hours before they were harvested by centrifugation and the labeled proteins visualized by SDS-PAGE and autoradiography. FIG. 6 illustrates a gel where lanes 1 and 3 are the medium of the TNF-gamma and control cultures and lanes 2 and 4 are the cell lysates of the TNF-gamma and the control cultures.

Example 3

Expression of Recombinant TNF-Gamma in COS Cells

The expression of plasmid, TNF-gamma-HA is derived from a vector pcDNAI/Amp (Invitrogen) containing: 1) SV40 origin of replication, 2) ampicillin resistance gene, 3) E. coli replication origin, 4) CMV promoter followed by a polylinker region, an SV40 intron, and a polyadenylation site. A DNA fragment encoding the entire TNF-gamma precursor and a hemagglutinin antigen (HA) tag fused in frame to its 3' end was cloned into the polylinker region of the vector. Therefore, the recombinant protein expression is under the direction of the CMV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37, 767). The fusion of HA tag to our target protein allows easy detection of the recombinant protein with an antibody that recognizes the HA epitope.

The plasmid construction strategy is described as follows: The DNA sequence encoding TNF-gamma, ATCC # 75927, was constructed by PCR on the original EST cloned using two primers: the 5' primer (SEQ ID NO:15) contains a Bam HI site followed by 24 nucleotides of TNF-gamma coding sequence starting from the initiation codon; the 3' sequence 5'-CGC TCT AGA TCA AGC GTA GTC TGG GAC GTC GTA TGG ATA GTA AGA AGG CTC CAA AG-3' (SEQ ID NO:17) contains complementary sequences to Xba I site, translation stop codon, HA tag and the last 18 nucleotides of the TNF-gamma coding sequence (not including the stop codon). Therefore, the PCR product contained a Bam HI site, TNF-gamma coding sequence followed by HA tag fused in frame, a translation termination stop codon next to the HA tag, and an Xba I site. The PCR amplified DNA fragment and the vector, pcDNAI/Amp, were digested with Bam HI and Xba I restriction enzymes and ligated together. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant TNF-gamma, COS cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the TNF-gamma HA protein was detected by radiolabelling and immunoprecipitation method. (E. Harlow, D. Lane, Antibodies: A Laboratory Manual, Cold Spring Harbor Laboratory Press, (1988)). Cells were labeled for 8 hours with [$^{35}$S]-S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5; Wilson, I. et al., Id. 37:767 (1984)). Both cell lysate and culture media were precipitated with an HA-specific monoclonal antibody. Precipitated proteins were then analyzed on 15% SDS-PAGE gels.

Example 4

Expression Pattern of TNF-Gamma in Human Tissue

RNA blot analysis was carried out to examine the levels of expression of TNF-gamma in human tissues. Total cellular RNA samples were isolated with RNAzol™ B system (Biotecx Laboratories, Inc. 6023 South Loop East, Houston, Tex. 77033). About 2 μg (for the RNA blot of FIG. 3A) of total RNA isolated from each human tissue specified was separated on 1% agarose-formaldehyde gel and blotted onto a nylon filter (Sambrook, Fritsch, and Maniatis, Molecular Cloning, Cold Spring Harbor Press, (1989)). The labeling reaction was done according to the Stratagene Prime-It kit with 50 ng TNF-gamma cDNA, to produce [$^{32}$P]-labeled TNF-gamma cDNA. The labeled DNA was purified with a Select-G-50 column (5 Prime—3 Prime, Inc. 5603 Arapahoe Road, Boulder, Colo. 80303). The filter was then hybridized with radioactive labeled full-length TNF-gamma gene at 1,000,000 cpm/ml in 0.5 M NaPO$_4$, pH 7.4 and 7% SDS overnight at 65° C. After being washed twice at room temperature and twice at 60° C. with 0.5×SSC, 0.1% SDS, the X-ray film was then exposed to the blot at −70° C. overnight with an intensifying screen. The message RNA for TNF-gamma is abundant in kidney.

Figure 3B:
FIG. 3B is an RNA blot analysis showing that TNF-gamma is expressed predominantly in HUVEC cells (human umbilical vein endothelial cells; lane 9). Lane 6 and lane 8 are non-specific smears. RNA from the cell lines indicated were probed with labeled TNF-gamma-alpha cDNA. Lane 1 is CAMA1 (breast cancer); lane 2 AN3CA (uterine cancer); lane 3, SK.UT.1 (uterine cancer); lane 4, MG63 (osteoblastoma); lane 5, HOS (osteoblastoma); lane 6, MCF7 (breast cancer); lane 7, OVCAR-3 (ovarian cancer); lane 8, CAOV-3 (ovarian cancer); lane 9, HUVEC; lane 10, AOSMIC (smooth muscle); lane 11, foreskin fibroblast.

The same reaction was done to obtain the results shown in FIG. 3B, with the exception that 10 μg poly-A RNA isolated from the indicated tissues was used. In this experiment, the messenger RNA encoding TNF-gamma is expressed predominantly in HUVEC cells (FIG. 3B; lane 9), but not in other cell lines examined; for example; lane 1 is CAMAI (breast cancer); lane 2 is AN3CA (uterine cancer); lane 3 is SK.UT.1 (uterine cancer); lane 4 is MG63 (osteoblastoma); lane 5 is HOS (osteoblastoma); lane 6 is MCF7 (breast cancer); lane 7 is OVCAR-3 (ovarian cancer); lane 8 is CAOV-3 (ovarian cancer); lane 10 is AOSMIC (smooth muscle); and lane 11 is foreskin fibroblast.

Northern blot analyses were also performed to determine the relative expression level of the TNF-gamma RNA with respect to the proliferation state of HUVEC cell cultures. In these experiments, identical amounts of total RNA isolated from HUVEC cells (15 μg) were electrophoretically separated and blotted as described above. RNA was isolated from cultures 1, 2, 3, 4, 6, and 7 days post-seeding. As illustrated in FIG. 4, TNF-gamma RNA (labeled "VEGI") was only seen at low levels in newly seeded cultures (days 1, 2, and 3). However, expression of TNF-gamma RNA was apparent as the HUVEC cells in the cultures began to reach confluence (days 4, 6, and 7). These experiments indicate that TNF-gamma expression increases as cells in a culture or tissue begin to reach the quiescent state of non- or reduced-proliferation.

Example 5

Ability of Recombinant TNF-Gamma to Inhibit WEHI 164, ABAE, and L929 Cell Growth, and to Induce Cell Adhesion in HL-60 Cells.

The adherent target cells were prepared from confluent cultures by trypsinization in PBS, and non-adherent target cells were harvested from stationary cultures and washed once with medium. Target cells were suspended at 3×10$^5$ cells/ml in medium containing 10% FCS. 0.1 ml aliquots were dispensed into 96-well flat-bottomed microtiter plates containing 0.1 ml serially diluted test samples of cells (WEHI 164 and L929). Incubation was continued for 70 hours. TNF-α, TNF-β and bacterially-produced TNF-gamma were added at a 0.5 μg/ml concentration. The cytotoxicity and proliferation activity was quantified using an MTS assay performed by the addition of 20 μl of MTS and phenazine methosulfate (PMS) solution to each well. After a three hour incubation, the OD at 492 nm was measured by an ELISA plate reader. The $OD_{492}$ is proportional to the number of viable cells in the wells. The percent of cytotoxicity was calculated as follows: % cytotoxicity= $(100-OD_{experimental}/OD_{control}) \times 100$. The photographs were taken after 72 hours. As shown by FIGS. 7A and 8, TNF-gamma induced a morphology change which appeared as dark round cells (indicating killed cells).

Figure 9A:
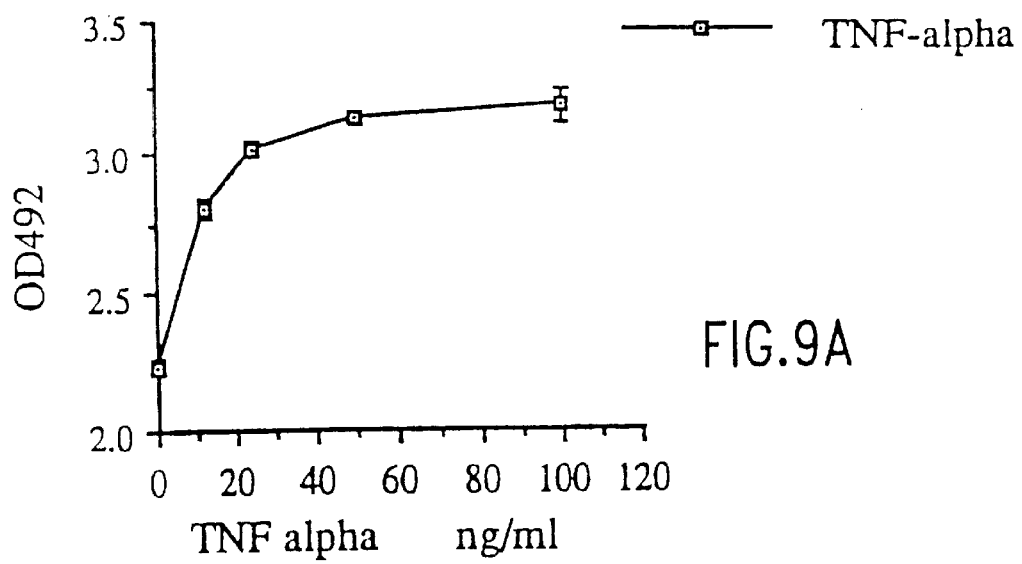
FIG. 9 is a graphical illustration of the effect of TNF-gamma (FIG. 9C), TNF-α (FIG. 9A), and TNF-β (FIG. 9B) on venous endothelial cells. Cell proliferation after venous endothelial cells were treated with commercially available TNF-α and TNF-β and *E. coli* produced TNF-gamma was quantified using an MTS assay.
Figure 9B:
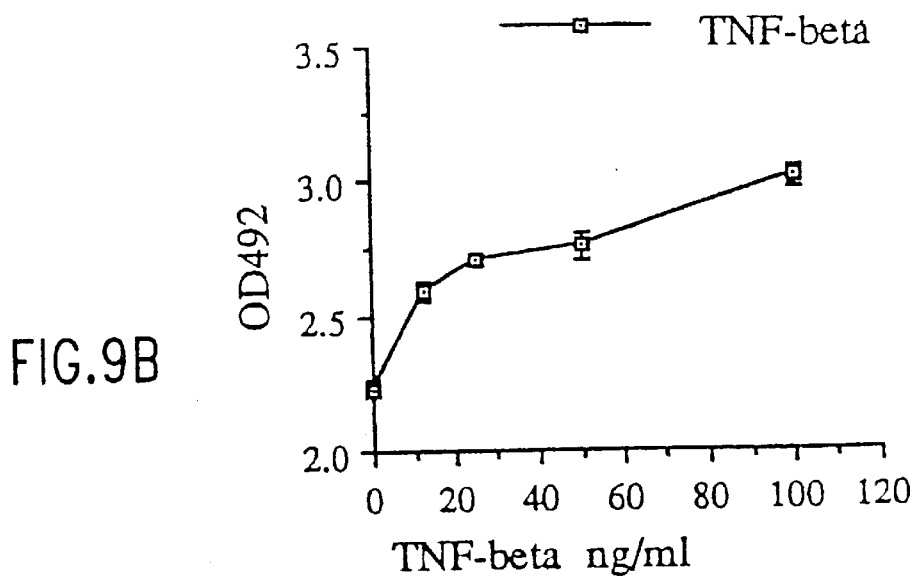
Figure 9C:
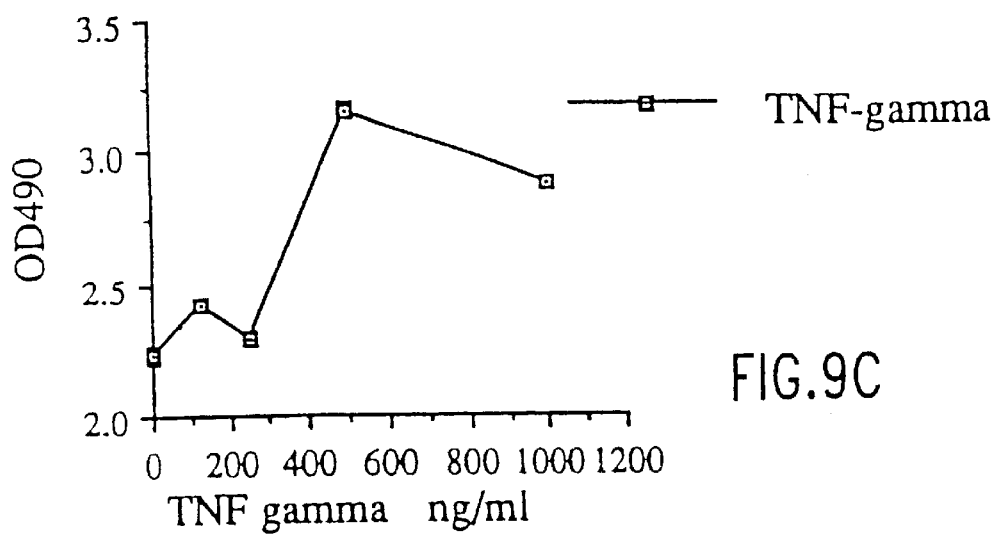

In the graph of FIG. 7B, the assay was performed as described above, however, increasing amounts of TNF-α, TNF-β and TNF-gamma were added to the cultures. The results indicate that TNF-gamma is a dose-dependent inhibitor of the growth of the endothelial cell line WEHI 164, but not of the fibroblast cell line L929 (FIGS. 8 and 9).

A truncated form of the TNF-gamma polypeptide consisting of amino acids 12–147 of the complete TNF-gamma amino acid sequence shown as SEQ ID NO:2 (designated TNF-gamma$_{12-147}$) was also used to examine the effect of TNF-gamma on endothelial cell growth. Treatment of adult bovine aortic endothelial (ABAE) cells with TNF-gamma$_{12-147}$ resulted in nearly complete inhibition of the growth of cells in the ABAE culture, but not of cells in the breast cancer cell lines MDA-MB-435 or MDA-MB-231 (FIG. 10; TNF-gamma is designated "VEGI" in this figure). Nearly complete inhibition of the growth of the endothelial cells was achieved at 10 μg/ml TNF-gamma$_{39-174}$, with a half-maximum inhibitory concentration value ($IC_{50}$) of approximately 1 μg/ml (approximately 70 nM).

Figure 11B:
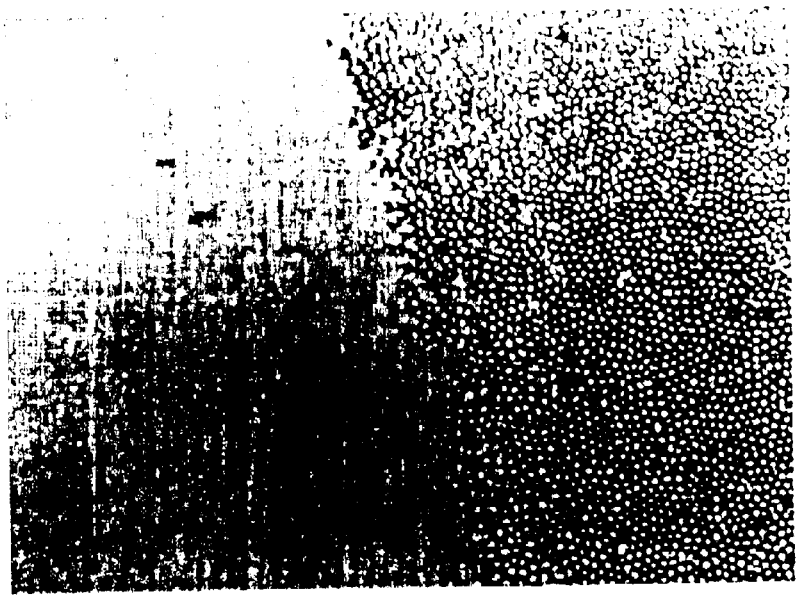
FIG. 11 is a photograph of HL60 cells, with control (FIG. 11A) showing the HL60 cells being spread apart; TNF-α (FIG. 11B) and TNF-gamma (FIG. 11C) induce cell adhesion and cell—cell contact as illustrated by the cells adhering together in the lower right.
Figure 11A:
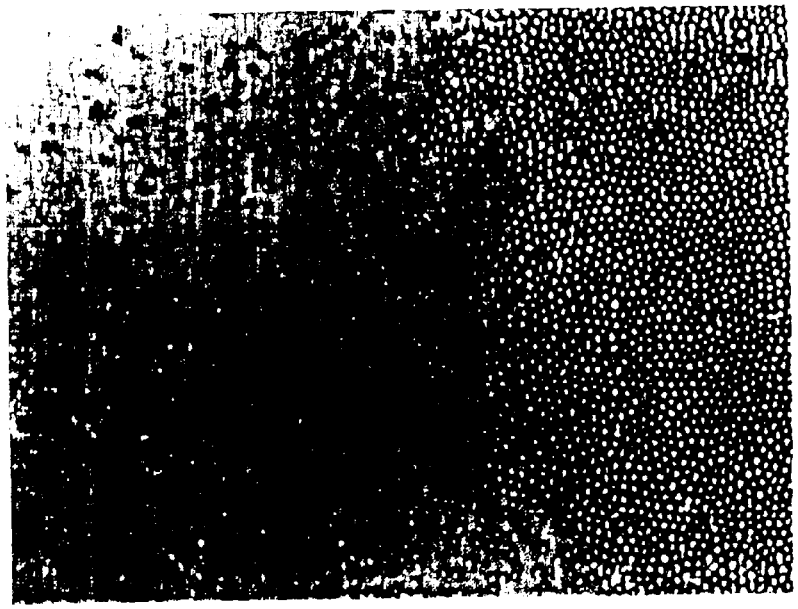
Figure 11C:
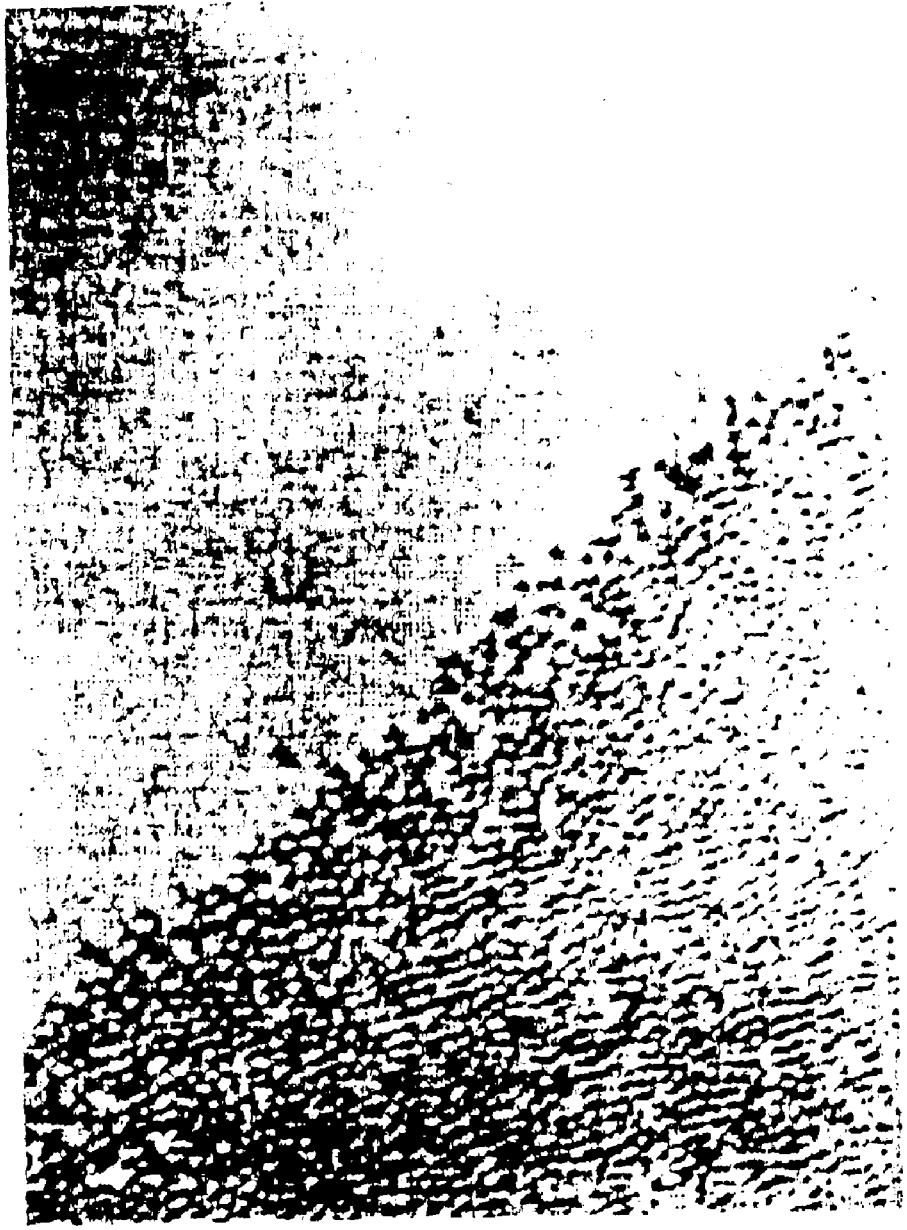

To test adhesion ability of TNF-gamma, HL-60 cells were used and cell adhesion and cell—cell contact were measured by observation under the microscope and scored subjectively by two independent investigators. FIG. 11 illustrates the ability of TNF-gamma to induce cell adhesion. Cultures which were not treated with TNF-gamma contained cells which had spread throughout the culture dish. However, cultures which were treated with TNF-gamma, contained cells which were clearly aggregated together.

Example 6

Measurement of Apoptosis Ability of TNF-Gamma

In a first incubation step, anti-histone antibody was fixed adsorptively on the wall of a microtiter plate module. Subsequently, non-specific binding sites on the wall were saturated by treatment with incubation buffer (e.g., blocking solution). During the second incubation step, the nucleosomes contained in the WEHI 164 cell sample treated with the TNF-α, TNF-β or bacterially-produced TNF-gamma were bound via their histone components to the immobilized anti-histone antibody. In the third incubation step, anti-DNA-peroxidase (POD) reacted with the DNA component of the nucleosomes. After removal of all unbound peroxidase conjugate by a washing step, the amount of peroxidase retained in the immunocomplex was determined spectrophotometrically using the substrate ABTS (2,2'-azino-di-[3-ethylbenzthiazoline sulfonate]). Anti-histone antibody reacted with the histones H1, H2A, H2B, H3, and H4 from the sample. Anti-DNA POD antibody bound to single- and double-stranded DNA. Therefore, the ELISA allowed the detection of mono- and oligonucleosomes and may be applied to measure apoptotic cell death. The level of cell death was measured by the amount of cytoplasmic histone-associated DNA fragments which was indicated by the ratio of the absorbances observed at 405 and 490 nm ($A_{405}/A_{490}$). The results of these experiments are illustrated in FIG. 12 (See Boehringer mannheim Catalogue, 0990 C 932 1541170).

As shown in FIG. 12, WEHI 164 cells were induced to undergo increasingly high levels of apoptosis, resulting in cell death, in the presence of increasing amounts of TNF-gamma. This effect was also observed in the presence of increasing amounts of the control TNF-β or in the presence of any of the analyzed levels of the control TNF-α.

Example 7

Receptor Binding Assay Using TNF-Gamma

Figure 13:
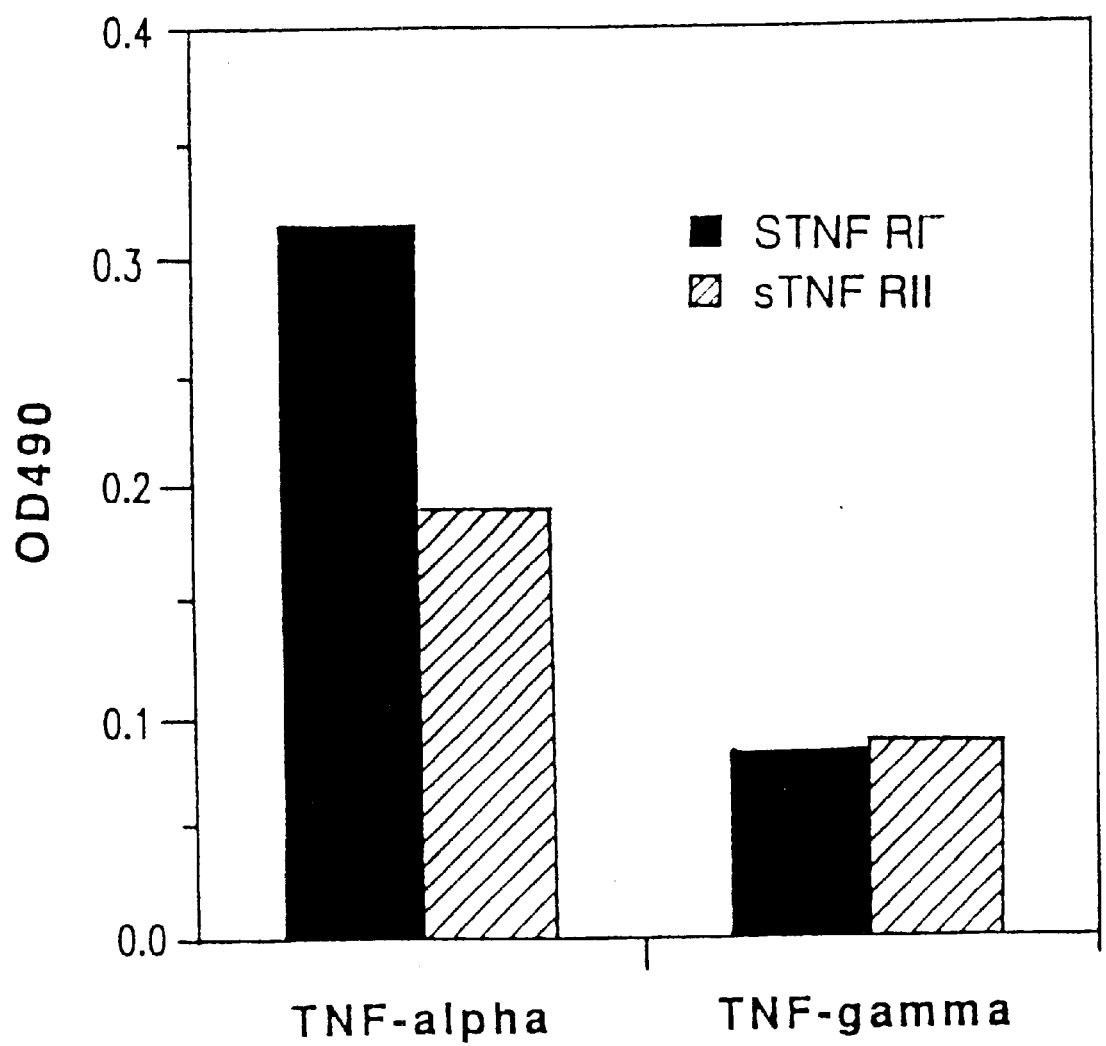
FIG. 13 illustrates that TNF-gamma does not significantly bind to two known soluble TNF receptors, namely sTNF RI (p55; solid bars) and sTNF RII (p75; hatched bars).

TNF-α and bacterially-produced TNF-gamma were purified by Ni-NTA affinity chromatography using the 6-His tag fused to the terminus of the recombinant proteins. 1 μg/well of either protein was added to a nickel chelate-coated 96-well plate (Xenopore Corp.) and incubated for 2 hours. After washing three times, 100 ng of human soluble TNF receptors (specifically, sTNF RI or sTNF RII) was added to each well and incubated for 2 hours. The plate was then washed three times and alkaline phosphatase-labeled polyclonal antibodies raised against either sTNF RI or sTNF RII was added in a total volume of 200 μl. An aliquot of substrate solution (200 μl) was then added to each well and the plate was incubated for an additional 2 hours. The OD was then measured using an ELISA reader (at a test wavelength of 450 nm and a correction wavelength of 590 nm). The results shown in FIG. 13 illustrate that TNF-gamma does not bind significantly to sTNF-receptors when compared to the control binding observed with TNF-α.

Example 8

Expression Via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask. At this time, fresh media is added (e.g., Ham's F12 media, supplemented with 10% FBS, penicillin, and streptomycin). The culture is then incubated at 37° C. for approximately one week. At this time, fresh media is added and subsequently changed every 2–3 days. After an additional two weeks in culture, a monolayer of fibroblasts will have emerged. The monolayer is trypsinized and scaled into larger flasks.

pMV-7 (Kirschmeier, P. T. et al, DNA, 7:219–25 (1988)), which is flanked by the long terminal repeats of the Moloney murine sarcoma virus, is digested with Eco RI and Hind III, and, subsequently, treated with calf intestinal phosphatase. The linear vector is fractionated on agarose gel and purified using glass beads.

The cDNA encoding a polypeptide of the present invention is amplified using PCR primers which correspond to the 5' and 3' end sequences respectively. The 5' primer containing an Eco RI site and the 3' primer includes a Hind III site. Equal quantities of the Moloney murine sarcoma virus linear backbone and the amplified Eco RI and Hind III fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and, subsequently, the media is harvested from a 10 cm plate of confluent producer cells. The spent media, containing the infectious viral particles, is filtered through a millipore filter to remove detached producer cells. This media is then used to infect fibroblast cells. Media is removed from a subconfluent plate of fibroblasts and quickly replaced with the media from the producer cells. This media is removed and replaced with fresh media. If the titer of virus is high, then virtually all fibroblasts will be infected and no selection is required. If the titer is very low, then it may be necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Example 9

In vitro Angiogenesis Assay

This assay was used to determine the relative ability of TNF-gamma$_{12-147}$ to inhibit the FGF-2-induced formation of capillary-like tubular structures in cultures of adult bovine aortic endothelial (ABAE) cells. Three-dimensional collagen gel plates (24-well) were prepared by addition of 0.5 ml chilled solution of 0.7 mg/ml of rat tail type I collagen (Becton Dickinson Labwares, Bedford, Mass.) to each well containing 1×DMEM and adjusting to neutral pH with NaHCO$_3$. After formation of collagen gel (about 1–2 mm thickness), ABAE cells were seeded at 5×10$^4$ cells/well. The cultures were maintained in a humidified 5% CO$_2$ incubator at 37° C. in DMEM containing 10% calf serum (HyClone, Logan, Utah) supplemented with L-glutamine (2 mM) until the cultures reached confluence. The medium was then replaced with fresh medium containing 20 ng/ml of FGF-2. The effect of TNF-gamma$_{12-147}$ as an inhibitor of FGF-2-induced formation of capillary-like tubular structures in ABAE cultures was analyzed by supplementing the culture medium with 0.1, 0.3, 1, 3, or 10 μg/ml of TNF-gamma$_{12-147}$. All cultures were then maintained at 37° C. for an additional 48 hours and then discontinued by fixation with cold methanol (−20° C.).

The abundance of capillary-like structures formed by ABAE cells was analyzed by using a Kotron IBAS Image Analyzer assisted with a Hamamatsu C2400 video camera and a Zeiss Axioshop microscope. The abundance of the capillary-like structures were measured as percentages of the white areas over the total areas measured. As a control, the EC$_{50}$ value for the angiogenic factor FGF-2 to stimulate in vitro angiogenesis was about 5 ng/ml. As a further control, a maximum stimulatory effect was observed at 10 ng/ml of FGF-2.

As shown in FIG. 14 (in which TNF-gamma is designated "VEGI"), observable inhibition of FGF-2-induced tube formation in ABAE cultures was observed by the addition of 1, 3, and 10 μg/ml of TNF-gamma$_{12-147}$ (labeled as VEGI). The IC50 value for the inhibition of FGF-2-induced tube formation was approximately 1 μg/ml, which was similar to that observed for the inhibition of endothelial cell growth (see Example 5).

Example 10

Chicken Embryonic Chorioallantoic Membrane (CAM) Angiogenesis Assay

The CAM assay was carried out essentially as described by Nguyen and colleagues (*Microvasc. Res.* 47:31–40 (1994)) and Iruela-Arispe and Dvorak (*Thromb. Haemost.* 78:672–677 (1997)). The method is based on the growth of new capillary vessels into a collagen gel pellet placed directly on the chorioallantoic membrane (CAM). The angiogenic factors FGF-2 (100 ng) or VEGF (250 ng) were embedded in collagen gel pellets and placed in contact with the CAM. Quantification of angiogenesis in the gels was carried out 24 hours after the placement of the gel pellets by using a Nikon fluorescence microscope. The images were transferred to a Power PC 100 AV, using a CCD Sony camera. Fluorescence intensity was evaluated with NH Image 1.61 software. Fluorescence intensity for the positive controls (which contained an angiogenic factor alone) was considered as the maximum angiogenic response, and set, arbitrarily, at 100. Due to the variability of the assay, inhibition greater than 20% was considered significant.

As an experimental determination of the effect of TNF-gamma on the FGF-2- or VEGF-induced angiogenesis, bacterially-produced TNF-gamma (250 ng) was mixed with either FGF-2 (100 ng) or VEGF (250 ng) and embedded in collagen gel pellets. The pellets were then placed in contact with the CAM as described above. As shown in FIG. 15 (in which TNF-gamma is designated "VEGI"), TNF-gamma markedly inhibited new capillary growth into collagen gels.

Example 11

In vivo Tumorigenicity Assay

An in vivo analysis of the potential effect of TNF-gamma on angiogenesis was performed using a xenograft tumor model. In this experimental approach, one million human breast carcinoma cells (MDA-MB-231 or MDA-MB-435) were injected into the mammary fat pad of female nude mice either alone or mixed with chinese hamster ovary (CHO) cells transfected with TNF-gamma or CHO cells transfected only with the CHO-vector (5×10$^6$ cells per mouse). The TNF-gamma polypeptide expressed in these experiments consisted of the polypeptide shown as SEQ ID NO:2 excluding the N-terminal 22 amino acids. The N-terminal 22 amino acids of this TNF-gamma mutein were replaced by the secretory signal peptide of human interleukin-6 (Hirano, T., et al, *Nature* 324:73–76 (1986)).

Mice which were coinjected with human breast carcinoma cells and either TNF-gamma-expressing CHO cells or vector-transfected CHO cells were then randomized and tumors were measured twice weekly. The tumor size was assessed by measuring perpendicular diameters with a caliper and calculated by multiplying the measurements of diameters in two dimensions. Data are presented in FIGS. 16A and 16B as the mean +/−standard deviation of six mice in each group.

Figure 16A:
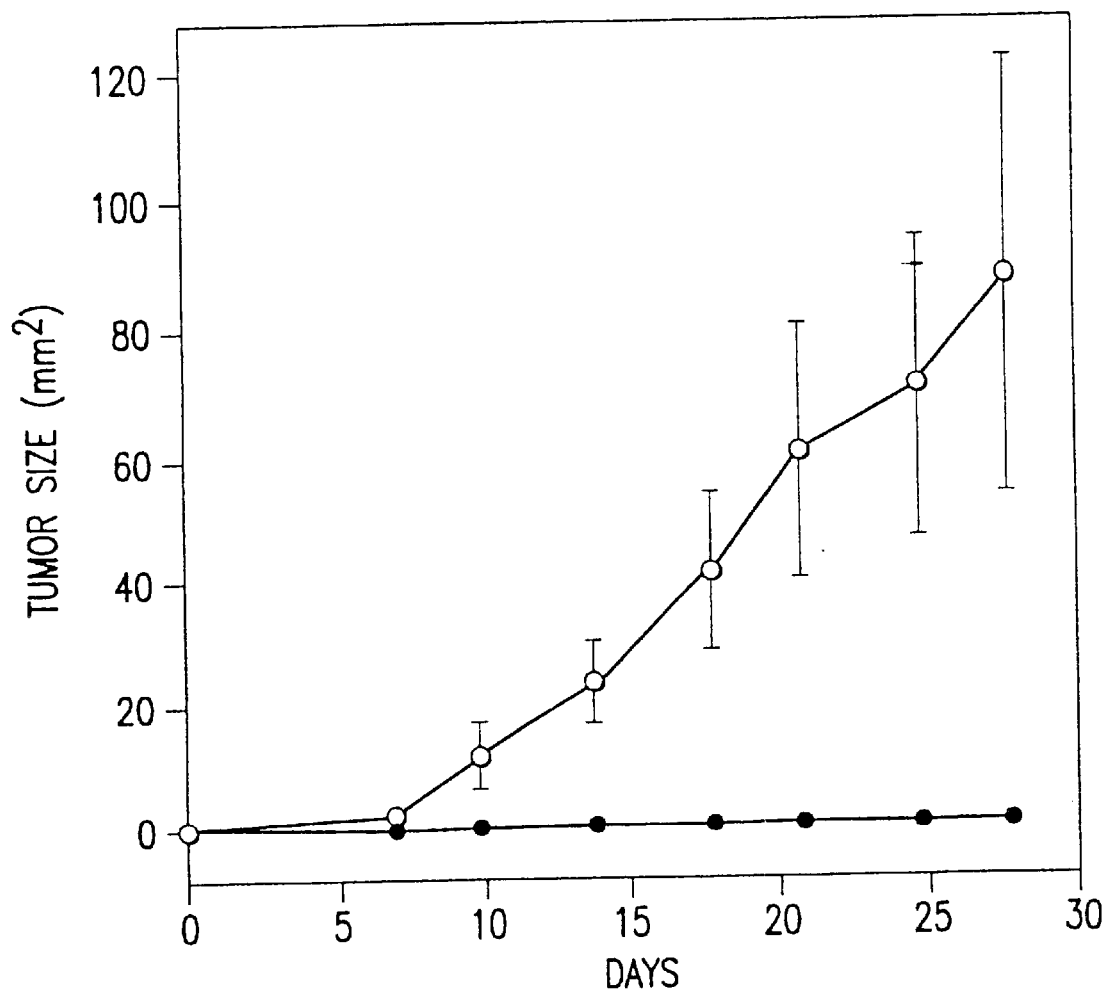
FIG. 16 illustrates the inhibition of growth of human breast cancer xenograft tumors in athymic nude mice by TNF-gamma. Mixtures of TNF-gamma-overexpressing or vector-transfected CHO cells ($5 \times 10^6$ cells per injection) and human breast cancer cells ($1 \times 10^6$ cells per injection) were injected into the mammary fat pads of the nude mice. Tumor sizes (area) were monitored following injection. The sizes of the MDA-MB-231 xenograft tumors ($mm^2$) were plotted as a function of days post-inoculation (FIG. 16A). The sizes of the MDA-MB-435 xenograft tumors ($mm^2$) were plotted as a function of days post-inoculation (FIG. 16B). Open circles represent values of tumors co-inoculated with vector-transfected CHO cells, whereas closed circles represent values of tumors co-inoculated with TNF-gamma-transfected CHO cells.
Figure 16B:
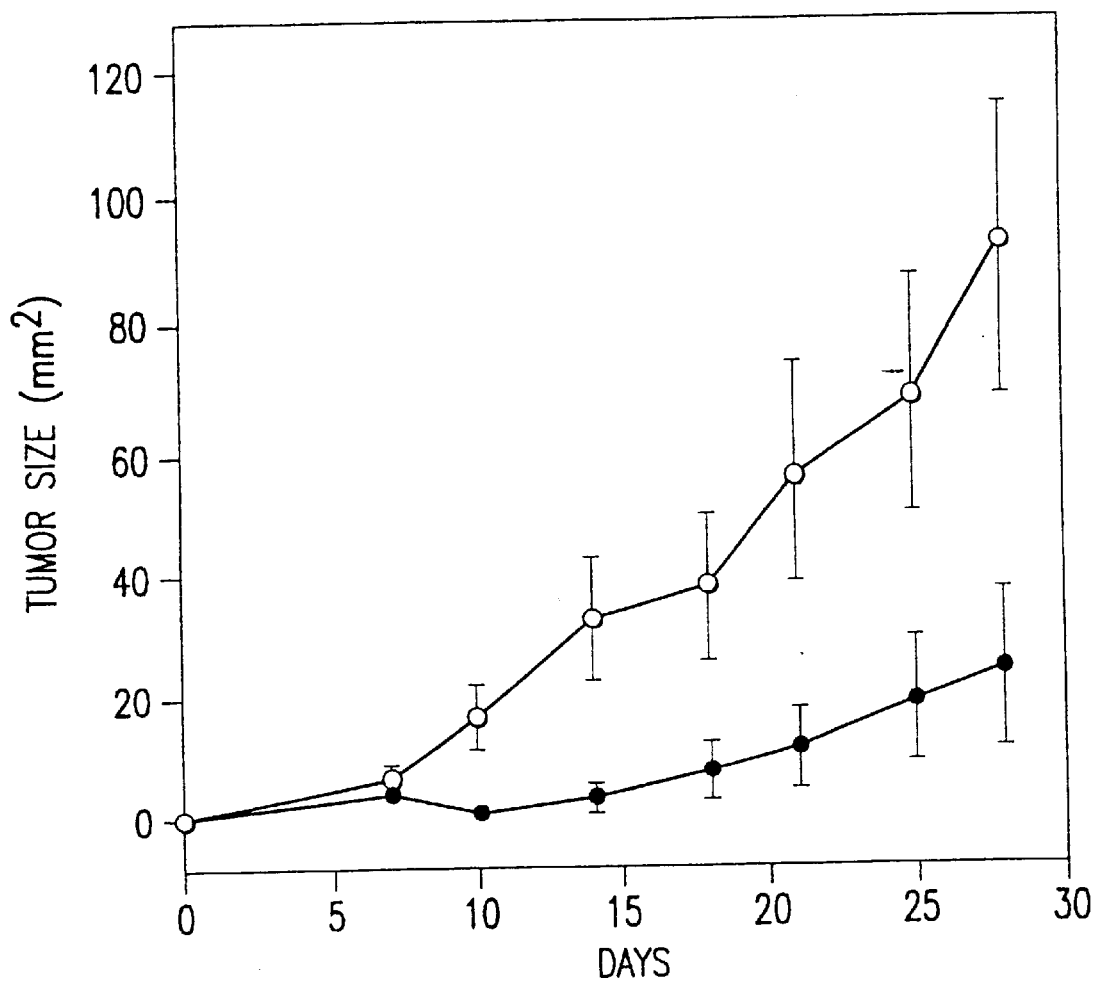

Results presented in FIGS. 16A and 16B (in which TNF-gamma is designated "VEGI") illustrate the sizes of the MDA-MB-231 and MDA-MB-435, respectively, xenograft tumors (mm$^2$) as a function of time (days postinoculation). Tumors were measured beginning on day zero and approximately at 5 day intervals through approximately the twenty-eighth day. In each case, tumors which resulted from breast carcinoma cells coinjected with TNF-gamma-expressing CHO cells (represented by the closed circles in FIGS. 16A and 16B) remained significantly smaller in size than those which resulted from breast carcinoma cells coinjected with vector-only CHO cells (represented by the open circles in FIGS. 16A and 16B).

Example 12

Induction of NF-κB and c-Jun Kinase (JNK) by TNF-Gamma

Activation of cellular NF-κB is preceded by the phosphorylation, ubiquitination, and ultimate degradation of an endogenous NF-κB inhibitor molecule designated IκBa. Degradation of the inhibitor allows the p65 subunit of NF-κB to translocate to the nucleus where it can act as a transcriptional regulator. For this reason, a electrophoretic mobility shift analysis (EMSA) is an appropriate method for analyzing activation of cellular NF-κB by treatment of cultured cells with TNF-gamma.

In these analyses cells (2×10$^6$ per ml) were treated with different concentrations (0.1–1.0 μg/ml) of bacterially-produced TNF-gamma at 37° C. for 12 hours. Nuclear extracts were then prepared from the cultured cells and EMSA was performed as is well-known in the art and essentially as described (Singh, S. and Aggarwal, B. B. *J. Biol. Chem.* 270:10631–10636 (1995)).

Treating U-937 cells with TNF-gamma for 12 hours resulted in increase in DNA-binding by the p65 subunit of NF-κB. Peak activation of DNA-binding by p65 was observed when U-937 cells were treated with 1 μg/ml TNF-gamma for 12 hours. However, treatment of U-937 cells with as little as 0.2 μg/ml TNF-gamma for 12 hours resulted in an observable increase in p65 DNA-binding. TNF-gamma was observed to activate p65 DNA-binding over basal levels from 30 minutes to 18 hours after the initiation of treatment in U-937 cells.

These experiments were elaborated by determining a degradation profile for IκBa in U-937 cells in response to treatment with TNF-gamma. A time course of IκBa degradation was determined by Western blot analysis, a technique that is well-known by one of ordinary skill in the art and has been described by Singh and Aggarwal (*J. Biol. Chem.* 270:24995–25000 (1995)). IκBa was completely degraded when U-937 cells were treated with 0.1–1.0 μg/ml TNF-gamma for 12 hours.

The cellular kinase designated c-Jun kinase (JNK) is an early event in cellular activation. The activation of JNK by TNF-gamma was analyzed as an additional method of determining cellular reaction to treatment with TNF-gamma. The JNK kinase activation assay is well-known by one of skill in the art and has been described by Derijard and colleagues (*Cell* 76:1025–1029 (1994)). After treatment of U-937 cells with 0.1 to 3.0 μg/ml of TNF-gamma for 12 hours, the cells were harvested and assayed for JNK kinase activity. By 6 and 12 hours, JNK activity had increased 2- and 3.6-fold, respectively.

Example 13

Effect of TNF-Gamma in Treating Adjuvant-Induced Arthritis in Rats

An analysis of the use of TNF-gamma to treat rheumatoid arthritis (RA) may be performed through the use of an adjuvant-induced arthritis (AIA) model in rats. AIA is a well-characterized and reproducible animal model of rheumatoid arthritis which is well-known to one of ordinary skill in the art (Pearson, *Ann. Rheum. Dis.* 15:379 (1956); Pearson & Wood, *Arthritis Rheum.* 2:440 (1959)). TNF-gamma is expected to inhibit the increase in angiogensis or the increase in endothelial cell proliferation required to sustain the invading pannus in bone and cartilage observed in this animal model of RA. Lewis and BB rats (available from Charles River Lab, Raleigh, N.C. and the University of Massachusetts Medical Center, Worcester, Mass.) are used as the common and responsive strains for adjuvant-induced arthritis in these experiments.

Initiation of the arthritic condition is induced by the intradermal injection of 0.1 ml adjuvant (5 mg/ml) into the base of the tail. Groups of 5 to 6 rats receive either 0.1 to 1.0 mg/kg TNF-gamma or vehicle intra-articularly 20 days after the injection of adjuvant. At this timepoint, acute inflammation reaches a maximal level and chronic pannus formation will have just begun. The effect of TNF-gamma on pannus formation is analyzed radiologically once each week after day 15 following adjuvant challenge essentially as described by Taurog and colleagues (*J. Exp. Med.* 162:962 (1985)). Briefly, rats are anesthetized with ether or chloral hydrate and positioned so that both hind limbs are X-rayed together. The X-ray films is examined blindly using a scoring system of 0–3 for periosteal reaction, bony erosions, joint space narrowing and destruction. When there is a significant amount of joint damage in vehicle-treated rats, the animals are sacrificed. At this point, the paws are evaluated histologically for the relative degree of tissue damage and for the therapeutic effect TNF-gamma has elicited on these joints.

Finally, TNF-gamma- and vehicle-treated animals undergo a clinical evaluation twice per week to assess hind paw volume using a plethysmometer system and body weight.

Example 14

DR3 Ligand (TNF-Gamma) is a Novel Anti-Tumor Cytokine Existing in Two Different Forms and Differentially Expressed in Different Tissues and Cells Background:

TNF (tumor necrosis factor) superfamily members play very important roles in cell activation, proliferation, differentiation, apoptosis, cytotoxicity and immune regulation. Members of TNF ligand and receptor superfamily are often overexpressed in various human cancer cells and/or activated lymphocytes, their extracellular accessibility makes them excellent potential targets for specific antitumor therapy and immunomodulating therapy. Over the past few years the list of molecules belonging to the TNF receptor and ligand superfamily has grown rapidly. The TNF ligand family of cytokines consist of over 13 type II transmembrane proteins (except TNF-β), the TNF receptor superfamily consist of over 18 type I transmembrane proteins except OPG, also known as OCIF or TR1, which is a secreted protein, and TRID/DcR1/TRIAL-R3, which is a GPI-linked cell surface molecule.

Several TNF receptor superfamily members as well as some of the intracellular signal transducers involved in apoptosis contain a stretch of amino acids, approximately 60 to 80 amino acid long, referred to as the "death domain". These death domain-containing receptors, such as TNFR1, Fas/Apo-1/CD95, DR3 (also known as Wsl, Apo3, TRAMP or LARD), DR4, DR5 or TRAIL-R2, upon activation by their ligands, recruit various proteins that mediate cell death through the death domain. These proteins in turn recruit other proteins via their death domains or death effector domains to transduce the death signal. TNFR1 is expressed in most tissues and cell types and is involved in transducing three major types of signals: activation of the transcription factor NF-κB, c-jun N-terminal protein kinase and apoptosis. Whereas Fas is expressed in lymphocytes, liver, heart, lung, kidney, and ovary. In contrast, DR3 is predominantly expressed in spleen, thymus, and peripheral blood lymphocytes. The ligand for DR3 has not yet been identified. DR3 interacts with TRADD, associates with RIP ordinarily only weakly, but associates strongly when TRADD is overexpressed. In the presence of TRADD, it also associates strongly with FADD. These results suggest that the mechanism of DR3-induced apoptosis is similar to that induced by Fas and TNFR1. Like TNFR1, DR3 also activates NF-κB.

We have identified several novel TNF receptor and ligand superfamily members using several search strategies. One novel TNF-like ligand, TNF-gamma, was predominantly expressed in endothelial cells. Although TNF-gamma shares some of the activities TNF, it does not bind to TNFR1 and TNFR2, indicating that TNF-gamma binds to a distinct receptor. Here we show that TNF-gamma binds to DR3 in several receptor-ligand binding assays. Interestingly, TNF-gamma exists in two different forms which are differentially expresses in different cells and tissues.

Results and Discussion:

We have identified several novel TNF receptor and ligand superfamily members from HGS database which contains over 1.5 million ESTs from over 620 cDNA libraries. One novel TNF-like ligand predominantly expressed in an endothelial cell library exhibited 20–30% sequence homology to other members of the TNF family. The protein was named TNF-gamma-alpha (or VEGIα for Vascular Endothelial derived tumor Growth Inhibitor alpha). Subsequent database analysis and library screening identified a novel splicing variant of TNF-gamma-alpha, designated TNF-gamma-beta (or VEGIβ). This isoform was found predominantly in cDNA libraries of TNFα- and IL-1-induced endotelial cells, monocyte and activated T-cells. The cDNA for TNF-gamma-alpha encodes 174 amino acid residues and TNF-gamma-beta encodes 251 amino acids. Both proteins have characteristics of type II transmembrane proteins. They only differ at the N-terminus which corresponds to the intracellular and transmembrane domains (FIGS. 18A–D and 19).

Recombinant TNF-gamma induces apoptosis in several cell lines such as bovine pulmonary artery endothelial cells and adult bovine aortic endothelial cells. [Bovine pulmonary artery endothelial cells were incubated with various concentrations of TNF-gamma for 48 hours. The apoptosis was assessed by nuclear staining with Hoechst 33342 fluorescence dye (10 mg/ml).] TNF-gamma also induces nuclear factor κB (NF-κB) and c-Jun N-terminal kinase (JNK) activation, inhibits angiogenesis in vitro. [U937 cells were transfected using lipofectamine (following manafacturers instruction) with 0.2 mg of reporter plasmid (NF-κB-SEAP). The transfected U937 cells were collected and added to the 96-well plate (200 ml/well) with various concentrated of TNF-gamma. After Incubation at 37° C. for 72 hr, the NF-κB activity was measured with luminometer at absorbance of 450 nm.]

To identify the novel receptor and ligand pairs, several receptor-ligand binding assays were established. Recombinant soluble TNF-gamma containing the entire ectodomain binds to DR3-Fc fusion protein immobilized on BIAcore chip, purified DR3-Fc also binds to BIAcore chip immobilized with TNF-gamma. [Purified DR3-Fc or TNF-gamma was analyzed on a BIAcore instrument flowcell derivatized with TNF-gamma or DR3-Fc. The shown data represents the net bound (off-rate) region of the plot after binding of TNF-gamma to immobilized DR3-Fc receptor, or binding of DR3-Fc to immobilized TNF-gamma, which is measured in relative mass units (RU) versus time. The binding conditions were performed at high receptor chip densities under diffusion-limited conditions.] Using immunoprecipitation techniques, recombinant TNF-gamma was co-immunoprecipated by DR3-Fc, but not LTbR-Fc immunoadhesins. [The Fc-extracellular domains of DR3 or Fc alone and the corresponding ligands were prepared and binding assays were performed as described elsewhere. The respective Fc-fusions were precipitated with protein G-Sepharose and co-precipitated soluble ligands were detected by immunoblotting with anti-TNF-gamma antibody. Bloting and detection was performed as described in BM Chemiluminescence Western Blotting kit protocol.]

To further demonstrate the interaction between DR3 and TNF-gamma, we screened several cell lines for cell surface expression of TNF-gamma using polyclonal antibody to recombinant soluble TNF-gamma. Consistent with the Northern blot analysis, peripheral blood mononuclear cells (PBMC) and human umbilical vein endothelial cells (HUVEC) express TNF-gamma on the cell surface by immunostaining with antibody to TNF-gamma. [Cells were collected by trypsinization or aspiration, and centrifuged at 1500–2000 rpm for 5 min. The cell pellets were resuspended and washed in 5 ml ice-cold PBS twice. The cells were incubated for 30 min at 40° C. with antibody (10 mg/ml) to TNF-gamma to detected expression of TNF-gamma on cell surface, with DR3-Fc or LTbR-Fc (10 mg/ml) for receptor and ligand binding in the binding buffer (HBSS containing 10% BSA, 20 mM HEPES, pH 7.2, 0.02% NaN3). Purified human IgG (25 mg/ml) was used as control. Cells were then washed and stained with phycoerthrin (PE) conjugated to goat anti-rabbit or anti-human IgG at 20 mg/ml. Fluorescence was analyzed by a FACscan flow cytometer (Becton Dickinson, Mountain View, Calif.).] Two tumor cell lines (MC-38/TNF-gamma and MDA-231/TNF-gamma) transfected with TNF-gamma also express TNF-gamma on the cell surface. FACS analysis showed that here is a shift in the most population following exposure MC-38/TNF-gamma cells to DR3-Fc, indicating cell-surface binding between TNF-gamma and DR3. Similarly, a shift in the MDA-231 cells transfected with TNF-gamma was observed. In addition, DR3-Fc protein also binds to HUVEC cells and PBMC. It is noteworthy that DR3 expression and TNF-gamma binding to PBMC declined after prolonged stimulation with PHA. As predicated, DR3-Fc inhibits the TNF-gamma induced NF-κB activated in a dose-dependent manner. [U937 cells were transfected using lipofectamine (following manafacturer's instructions) with 0.2 mg of reporter plasmid (NF-κB-SEAP). The transfected U937 cells were collected and added to the 96-well plate (200 ml/well) with various concentration of DR3-Fc receptor and 100 ng/ml of TNF-gamma. After incubation at 37° C. for 72 hr, the NF-κB activity was measured with luminometer at absorbance of 450 nm.]

TNF-gamma maps to the chromosomal location within band 9q32. This chromosomal location is close to CD30L (9q33), but is different from the genes for TNFα, LTα and LTβ which are tightly linked within the MHC complex on chromosome 6. Interestingly, the TNF-gamma receptor, DR3, was assigned to the long arm of chromosome 1, region p36.2, is localized to a region where CD30, TNFR2 and OX40 have been mapped.

Consistent with the role of TNF-gamma and DR3 in apoptosis and immune regulation as well as interaction of DR3 with TNF-gamma, local production of TNF-gamma caused complete tumor suppression in vivo in a syngeneic MC-38 murine colon cancer models. In the same animal model, local production of soluble DR3, which may block TNF-gamma function, promotes tumor growth. [The full-length TNF-gamma and extracellular domain of DR3 was cloned into pcDNA3 expression vector and transfected to MCA 38 cells, respectively. After selection and cloning, three clones from each constructs were picked for tumor-genecity study. MCA 38 cells ($1 \times 10^6$ cells/mouse) expressing TNF-gamma or DR3 extracellular domian were injected into C57BL6/6 mice. The tumor size was assessed by measuring perpendicular diameters with a caliper and calculated by multipling the measurements of diameters in two dimensions. Data are represented as the mean +/−SD of 6 mice in each group.] It is clear that most immune cells and cancer cells can express more than one TNF receptor (even more than one death receptor) and ligand superfamily member. The existence of multiple receptors for one ligand or multiple ligands for one receptor, and multiple splicing variant forms of receptor or ligand suggests an unexpected complexity in the regulation of apoptosis and immune function. These receptors and ligands appear to be functionally redundant, but their expression patterns are different, suggesting a distinct tissue or cell specific involvement in a particular function. Moreover, the expression of these ligands and receptors may differ at the level of individual cell types within tissues and the expression level on the same cell type may also differ.

It is estimated that 10% of genes can be alternatively spliced, but in many cases the function of proteins produced remains obscure. To examine the potential functional significance of the two splicing variants of TNF-gamma, PCR analysis was performed in over 100 cDNA libraries. These results are shown in the following table:

Differential expression pattern of DR3, TNF-gamma-alpha, and TNF-gamma-beta

| Library | DR3 | TNF-γα | TNF-γβ |
|---|---|---|---|
| Normal Tissue | | | |
| Liver | + | | + |
| Lymph node | + | | + |
| Tonsil | + | | |
| Bone marrow | + | | |
| Spleen | + | | |
| Heart | + | | |
| Thymus | + | | + |
| Pericardium | + | | |
| Brain | + | | |
| Lung | | | + |
| Skeletal muscle | | | |
| Placenta | | | + |
| Prostate | | | + |
| Pituitary | | | |
| Testis | + | | + |
| Colon | | | |
| Pancreas | + | | |
| Kidney | | | + |
| Kidney cortex | | + | |
| Pualmonary | | | |
| Adipose | + | + | |
| Ovary | + | | + |
| Cerebellum | | | |
| Hippocampus | | | |
| Hyperthalamus | | | |
| Olfactory epithelium | | + | + |
| Striatum depression | | + | |
| Pineal gland | | | |
| Fetal tissue | | | |
| 8 week embryo | + | | + |
| 9 week embryo | + | | |
| Fetal brain | + | + | + |
| Fetal kidney | + | | + |
| Fetal heart | + | + | + |
| Fetal thymus | + | | |
| Fetal lung | + | | + |
| Fetal liver | + | | |
| Fetal spleen | + | | |
| Abnormal tissue and cell | | | |
| Hepatocellular tumor | + | | |
| Hodgkin's lymphoma | + | | |
| Rhabdomyosarcoma | | | + |
| Nasal polyps | | | |
| Spleen, metastic melanoma | | | |
| Spleen, chronic lymphocytic leukemia | | | |
| Healing wound (skin) | + | | + |
| B-cell lymphoma | | | |
| Hemangiopericytoma | | | |
| Pancreas tumor | + | | |
| Burned skin | + | | |
| Prostate cancer, stage C | | | |
| U937 cell | + | | |
| Ovarian tumor | | | + |
| Colon cancer, metasticized to liver | + | | + |
| Colon Cancer | | | |
| Crohn's disease | | | |
| Rejected kidney | + | | + |
| T-cell lymphoma | | | + |
| Ovary tumor | | | |
| Endometrial tumor | | | |
| Skin tumor | | | |
| Pancreatic carcinoma | | + | |
| Jurkat cells | | | + |
| Hela cell line | + | | + |
| LNCAP + 0.3 nM androgen | | | + |
| LNCAP + 30 nM androgen | + | | + |
| Normal cell | | | |
| HUVEC. | + | + | + |
| Dermal endothelial, | | | + |
| Resting T cell | | | |
| Activated T cell (12 hr) | | | |
| Activated T cell (16 hr) | + | | |
| Activated T cell (24 hr) | + | | + |
| T cell helper I | | | |
| T cell helper II | + | | |
| CD34+ | | | + |
| Primary dendritic cells, | + | | |
| Eosinophils | | | |
| Monocytes | + | | + |
| Osteoblasts | | | |
| Keratinocyte | + | | + |
| Stromal endometrial cells | | | |
| Stromal cell TF274 | | | |

As shown in the table, DR3 and two forms of TNF-gamma are differentially expressed in different tissues and cells. In the libraries tested, DR3 was found to be expressed in most tissues, in activated T-cells, monocytes, dendritic cells, TH2 cells, and several other cell lines (such as U937, HeLa) and tumor tissues (such as hepatocellular tumor and Hodgkin's lymphoma). DR3 expression was increased in LNCAP prostate carcinoma cell line treated with 30 nM of synthetic androgen. TNF-gamma-alpha is only expressed in a few tissues or cells such as fetal brain, fetal heart, adipose, kidney cortex, olfactory epithelium, pancreatic carinoma and HUVEC. In contrast, TNF-gamma-beta has a much broader expression pattern. At the cellular level, only endothelial cell, actiavted T-cells, monocytes, keratinocytes, HeLa and Jurkat cells express TNF-gamma-beta. Only HUVEC, fetal brain, and fetal heart cDNA libraries express both forms of TNF-gamma and DR3. TNF-gamma-alpha, TNF-gamma-beta, and DR3 are not expressed in resting T-cells or early stage of activated T-cells (12 hr). DR3 becomes detectable at 16 hr, and both DR3 and TNF-gamma-beta become detectable in T-cells at 24 hr after PHA stimulation. The time-dependent induction of DR3 and then TNF-gamma-beta in activated T-cells suggest that DR3 and TNF-gamma may play an import role in activation induced apoptosis.

Northern blot and cDNA database analysis indicated that DR3 expression is found predominantly in tissues with high content of lymphocytes, TNF-gamma is predominantly expressed in endothelial cells, monocytes and activated T-cells. Thus, DR3 and TNF-gamma may be involved in the activation-induced apoptosis and the negative selection of lymphocytes. The expression pattern of DR3, TNF-gamma-alpha, and TNF-gamma-beta by different cells and tissues. Expression of different splicing variant forms of DR3 or TNF-gamma is likely to set the balance between susceptibility and protection from DR3-mediated apoptosis. It is clear that the pathway leading to apoptosis is highly regulated process and involving a series of proteins.

Another ligand for DR3, named as Apo3L has been described recently, which was also published as Tweak. Unlike TNF-gamma, Apo-3L/Tweak expressed in a wide variety of tissues. The interrelationship and functional importance detween these two DR3 ligands remain to be investigated.

Conclusion:

One pair of novel receptor and ligand of TNF superfamily, DR3 and TNF-gamma, has been identified. Unlike other ligands of TNF family, TNF-gamma exists in two different forms and is differentially expresed in different cells and tissues. It has been suggested that one of the mchanisms for regulating DR3 function is through alternative splicing of DR3. Alternative pre-mRNA splicing generates at least 11 isoforms of DR3, providing a range of functional outcomes that may help shape the immune response. Our data suggested that DR3 function can also be regulated through alternative splicing and differentially expression of its ligand, TNF-gamma. These findings have great impact on how we view the regulation of apoptosis and TNF receptor superfamily function. Identification of two differentially expressed DR3 ligand variants raised the posssibility to selectively modulate apoptosis, immune response and immune surveillance of tumor. Further characterization of physiological and pathological function of two differentially expressed TNF-gamma may provide new insights into the biological activities and physiological function as well as therapeutical aplication of TNF receptor and ligand superfamily. Understanding the role and mechanisms of action of these genes should allow us to develop ways to regulate apoptosis and cell proliferation in a variety of physiological and pathological conditions.

Materials and Methods:

Apoptosis Asassy:

Bovine pulmonary artery endothelia cells (BPAEC) were incubated with various concentrations of TNF-gamma for 48 hours. Apoptosis was assessed morphologically and by nuclear staining with Hoechst 33342 fluorescence dye (10 mg/ml) in triplicate. Live and apoptotic cells were scored in four random fields, about 1,000 cells were counted. The DNA fragmentation was analysed as described previously.

BIAcore Receptor-Ligand Binding Assay

Generation of recombinant receptor DR3-Fc fusion protein and recombinant TNF-gamma were described in previous papers. Purified TNF-gamma or DR3-Fc was immobilized on BIAcore respectively. Purified DR3-Fc or TNF-gamma was analyzed on a BIAcore instrument flowcell derivatized with TNF-gamma or DR3-Fc. The net bound (off-rate) region of the plot after binding of TNF-gamma to immobilized DR3-Fc receptor, or binding of DR3-Fc to immobilized TNF-gamma, was measured in relative mass units (RU) versus time. The binding conditions were performed at high receptor chip densities under diffusion-limited conditions.

Co-Immunoprecipitation and Western Blot Analysis

Polyclonal antisera against TNF-gamma were prepared in rabbits as described previously (Ni, J., et al., *J. Biol. Chem.* 272:10853–10858, (1997)). The Fc-extracellular domains of DR3 or Fc alone and the corresponding ligands were prepared and binding assays were performed as described elsewhere. The respective Fc-fusions were precipitated with protein G-Sepharose and co-precipitated soluble ligands were detected by immunoblotting with anti-TNF-gamma antibody. The samples were loaded into a gel [NOVEX Pre-Cast Gels] (4~20% Tris-Glycine Gel). Bloting and detection was performed as described in BM Chemiluminescence Western Blotting kit protocol.

FACS Analysis

Cells were collected by trypsinization or aspiration, and centrifuged at 1500–2000 rpm for 5 min. The cell pellets were resuspended and washed in 5 ml ice-cold PBS twice. The cells were incubated for 30 min at 40° C. with antibody (10 mg/ml) to TNF-gamma to detected expression of TNF-gamma on cell surface, with DR3-Fc or LTbR-Fc (10 mg/ml) for receptor and ligand binding in the binding buffer (HBSS containing 10% BSA, 20 mM HEPES, pH 7.2. 0.02% NaN3). Purified human IgG (25 mg/ml) was used as a control. Cells were then washed and stained with phycoerythrin (PE) conjugated to goat anti-rabbit or anti-human IgG at 20 mg/ml. Fluorescence was analyzed by a FACscan flow cytometer (Becton Dickinson, Mountain View, Calif.).

NF-κB-SEAP (Secreted Alkaline Phosphatase) Reporter Assay

U937 cells were transfected using lipofectamine (following manufacturer's instructions) with 0.2 mg of reporter plasmid (NF-κB-SEAP). The transfected U937 cells were collected and added to the 96-well plate (200 ml/well) with various concentration of active TNF-gamma or inactivated (boiled) TNF-gamma or in combination with various concentration DR3-Fc receptor and 100 ng/ml of TNF-gamma. After Incubation at 37° C. for 72 hr, the NF-κB activity was measured with luminometer at absorbance of 450 nm.

Tissue and Cell Distribution Analysis Using PCR on a Large Collection of cDNA Libraries and cDNA Database.

To study the tissue distribution of DR3, TNF-gamma-alpha and TNF-gamma-beta, two gene specific primers were synthesized for each gene. Over 100 cDNA libraries are tested and the libraries gave a positive predicted size signal are indicated as+.

In Vivo Tumorigenecity Assay.

The full length TNF-gamma and extracellular domain of DR3 was cloned into pcDNA3 expression vector (Invitrogen, Carlsbad, Calif.) and transfected to MCA 38 cells, respectively. Subsequent to transfection, G418 selection, and cloning, three clones from each constructs were picked for tumorgenecity study. The expression of TNF-gamma and DR3 in MCA 38 cells were confirmed by Northern analysis. MCA 38 cells ($1 \times 10^6$ cells/mouse) expressing TNF-gamma or DR3 extracellular domian were injected into C57BL6/6 mice. Mice then were randomiced and tumors were measured twice weekly. The tumor size was assessed by measuring perpendicular diameters with a caliper and calculated by multipling the measurements of diameters in two dimensions. Data are represented as the mean +/−SD of 6 mice in each group.

Example 15

TNF-Gamma-Alpha, a Novel Member of TNF Cytokine Family, Causes Endothelial Cell Apoptosis Background:

TNF-gamma-alpha is a novel protein with a molecular weight of 22 kD that was recently identified by searching the Hunan Genome Sciences (HGS) cDNA database (Tan, K. B., et al, *Gene* 204:35–46 (1997)). TNF-gamma-alpha is a type II membrane protein and exhibits about 30% sequence homology to human tumor necrosis factor α (TNFα). This newly identified member of the TNF family has been demonstrated to be abundantly expressed in endothelial cells as well as in kidney, lung and prostate. TNF-gamma-alpha expression in HL-60 and THP1 cells was induced by PMA treatment. Radiation hybrid mapping localized TNF-gamma gene on chromosome 9q32, near CD30L. Because of its overexpression in endothelial cells, TNF-gamma-alpha has been suggested to possibly play a role in vascular functions (Tan, K. B., et al, *Gene* 204:35–46). The present study was undertaken to explore whether TNF-gamma-alpha induces endothelial cell apoptosis, a phenomenon suggested to be one cause of endothelial cell damage contributing to various inflammatory disorders and cardiovascular dysfunction (Bryant, D., et al, *Circulation* 97:1375–1381 (1998)). To examine this possibility, we used bovine pulmonary artery endothelial cells (BPAEC) to which TNFα-induced apoptosis has been demonstrated (Polunovsky, V. A., et al., *Exp. Cell Res.* 214:584–594 (1994)). Apoptosis was detected on the basis of morphological (including ultrastrutual) and biochemical characteristics (DNA fragmentation). In addition, we studied the effects of TNF-gamma-alpha on the activity of stress kinases, stress-activated protein kinase (SAPK/JNK) and p38 mitogen-activated protein kinase (p38 MAPK), and the caspases. Both signaling pathways are believed to be implicated in programmed cell death (Xia, Z., et al., *Science* 270:1326–1331 (1995)). The expression of Fas and Bcl-2 in TNF-gamma-alpha-stimulated BPAEC was also determined in view of the death-promoting effect of Fas and the anti-apoptotic effect of Bcl-2 (Nagata, S. and Golstein, P. *Science* 267:1449–1456 (1995)).

Materials and Methods:

Materials.

TNF-gamma-alpha protein (22 kD) was provided by HGS. Ac-YVAD-AMC and Ac-DEVD-AMC were purchased from American Peptide (Sunnyvale, Calif., USA). ZVAD-fmk and Ac-YVAD-CHO were obtained from Enzyme Systems (Dublin, Calif., USA) and Peptides International (Louisville, Ky., USA), respectively. Ac-DQMD-AMC, Ac-LEED-AMC, Ac-VETD-AMC and anti-p38 MAPK mAb were provided by SmithKline Beecham (SB) Pharmaceuticals (King of Prussia, Pa., USA). Ac-IETD-AMC and mouse-anti-human JNK mAb were purchased from Biomol Research Laboratories (Plymouth Meeting, Pa., USA) and PharMingen (San Diego, Calif., USA), respectively. Mouse soluble TNF receptor 1(sTNFR1) and TNF receptor 2 (sTNFR2) was obtained from R&D Systems (Minneapolis, Minn., USA).

Cell Cultures.

BPAEC were obtained from the American Type Culture Collection (Rockville, Md., USA). The cells were grown in DMEM supplemented with 10% heat-inactivated FCS in a humidified environment of 5% $CO_2$/85% air at 37° C. as previously described (Yue, T. L., et al., *Mol. Pharmacol.* 51:951–962 (1997)). Cells at a subconfluent density were used. Before experiments, the medium was changed to DMEM contained 2% FCS. BPAEC from passages 17–20 were used in all studies.

Morphological Assessment and Quantification of Apoptosis.

To quantify cells undergoing apoptosis, cell monolayers were fixed and stained with Hoechst 33324 (Molecular probe, Eugene, Oreg., USA) as described previously (Yue, T. L., et al., *Mol. Pharmacol.* 51:951–962 (1997)). The morphological features of apoptosis (cell shrinkage, chromatin condensation, blebbing, and fragmentation) were monitored by fluorescence microscopy. Transmission electron microscopy study was done as reported previously (Yue, T. L., et al., *Mol. Pharmacol.* 51:951–962 (1997)).

DNA Fragmentation Analysis.

(a) DNA Ladder: Cells treated with vehicle or TNF-gamma-alpha were lysed in lysis buffer containing 100 mM NaCl, 10 mM Tris-HC1, pH 8.0, 2.5 mM EEDTA, 0.5% SDS, and 100 μg/ml protein kinase K. The lysates were incubated at 55° C. for 16 h. After incubation, the lysates were gently extracted three times with pheno/chloroform/soamyl alcohol, precipitated in ethanol, treated with DNAse-free RNAse, re-extracted, and precipitated again as described previously. DNA electrophoresis was carried out in 1.8% agarose gels containing ethidium bromide, and DNA fragmentations were visualized under ultraviolet light.

(b) In situ end-labeling (TUNEL):

BPAEC were cultured in two-chamber slides (Nunc) and treated with TNF-gamma-alpha for 8 to 24 h. In situ detection of apoptotic cells was performed by using terminal deoxyribonucleotide transferase-mediated dUTP nick end labeling with an ApopTag in situ apoptosis detection kit (Oncor) following the manufacturer's recommendation.

Stress-Activated Protein Kinase (SAJPK/JNK) Assay.

SAPK activity was measured using GST-c-Jun$_{(1-81)}$ as bound to glutathione-Sepharose 4B as described previously (Yuc, T. L., et al., *Mol. Pharmacol.* 51:951–962 (1997)). Briefly, the cells were treated with vehicle or TNF-gamma-alpha, washed, and lysed in lysis buffer. The nuclear-free supernatant was normalized for protein content and immuno-precipitated with anti-SAPK antibody-conjugated Sepharose beads. The mixture was rotated 4° C. for 3 h. The phosphorylation buffer containing GST-c-Jun$_{(1-81)}$, 10 μC[γ-$^{32}$ Pl-ATP, 125 μM ATP and 100 mM MgCl, was added to the SAPK-bound beads in assay buffer. The reaction was terminated after 20 min at 30° C. by addition of protein loading buffer and heated at 90° C. for 3 min. Phosphorylated proteins were resolved in 10% SDA-polyacrylamide gel electrophoresis followed by autoradiography. The intensity of the bands was quantified by PhosphorImager (Yuc, T. L., et al., *J. Mol. Cell. Cardiol.* 30:495–507 (1998)).

p38 MAPK Assay.

The cell lysates prepared as above were immuno-precipitated wit anti-p38 MAKP antibody bound to protein A agarose for 4 h at 4° C. The beads were washed with lysis buffer and then with kinase buffer as described previously (Kumar, S. M., et al., *J. Biol. Chem.* 271:30864–30869 (1996)). The immune-complex kinase assay was initiated by the addition of 25 µl of kinase buffer containing 2 µg of GST-ATF2 and 50 µM [γ-$^{32}$P] ATP (20 Ci/mmol). The phosphorylated products were resolved by SDA-PAGE and visualized by Phosphorimage.

In vitro Transfection of Dominant-Interfering Mutant of c-JUN in BPAEC.

The cells were plated in two-chamber slides. The cells were cotransfected with 0.5 µg/ml of Pegfp-c-1 (Clontech; Li, Y. and Horwitz, M. S. *Biotechnology* 23:1026–1028) as a fluorescent marker of transfected cells together with 1 µg/ml of either the empty cloning vector pCDNA1 (control) or the dominant-interfering c-Jun mutant pcDNA1-FigΔ169 (Xia, Z., et al., *Science* 270:1326–1331 (1995)) using Calphos Maximizer Transfection Kit (Clontech) according to the manufacturer's recommendation. Following transfection, the cells were allowed to recover in complete medium for 24 h. The cells were treated with TNF-gamma-alpha and the number of apoptotic cells was assessed by nuclear staining after fixation as described in Methods.

Caspase Activity Assay.

The cells were treated with vehicle of TNF-gamma-alpha. Caspase activity assays were performed as reported previously (Yuc, T. L., et al., supra). Briefly, cells were harvested and suspended in buffer containing 25 mM HEPES, pH 7.5, 10% sucrose, 0.1% CHAPS, 2 mM DDT, 5 mM PMSF, and 1 µM pepstatin A. The suspension was forced through a 25 gauge needle 10 times to break cells the homogenate was centrifuged at 100,000×g for 1 h, and the cleared lysates were used for enzyme assays. Cell extracts (5–20 µg protein) were diluted into the assay buffer (Table 1) and preincubated for 10 min at 30° C. prior to the addition of the substrates. Levels of released 7-amino-4-methylcocmarin (AMC) were measured with a Cytofluor-4000 fluorescent plate reader (Perseptive Biosystems) at an excitation and emission wavelengths of 360 nm and 460 nm, respectively.

Immunohistochemical Analysis for Fas, Bcl-2 and Caspase-3 Expression.

The cells were cultured in two-chamber slides. After treatment with vehicle or TNF-gamma-alpha, the cells were fixed with 4% paraformaldehyde for 30 min at 4° C. and then changed to cold PBS. The cells were treated with 0.2% Triton X-100 for 40 min at 4° C., washed with cold PBS and then non-specific immunoglobulin binding sites were blocked with normal goat serum (Vector Laboratories) for 1 h at room temperature. The cell samples were incubated with the primary antibody mouse anti-human Fas (Upstate Biotechnology), mouse anti-human Bcl-2 (DAKO) or rabbit anti-human CPP32 p17 peptide polyclonal antisera (SmithKline Beecham), for 1 h at room temperature. As a negative control, the cell samples were incubated with nonimmune IgG (for Bcl-2 and CPP32) or IgM (for Fas) instead of the primary antibody. After incubation with the primary antibody, cells were washed with PBS and then incubated for 30 min with a secondary antibody conjugated to fluorescein isothiocyanatc. Cells were washed, treated with Veetashield mounting medium (Vector Laboratories) and viewed by fluorescence microscopy (Olympus IX70).

Statistical Analysis.

All values are represented as mean±S.E.M. of n independent experiments. Statistical evaluation was performed by using one-way analysis of variance. Differences with a value of p<0.05 were considered significant.

Results:

TNF-Gamma-Alpha Induces Apoptosis in BPAEC.

When BPAEC were exposed to TNF-gamma-alpha the cells shrunk and retracted from their neighboring cells, and the cytoplasma became condensed. Cells stained with Hoechst 33324 and assessed by fluorescence microscopy demonstrated condensed chromatin of fragmented nuclei and blebbing of the plasma membrane. The study with transmission electron microscopy showed that TNF-gamma-alpha-treated BPAEC contained many cells undergoing morphologic alterations characteristic of apoptosis including condensation of chromatin and appearance of apoptotic bodies. The characteristic degradation of DNA into oligonucleosomal-length fragmentation was observed when the cells were exposed to TNF-gamma-alpha (30–300 ng/ml) for 24 h. The DNA fragments in situ was further visualized by using TUNEL method. A considerable fraction of endothelial cells treated with TNF-gamma-alpha showed positive staining; no positively stained cells were found in the vehicle-treated cultures.

TNF-gamma-alpha-induced endothelial cell apoptosis was a time- and concentration-dependent process with an $EC_{30}$ value of 72 ng/ml. A significant increase in the number of cells with apoptotic morphological changes was apparent 6–8 h after exposure of the cells to TNF-gamma-alpha. Under similar conditions, TNF-α at 10 ng/ml induced apoptosis in PEAPC by 16.7±3.2% (n=4).

Effects of sTNFR1 and sTNFR2 on TNF-Gamma-Alpha-Induced Apoptosis in BPAEC.

Neither sTNFR1 nor sTNFR2 showed effect on TNF-gamma-alpha-induced apoptosis in BPAEC. Under the same condition TNFα-induced apoptosis in BPAHC was reduced by sTNFR1 significantly.

Regulation of Fas and Bcl-2 Expression in Endothelial Cells by TNF-gamma-alpha. Immunocytochemical analysis of Fas and Bcl-2 proteins was determined at 8 and 24 h after treatment with TNF-gamma-alpha. The basal level of Fas in BPAEC was undetectable. However, a significant number of cells expressing Fas receptor were detected at 8 and 24 h after stimulation. When mouse IgM was substituted for the primary antibody, positive Fas immunoreactivity was not detected. In contrast, Bcl-2 expression was not detected in neither unstimulated nor TNF-gamma-alpha-treated BPAEC.

Activation of SAPK/JNK and p-38 MAPK

With regard to the effects of TNF-gamma-alpha on SAPK/JNK activity in BPAEC, exposure of endothelial cells to TNF-gamma-alpha induced a rapid activation of SAPK/JNK. A significant increase in SAPK/JNK activity was detected 20 min after stimulation, peaked at 40 min. and then returned to the basal levels after 60 min. TNF-gamma-alpha-induced activation of SAPK/JNK in endothelial cells is a concentration-dependent process. Some basal activities of SAPK/JNK activity was increased by 5.6±1.4 folds (p<0.05 n=4) and 9.1±1.8 folds (p<0.0 n=6) over the basal level in the presence of 50 and 300 ng/ml of TNF-gamma-alpha, respectively. TNF-gamma-alpha activated p38 MAPK in BPAEC with a similar time course as SAPK/JNK but to a lesser extent. The peak of p38 MAKP activity was increased by 3.1±0.5 and 3.8±0.4 folds over the basal level in the presence of 100 and 300 ng/ml of TNF-gamma-alpha, respectively.

Effects on TNF-Gamma-Alpha-Induced Apoptosis by Expression of Dominant-Interfering Mutant of c-JUN in BPAEC or by the p38 MAPK Inhibitor, SB203580.

To investigate the role of SAPK/JNK in TNF-gamma-alpha-induced apoptosis in BPAEC, we transfected BPAEC with a dominant-interfering mutant of c-JUN, pCDNA1-FlagΔ169, in which a deletion in the NH2-terminal transactivation domain that includes the binding site for JNK (Xia, Z., et al., supra). Expression of dominant-interfering c-JUN construct in BPAEC reduced TNF-gamma-alpha-induced apoptosis by 62.8% (p<0.05). TNF-gamma-alpha-induced apoptosis in BPAEC was also attenuated by a specific p38 MAPK inhibitor, SB203580, in a concentration dependent manner. In the presence of 3 and 10 $\mu$M of SB203580, TNF-gamma-alpha-induced BPAEC apoptosis was reduced by 33% (p<0.05) and 51% (p<0.01), respectively. No further inhibition was observed when the concentration of SB203580 was increased.

Activation of Caspases in BPAEC by TNF-Gamma-Alpha.

TNF-gamma-alpha-induced BPAEC apoptosis was attenuated by ZVAD-fmk, an irreversible cell-permeable inhibitor of caspase (Jocobson, N. L., et al., *Cell Biol.* 133:1041–1051 (1996)), added to the culture medium 1 h prior to TNF-gamma-alpha treatment. Under the same conditions, the addition of Ac-YYAD-CHO, a relatively specific inhibitor of caspase-1 (Thorberry, N. A., et al., *Nature (Lond)* 356:768–774 (1992)), up to 100 $\mu$M showed no effect in enhancing BPAEC rescue. To further determine which of the caspase family members are activated in the TNF-gamma-alpha-induced apoptotic process in the endothelial cells, we examined cell extracts for protcolytic activity. The relative rates of AMC formation were measured with a series of defined peptide sequence variants that are relatively specific for caspase 1, 3, 4, 7, or 8 under the optimal conditions as described previously (Yuc, T. L., et al., supra). Similar results were observed from three repeated experiments. Cell extracts from TNF-gamma-alpha-treated BPAEC were highly active on Ac-DEVD-AMC and to a lesser extent on Ac-DQMD-AMC, but not active on the remaining three substrates which are more specific for caspase 1, 4, and 8. The proteolytic activity appeared at 6 h after the cells were treated with TNF-gamma-alpha, peaked at 24 h, and gradually returned to basal levels within 48 h. The relative velocities of four substrate hydrolysis rates by the TNF-gamma-alpha-treated cell extracts and recombinant caspase-3 were compared. The relative velocities of the two enzyme sources of four substrates were very similar.

To further confirm that caspase-3 is activated by TNF-gamma-alpha in BPAEC, immunocytochemical detection of its enzymatically active form, the 17-kD subunit, was performed. The antibody was raised against a peptide from the C-terminal portion of the p17 subunit. The neoepitope antibody only binds caspase-3 if there has been specific cleavage between the "p-10" and "p-20" subunits. Using this neoepitope antibody, only processed caspase-3 is detected, but not the porenzyme (Yuc, T. L., et al., supra). The 17 kD subunit of caspase-3 was detected in TNF-gamma-alpha-treated but not vehicle-treated BPAEC, and was localized with fragmented nuclei within the cells.

Discussion:

The studies presented in this paper demonstrate that TNF-gamma-alpha, a novel TNF-like cytokine and a type II transmembrane protein, induces intensive apoptosis in cultured endothelial cells as reflected by morphological and biochemical criteria. Under our experimental conditions, spontaneous BPAEC death was approximately 2–4% which is in accord with a previous observation (Polunovsky, V. A., et al., supra). The effect of TNF-gamma-alpha was concentration-dependent with an $EC_{80}$ value of 72 ng/ml (3.5 nM) and a significant number of apoptotic cells was detected 6–8 h after treatment. Moreover, the expression of pro-apoptotic gene, Fas, was demonstrated in TNF-gamma-alpha-treated BPAEC, which is consistent with that observed in apoptotic endothelial cells reported previously (Yuc, T. L., et al., supra).

The receptor(s) mediating TNF-gamma-alpha activity has not been identified as yet. To examine whether TNF-gamma-alpha acts via distinct receptor(s), we tested the effects of sTNFR1 and sTNFR2 on TNF-gamma-alpha-induced apoptosis in BPAEC. These two TNFRs have been shown previously to block the cell surface TNFR1 and TNFR2 mediated TNF bioactivities on responsive cell lines (data from R&D Systems). Neither sTNFR1 nor sTNFR2 inhibited the effect of TNF-gamma-alpha on BPAEC. In contrast, TNF$\alpha$-induced apoptosis in BPAEC was significantly reduced by sTNF1. The results suggest clearly that TNF-gamma-alpha-induced cell death is independent of sTNFR1 or TNFR2.

Recent research efforts on TNF family members have demonstrated that TNF$\alpha$ and Fas activate stress protein kinases, SAPK/JNK and p38 MAPK, in a variety of cell types (Sluss, H. K., et al., *Cell Biol.* 14:8376–8384 (1994)), however, the effects of other members of this family on SAPK and p38 MAPK are not well studies. Moreover, controversies regarding the role of SAPK/JNK and p38 MAPK in TNF$\alpha$ or Fas-mediated cell death have been reported. For example, TNF$\alpha$-induced apoptosis is dependent on JNK activity in U937 cells (Verjeij, M., et al., *Nature (Lond)* 380:75–79 (1995); Zanke, B. W., et a., *Curr. Biol.* 6:606–613 (1996)) but not in fibroblasts (Reinhard, C., et al., *EMBO J.* 16:1080–1092 (1997)) indicating that the consequences of JNK activation vary considerably among cell types. Fas-mediated JNK activation occurs with a different kinetics from that of TNF$\alpha$, suggesting that TNF$\alpha$ and Fas most likely activate JNK through a different mechanism (Wilson, D. J., et al., *Eur. J. Immunol.* 26:989–994 (1996)). Moreover, Juo, et al., reported recently that blockade of p38 MAPK by a specific p38 MAPK inhibitor did not affect Fas-mediated apoptosis in Jurkat cells (Juo, P., et al, *Mol. Cell Biol.* 17:24–35 (1997)). Therefore, we were interested in finding whether TNF-gamma-alpha activates JNK and p38 MAPK, and what is the role of this activation in TNF-gamma-alpha-mediated apoptosis in BPAEC. The present investigation clearly demonstrates that both JNK and p38 MAPK were rapidly activated by TNF-gamma-alpha in a similar fashion as observed in TNF$\alpha$-activated U937. Moreover, expression of dominant-interfering mutant of c-JUN in BPAEC reduced TNF-gamma-alpha-induced cell death indicating that TNF-gamma-alpha-induced apoptosis in BPAEC was dependent on JNK activity. To address the potential involvement of p38 MAPK in TNF-gamma-alpha-mediated apoptosis in BPAEC, a specific p38 MAPK inhibitor SB203580 was tested. This inhibitor has been shown to specifically inhibit p38 MAPK activity in vitro with no effect on a variety of kinases tested, including JNK and ERK-1 (Cuenda, A., et al., *FEBS Lett.* 364:229–233 (1995)). TNF-gamma-alpha-induced apoptosis in BPAEC was also reduced by SB203580 in a concentration-dependent manner, indicating that p38 MAPK signaling pathway is involved in TNF-gamma-alpha-mediated BPAEC apoptosis. This effect is different from that observed in Fas-mediated apoptosis in Jurkat cells in which SB203580 had no protective effect (Juo, P., et al., supra). Moreover, TNF-gamma-alpha-induced p38 MAPK activation occurs with must faster kinetics in BPAEC than that observed in Jurkat cells in which the peak of p38 MAPK activation was at 2–4 h after stimulation by Fas, indicating TNF-gamma-alpha and Fas most likely activate p38 MAPK through a different mechanism with a different outcome. Our data further suggests that different members of TNF family may have different signaling pathways to mediate cell death or have different effects in different cell types.

Recent work has supported a central role for the caspase family members, as effectors of apoptosis (Kumar, S. M., et al., supra). However, the role of caspases in endothelial cell apoptosis has not been sufficiently explored. Two characteristic features of the caspase family have been elucidated; they cleave their target proteins after specific aspartic acids, resulting in two subunits that together form the active site of the enzyme (Nicholson, D. W., et al., *Nature (Lond)* 376:37–43 (1995); Kumar, S. M., et al., supra). Among the caspase family, caspase-3 (CPP32) has been considered as a central component of the proteolytic cascade during apoptosis and plays a key role in this family (Wang, X., *EMBO J.* 15:1012–1020 (1996); Woo, M., et al., *Gene Development* 12:806–819 (1998)). TNF-gamma-alpha-induced BPAEC apoptosis was inhibited by ZVAD-fmk, indicating a potential role for the caspase family in this effector pathway for apoptosis. To determine which of the caspase family members are involved, we examined the substrate specificity of proteolytic activity in the extracts from TNF-gamma-alpha-activated BPAEC by measuring the relative rate of AMC formation from 6 different substrates which are relatively specific for caspases 1, 3, 4, 7 and 8 (Talanian, R. V., et al., *J. Biol. Chem.* 272:9677–9682 (1997)). Treatment of BPAEC with TNF-gamma-alpha resulted in a significant increase in protcolytic activity towards DEVD-AMC mainly and DQMD-AMC to some extent, both of which show the relative specificity for caspase-3 (Kumar, S. M., et al., supra). There was no induction in protcolytic activity in TNF-gamma-alpha-activated cell extracts when Ac-YVAD-AMC, LEED-AMC or VETD-AMC were used as the substrate, indicating that caspases 1, 4 and 8 might not be involved. Moreover, comparison of the substrate specificity of the extracts from TNF-gamma-alpha-treated BPAEC with recombinant caspase-3 showed a similar pattern, further suggesting that caspase-3 may be the predominant member in the caspase family activated by TNF-gamma-alpha. Furthermore, immunocytochemical studies detected the active form of caspase-3 in TNF-gamma-alpha treated BPAEC. It was reported that multiple caspase homologues were found in both the cytoplasm and nucleus in etoposid-induced apoptosis in HL-60 cells (Martins, I. M., et al., *J. Biol. Chem.* 272:7421–7430 (1997)). Interestingly, in TNF-gamma-alpha-induced apoptotic BPAEC the immunoreactive 17 kD subunit of caspase-3 was only localized with fragmented nuclei, further indicating a role of caspase-3 in TNF-gamma-alpha-induced apoptosis. Whether this active caspase-3 was transported into the nucleus or the inactive caspase-3 is already in the nucleus awaiting activation promoted by TNF-gamma-alpha requires further investigation. Taken together, these results suggest that caspase-3 was activated by TNF-gamma-alpha-induced cell apoptosis. However, our results cannot exclude other members of this family, especially those closely related to caspase-3, such as caspase-7, in mediating TNF-gamma-alpha-induced apoptosis. Moreover, ZVAD-fmk was less effective at the later time (30 h) compared to the earlier time (14 h) for inhibiting TNF-gamma-alpha-included apoptosis in BPAEC, suggesting a caspase-independent of negative-feedback mechanism may exist at the later phase of TNF-gamma-alpha-induced BPAEC apoptosis.

In summary, the present studies have demonstrated that TNF-gamma-alpha, a novel member of TNF cytokine family, causes endothelial cell apoptosis. TNF-gamma-alpha appears to act through a receptor which is distinct from TNF receptors 1 or 2. The effect of TNF-gamma-alpha is via activation of the stress protein kinases, SAPK/JNK and p38 MAPK., and the caspases, mainly caspase-3 like protease. Apoptotic programmed cell death has been suggested to be a cause of endothelial cell damage contributing to various inflammatory disorders and cardiovascular injury (Karsan, A. *Trends Cardiovasc. Med.* 8:19–24 (1998)). Moreover, endothelial cell apoptosis may be an important mechanism involved in a balance between antianglogenic and proangiogenic processes, and loss of this balance will lead to a variety of diseases such as solid tumor metastasis and retinopathy (Folkman, J. and Shing, J. *J. Biol. Chem.* 267:10931–10934 (1992); Brooks, P. C., et al., *Cell* 79:1157–1164 (1994)).

Numerous modifications and variations of the present invention are possible in light of the above teachings and, therefore, within the scope of the appended claims, the invention may be practiced otherwise than as particularly described.

The entire disclosure of all publications (including patents, patent applications, journal articles, laboratory manuals, books, or other documents) cited herein are hereby incorporated by reference.

Further, the Sequence Listing submitted herewith in both computer and paper forms are hereby incorporated by reference in their entireties.

What is claimed is:

1. An isolated polynucleotide consisting of at least 30 contiguous nucleotides of a nucleic acid sequence selected from the group consisting of: the nucleotide sequence from nucleotides 783 to 1304 of SEQ ID NO:1.

2. The isolated polynucleotide of claim 1, wherein said polynucleotide is ligated to a non-coding nucleic acid sequence.

3. The isolated polynucleotide of claim 1, wherein said polynucleotide encodes a polypeptide.

4. The isolated polynucleotide of claim 3, wherein said polynucleotide is ligated to a second polynucleotide which encodes a heterologous polypeptide.

5. The isolated polynucleotide of claim 4, wherein said polypeptide is fused to said heterologous polypeptide.

6. A method of producing a vector that comprises inserting the isolated polynucleotide of claim 1 into a vector.

7. A vector comprising the isolated polynucleotide of claim 1.

8. The vector of claim 7, wherein said isolated polynucleotide is operably associated with a heterologous regulatory sequence.

9. A host cell comprising the isolated polynucleotide of claim 1.

10. The host cell of claim 9, wherein said isolated polynucleotide is operably associated with a heterologous regulatory sequence.

11. A method of producing a polypeptide encoded by a polynucleotide consisting of at least 30 contiguous nucleotides of the nucleotide sequence from nucleotides 783 to 1304 of SEQ ID NO:1, said method comprising culturing the host cell of claim 10 under conditions such that said polypeptide is expressed, and recovering said polypeptide.

12. The isolated polynucleotide of claim 1, consisting of at least 50 contiguous nucleotides of the nucleotide sequence from nucleotides 783 to 1304 of SEQ ID NO:1.

13. The isolated polynucleotide of claim 12, wherein said polynucleotide is ligated to a non-coding nucleic acid sequence.

14. The isolated polynucleotide of claim 12, wherein said polynucleotide encodes a polypeptide.

15. The isolated polynucleotide of claim 14, wherein said polynucleotide is ligated to a second polynucleotide which encodes a heterologous polypeptide.

16. The isolated polynucleotide of claim 15, wherein said polypeptide is fused to said heterologous polypeptide.

17. A method of producing a vector that comprises inserting the isolated polynucleotide of claim 12 into a vector.

18. A vector comprising the isolated polynucleotide of claim 12.

19. The vector of claim 18, wherein said isolated polynucleotide is operably associated with a heterologous regulatory sequence.

20. A host cell comprising the isolated polynucleotide of claim 12.

21. The host cell of claim 20, wherein said isolated polynucleotide is operably associated with a heterologous regulatory sequence.

22. A method of producing a polypeptide encoded by a polynucleotide consisting of at least 50 contiguous nucleotides of the nucleotide sequence from nucleotides 783 to 1304 of SEQ ID NO:1, said method comprising culturing the host cell of claim 21 under conditions such that said polypeptide is expressed, and recovering said polypeptide.

23. An isolated polynucleotide which encodes a polypeptide consisting of at least 30 contiguous amino acids of SEQ ID NO:2.

24. The isolated polynucleotide of claim 23, wherein said polynucleotide is ligated to a non-coding nucleic acid sequence.

25. The isolated polynucleotide of claim 23, wherein said polynucleotide is ligated to a second polynucleotide which encodes a heterologous polypeptide.

26. The isolated polynucleotide of claim 25, wherein said polypeptide is fused to said heterologous polypeptide.

27. A method of producing a vector that comprises inserting the isolated polynucleotide of claim 23 into a vector.

28. A vector comprising the isolated polynucleotide of claim 23.

29. The vector of claim 28, wherein said isolated polynucleotide is operably associated with a heterologous regulatory sequence.

30. A host cell comprising the isolated polynucleotide of claim 23.

31. The host cell of claim 30, wherein said isolated polynucleotide is operably associated with a heterologous regulatory sequence.

32. A method of producing a polypeptide consisting of at least 30 contiguous amino acids of SEQ ID NO:2, said method comprising culturing the host cell of claim 31 under conditions such that said polypeptide is expressed, and recovering said polypeptide.

33. The isolated polynucleotide of claim 23, which encode a polypeptide consisting of at least 50 contiguous amino acids of SEQ ID NO:1.

34. The isolated polynucleotide of claim 33, wherein said polynucleotide is ligated to a non-coding nucleic acid sequence.

35. The isolated polynucleotide of claim 33, wherein said polynucleotide is ligated to a second polynucleotide which encodes a heterologous polypeptide.

36. The isolated polynucleotide of claim 35, wherein said polypeptide is fused to said heterologous polypeptide.

37. A method of producing a vector that comprises inserting the isolated polynucleotide of claim 32 into a vector.

38. A vector comprising the isolated polynucleotide of claim 33.

39. The vector of claim 38, wherein said isolated polynucleotide is operably associated with a heterologous regulatory sequence.

40. A host cell comprising the isolated polynucleotide of claim 33.

41. The host cell of claim 40, wherein said isolated polynucleotide is operably associated with a heterologous regulatory sequence.

42. A method of producing a polypeptide consisting of at least 50 contiguous amino acids of SEQ ID NO:2, said method comprising culturing the host cell of claim 41 under conditions such that said polypeptide is expressed, and recovering said polypeptide.

* * * * *